US006307038B1

(12) United States Patent
Takahashi et al.

(10) Patent No.: US 6,307,038 B1
(45) Date of Patent: Oct. 23, 2001

(54) EXPRESSION SYSTEMS UTILIZING AUTOLYZING FUSION PROTEINS AND A NOVEL REDUCING POLYPEPTIDE

(75) Inventors: Tohru Takahashi; Nobufusa Serizawa; Ryuta Koishi; Ichiro Kawashima, all of Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/167,151

(22) Filed: Oct. 6, 1998

Related U.S. Application Data

(62) Division of application No. 08/500,635, filed on Jul. 11, 1995, now Pat. No. 5,955,072.

(30) Foreign Application Priority Data

Jul. 13, 1994 (JP) .................................................. 6-161053
Sep. 13, 1994 (JP) .................................................. 6-218392
Dec. 7, 1994 (JP) .................................................. 6-303809

(51) Int. Cl.[7] .................................................. C07H 21/04
(52) U.S. Cl. ...................... 536/23.4; 536/23.2; 424/94.1; 435/252.32; 435/320.1
(58) Field of Search .................. 536/23.1, 23.2, 536/23.4; 435/189, 252.32, 320.1; 424/94.1

(56) References Cited

U.S. PATENT DOCUMENTS

| 5,149,783 | 9/1992 | Sommergruber et al. | ............ 530/300 |
| 5,162,601 | * 11/1992 | Slightom | .............................. 800/205 |
| 6,077,694 | * 5/2000 | Medablimi | ......................... 435/69.7 |

FOREIGN PATENT DOCUMENTS 321973   6/1989   (EP) .

WO 93/05071   3/1993   (WO) .
WO 95/21249   8/1995   (WO) .

OTHER PUBLICATIONS

Boye. Accesion X63358 S38044. Bean yellow mosaic virus 3' part of genome Jun. 30, 1993.*
K. Boye et al., *Plant Molecular Biology*, 18, 1203–1205, 1992, "cDNA cloning and sequencing of the bean yellow mosaic virus nuclear inclusion protein genes".
Database EMBL, Heidelberg, BRD, AC H11561, Jul. 3, 1995, Hillier, L. et al.: "The WashU–Merck EST Project", XP002025149, (abstract).
Pamela Y. Gasdaska, John R. Gasdaska, Shawn Cochran and Garth Powis, *FEBS Letters*, vol. 373, No. 1, Oct. 2, 1995, pp. 5–9, "Cloning and Sequencing of a Human Thioredoxin Reductase".
Chang et al. (1988), *Phytopathology*, 78, 1266–1275.
Dougherty et al. (1990) in Viral Genes and Plant Pathogenesis, Pirone, TP and JG Shaw, eds. Springer–Verlag, New York.
Hopp et al. (1988), *Bio/Technology*, 6, 1204–1210.

* cited by examiner

*Primary Examiner*—Nashaat T. Nashed
*Assistant Examiner*—Christian L Fronda
(74) *Attorney, Agent, or Firm*—Frishauf, Holtz, Goodman, Langer & Chick, P.C.

(57) ABSTRACT

The present invention provides expression systems for exogenous polypeptides wherein the polypeptide is expressed as a fusion protein together with clover yellow virus Nuclear Inclusion a (NIa), the NIa component serving to autolyze the fusion protein after expression. This system can be used to express a novel polypeptide which we have designated KM31-7 protein and which is capable of reducing dichloroindophenol and reduced glutathione. This polypeptide is useful in the treatment of disorders caused by oxidative stress.

46 Claims, 13 Drawing Sheets

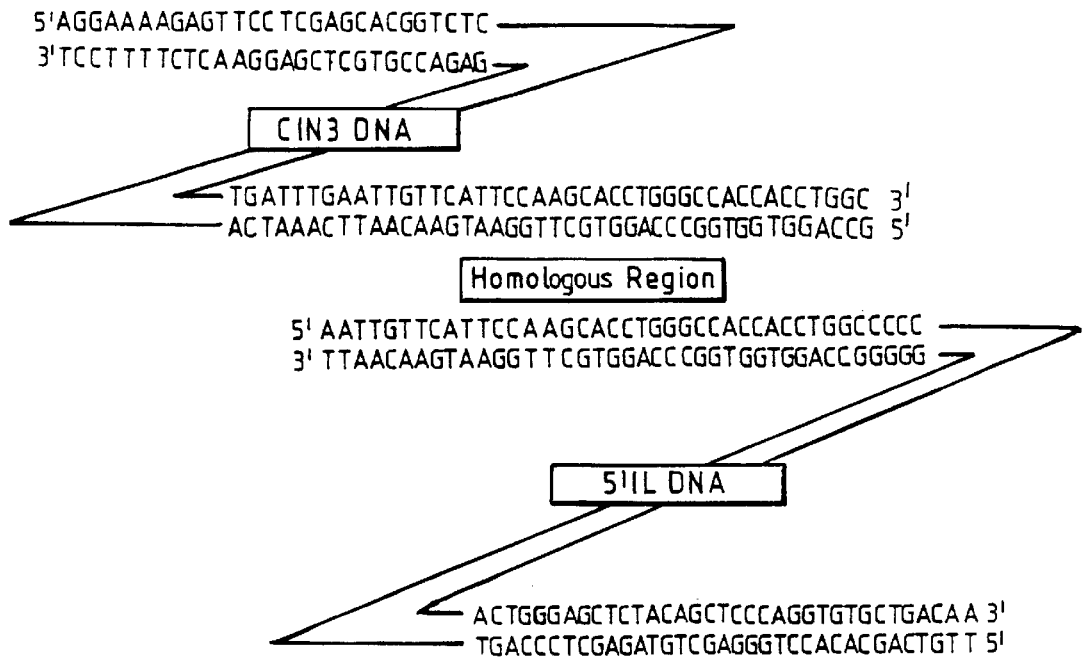
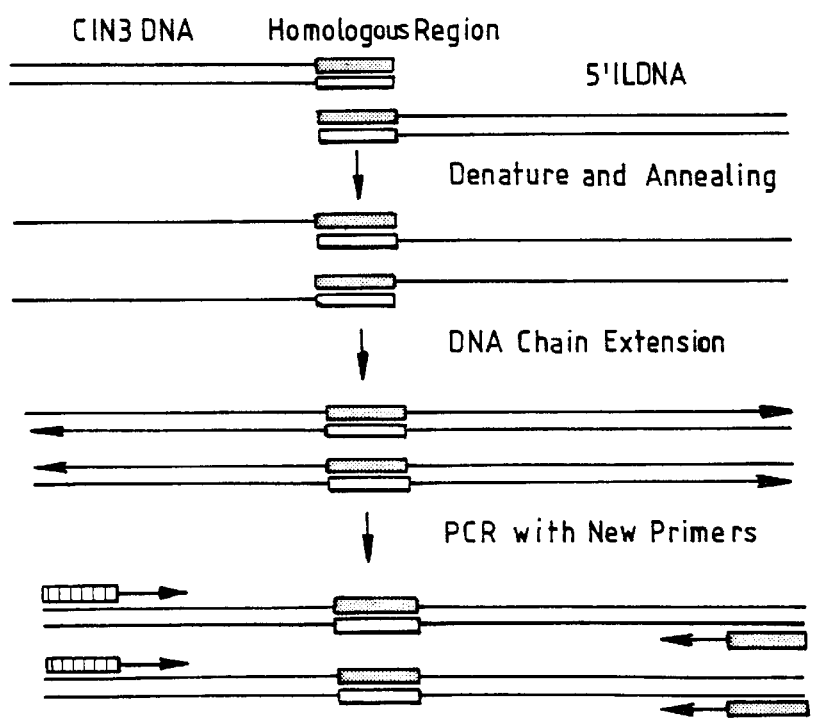
FIG. 5

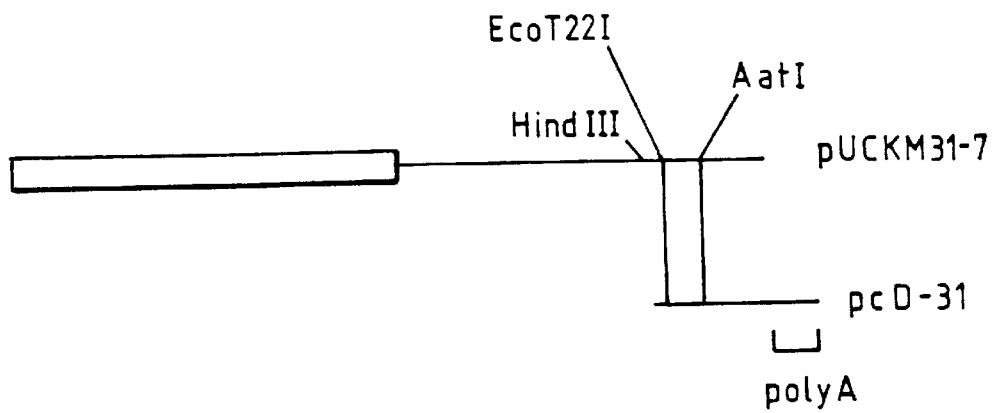

```
pUCKM31-7:......CATATTCAGTTTTATTTATTTATTTTTAATTTGTTTTTTTCTCC pcD-31: ................................................

AAGTCCACCAGTCTCTGAAATTAGAACAGTAGGCGGTATGAGATAATCAG

..................................................

GCCTAATCATGTTGTGATTCTCTTTTCTTAGTGGAGTGGAATGTTCTATC
         ||||||||||||||||||||||||||||||||||||||||||||||||||
        .CCTAATCATGTTGTGATTCTCTTTTCTTAGTGGAGTGGAATGTTCTATC

CCCACAAGAAGGATTATATCTTATAGACTTGTCTTGTTCAGATTCTGTAT
         ||||||||||||||||||||||||||||||||||||||||||||||||||
         CCCACAAGAAGGATTATATCTTATAGACTTGTCTTGTTCAGATTCTGTAT

TTACCCATTTTATTGAAACATATACTAAGTTCCATGTATTTTTGTTACAA
         ||||||||||||||||||||||||||||||||||||||||||||||||||
         TTACCCATTTTATTGAAACATATACTAAGTTCCATGTATTTTTGTTACAA

ATCTTCTGAAAAAAAACAAAACAATGTGAAACATTAAAATTAAAAGGCAT
         ||||||||||||||||||||||||||||||||||||||||||||||||||
         ATCTTCTGAAAAAAAACAAAACAATGTGAAACATTAAAATTAAAAGGCAT

TAATA.............................................

TAATAATAAAAAAAAAAAAAAAAAAAAAAAAAAAAAAAAAAAAAAAAAAA.
```

FIG. 8

EXPRESSION SYSTEMS UTILIZING AUTOLYZING FUSION PROTEINS AND A NOVEL REDUCING POLYPEPTIDE

This is a division of application of Ser. No. 08/500,635 filed Jul. 11, 1995 (U.S. Pat. No. 5,955,072).

FIELD OF THE INVENTION

The present invention relates to polypeptide expression systems requiring cleavage of a precursor product, and to proteases for use in such systems. The present invention further relates to a novel polypeptide capable of reducing dichloroindophenol and oxidized glutathione, DNA encoding the novel polypeptide, vectors containing such DNA, hosts transformed with such vectors, and pharmaceutical compositions containing the polypeptide. In addition, the present invention also relates to monoclonal antibodies against this polypeptide, and a process for isolating and purifying the polypeptide using such an antibody.

PRIOR ART

The Potyviruses are a group of viruses each of which have a single-stranded, RNA genome of approximately 10,000 bases and which infects plants such as the family Solanaceae. The Potyvirus genome is characterized by possessing one extremely long open reading frame, or ORF, [Dougherty, W. G. and Hiebert, E. (1980), Virology 101: 466–474.; Allison, R. et al. (1986), Virology 154: 9–20]. In order to express the individual proteins encoded within the ORF, the translated polyprotein is digested by two types of protease, both of which are also encoded within the ORF [Dougherty, W. G. and Carrington, J. C. (1988), Ann. Rev. Phytopath. 26: 23–143].

Tobacco etch virus (TEV) is a member of the Potyvirus family, and this virus produces nuclear inclusions which can be stained with trypan blue in the infected cell. The nuclear inclusions apparently consist of two kinds of protein, one of which has proven to be a viral protease, and which has been designated Nuclear Inclusion a, or NIa [J. Virol., 61: 2540–2548 (1987)].

The Nuclear Inclusion a proteases of the Potyviruses recognize and cleave a peptide sequence which includes one of Gln-Gly, Gln-Ser and Gln-Ala, and it is believed that this sequence is hexameric and occurs at the C-terminal end of the relevant NIa within the polyprotein. Cleavage is between the two residues making up the dimers shown above.

The complete genomic sequences of TEV and tobacco vein mottling virus (TVMV), another member of the Potyvirus family, have been determined, and homology searching has allowed the location of the NIa's of these viruses within their respective genomes [Virology, 154: 9–20 (1986); Nucleic Acid Res., 14: 5417–5430 (1986)].

Clover Yellow Vein Virus, or CYVV, is also a Potyvirus. So far, only the gene occurring at the 3' end of the CYVV genome, together with the coat protein it encodes, has been sequenced [Uyeda, I. et al. (1991), Intervirol. 32: 234–245]. The structure of NIa region of the genome has not previously been elucidated, nor has the corresponding NIa been isolated.

The production of exogenous proteins by expression systems can be straightforward, using techniques well known in the art. However, there are many polypeptides which cannot easily be expressed in an exogenous system. The problem may be that the polypeptide cannot be expressed in large amounts, and this cannot usually be corrected merely by placing a regulatory gene upstream. Alternatively, it may be that post-transcriptional events required to obtain the mature form do not take place, or take place incorrectly.

For example, many eukaryotic polypeptides are initially translated with an N-terminal methionine which is subsequently deleted to obtain the mature form. This processing cannot take place in prokaryotes, so that alternative means of obtaining expression have had to be found. One such technique involves fusing the desired exogenous protein with maltose-binding protein or glutathione S-transferase, for example, purifying the expressed fusion protein and then cleaving with a protease, such as Factor Xa, enterokinase, or thrombin. The main drawback of this cumbersome method is that it requires two purification steps, which results in a substantial loss of the end product.

U.S. Pat. No. 5,162,601 discloses the use of TEV protease in the manufacture of a polyprotein having linker sequences between each of the proteins it is desired to express, such as human tPA. However, this patent only discloses the cloning of a multigene encoding this polyprotein into a host. There is no disclosure of expression or purification of the proteolytically cleaved end product.

Oxygen for metabolic energy is generally provided in the form of oxidizing agents in the cellular environment. The activated form in which the oxygen is used is generally as a free radical, such as superoxide ($O_2^-$), peroxide ($H_2O_2$) or a hydroxy radical ($OH^-$), all of which are reduced to form water ($H_2O$) after use. Oxygen gas, itself, is highly oxidizing, but the term "activated oxygen", as used herein, relates to oxygen and oxygen-containing molecules which have greater oxidizing potential than atmospheric oxygen. The most potent form of activated oxygen is the free radical, which is a molecule or atom having one or more unpaired electrons.

Free radicals are typically unstable and, if not properly controlled, can denature lipids, proteins and nucleic acids. Consequently, although activated oxygen is essential to life, it is also a potential health hazard, and must be very closely controlled. Even in vanishingly small amounts, activated oxygen can cause disorders, due to high reactivity. As a result, living organisms are unable to survive unless they are equipped with a defense mechanism against activated oxygen.

In the cellular environment, the locations, amounts and times of generation of activated oxygen must be carefully balanced against the cell's ability to neutralize the associated danger. This ability is typically provided by a defense mechanism that uses its own antioxidants or antioxidation enzymes. In the context of the present invention, an "antioxidant" is the generic name for a naturally occurring substance which is able to prevent or inhibit the autooxidation of lipids, for example. The term "antioxidation enzyme" is used generically for an enzyme which catalyzes a reaction which eliminates activated oxygen, the term "antioxidative action" being construed accordingly.

Excessive amounts of activated oxygen are produced in a number of abnormal circumstances, such as when a person is stressed, is taking drugs, smokes, undergoes surgery, has an organ transplant or if he suffers ischemia through a cerebral or myocardial infarction. These large amounts are more than the control systems of the body can eliminate, so that the excess of activated oxygen can cause further damage to the body, seriously impairing normal cells. The resulting, so-called oxidative stress is responsible for a great many disease conditions.

To take arteriosclerosis as an example, the occurrence of low specific gravity lipoproteins which have been oxidized by activated oxygen is considered to be one of the causes of the disease [Steinberg, D. (1983,) Arteriosclerosis 3, 283–301]. Oxidative stress is also considered to be intimately involved with cause and effect in the mechanisms associated with the occurrence, metabolic abnormalities and vascular complications of diabetes [Kondo, M. ed., "Approaches from Modern Medicine (4) Free Radicals", Medical View Pub., pp. 138–146].

Activated oxygen is also implicated in other pathological states and conditions, such as; ischemic disorders (reperfusion disorders, ischemic heart disease, cerebroischemia, ischemic enteritis and the like), edema, vascular hyperpermeability, inflammation, gastric mucosa disorders, acute pancreatitis, Crohn's disease, ulcerative colitis, liver disorders, Paraquat's disease, pulmonary emphysema, chemocarcinogenesis, carcinogenic metastasis, adult respiratory distress syndrome, disseminated intravascular coagulation (DIC), cataracts, premature retinopathy, auto-immune diseases, porphyremia, hemolytic diseases, Mediterranean anemia, Parkinson's disease, Alzheimer's disease, epilepsy, ultraviolet radiation disorders, radioactive disorders, frostbite and burns.

Several defence mechanisms exist both inside and outside cells for the sole purpose of eliminating activated oxygen generated physiologically.

Intracellularly, antioxidants and antioxidative enzymes, such as those given below, are known to process and eliminate activated oxygen. For example, catalase is present in peroxisomes, and this enzyme reduces and removes hydrogen peroxide. Glutathione peroxidase occurs in the cytoplasm and the mitochondria, and this enzyme reduces and detoxifies hydrogen peroxide and lipid peroxides in the presence of reduced glutathione. Transferrin, ferritin and lactoferrin, for example, inhibit the generation of activated oxygen by stabilizing iron ions, while ceruloplasmin performs a similar function in connection with copper ions. In addition, superoxide dismutase, which is present in the cytoplasm and mitochondria, catalyzes the reduction of superoxides to form hydrogen peroxide, the hydrogen peroxide then being eliminated by catalase, for example. In addition, vitamins C and E, reduced glutathione and other low molecular weight compounds are also capable of reducing and eliminating activated oxygen.

On the other hand, such agents as extracellular superoxide dismutase, extracellular glutathione peroxidase and reduced glutathione exist in the extracellular environment, and these have similar modes of action to their intracellular counterparts listed above. However, compared to the intracellular situation, there are fewer types of extracellular antioxidants and antioxidative enzymes, and there is only a small number that exhibit extracellular antioxidative action.

Reduced glutathione has an important function in maintaining the reduced state both inside and outside cells, and it is represented by the formula below. Glutathione was first discovered in yeast by de-Rey-Pailhade in 1888, and it was later named glutathione following its isolation as a compound by Hopkins in 1921.

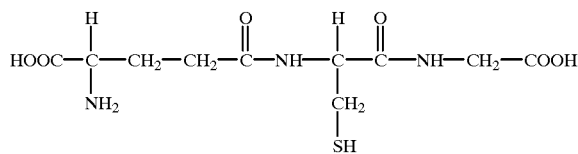

Glutathione is composed of three amino acids: glutamic acid, cysteine and glycine. The thiol groups of two glutathione molecules can be oxidized to form a disulfide bond in the presence of activated oxygen, thereby reducing the activated oxygen.

Glutathione is mainly produced in the liver, and circulates within the body via the plasma. In the normal body, glutathione exists nearly entirely in the reduced form. When levels of the oxidized form increase, then the reduced form is regenerated by the action of glutathione reductase in the presence of nicotinamide adenine dinucleotide phosphate (NADPH). Thus, reduced glutathione protects the cell membrane from oxidative disorders and functions by the reducing activated oxygen and free radicals. As a result of having this antioxidative property, reduced glutathione also protects against the effects of radioactivity and is useful as a therapeutic drug for cataracts. It has also recently been reported that systemic levels of reduced glutathione are reduced in AIDS patients, which tends to indicate that the role of reduced glutathione in the body is extremely important. However, in abnormal conditions, the amount of activated oxygen can be so great that virtually all glutathione is in the oxidized state, so that activated oxygen is not removed as fast as possible.

Human thioredoxin is a second example of a substance which exerts various physiological actions by means of its reducing activity, both inside and outside cells. Human thioredoxin (also known as Adult T Cell Leukemia Derived Factor, ADF) was cloned as a factor which was capable of inducing interleukin 2 receptors (IL-2R) in adult T cell leukemia cell lines. It is a thiol-dependent reductase with two cysteine residues at its active site, and it is capable of reducing activated oxygen and free radicals.

In addition to inducing IL-2 receptors, human thioredoxin also: promotes cell growth in B cell strain 3B6 which is infected with Epstein-Barr virus (EBV); protects against tumor necrosis factor (TNF) derived from monocyte-origin cell line U937; and protects against vascular endothelial cell impairment by neutrophils. Further, in the intracellular environment, human thioredoxin acts on the transcription factors NFkB, JUN and FOS through its reducing activity, thereby to promote DNA bonding activity and enabling it to function to increase transcriptional activity. Human thioredoxin is currently being developed as a protective agent for radioactivity disorders, as well as for a therapeutic drug for reperfusion disorders, rheumatoid arthritis and inflammations, all of which disorders can be protected against by its ability to protect against cellular impairment via its reducing activity.

As has been described above, it is physiologically extremely important to maintain both the intracellular and extracellular environments in a reduced state by elimination of activated oxygen and free radicals. There are believed to be many, as yet unknown, antioxidants and antioxidative enzymes, both inside and outside cells, that have a role to play in removing activated oxygen and free radicals. Accordingly, it would be extremely useful to find a reducing substance which was capable of regenerating, for example, reduced glutathione. Such a substance could help in abnormal bodily conditions, such as those described above.

SUMMARY OF THE INVENTION

It is a first object of the present invention to provide a novel protease, a nucleotide sequence encoding the protease, a vector containing a DNA sequence encoding the protease, and a host cell which has been transformed with said vector.

It is a second object of the present invention to provide DNA encoding a protein of interest and also encoding the novel protease upstream from said protein, a sequence between the two said sequences further encoding a peptide cleavable by said protease, all of said sequences being in the same open reading frame. It is also an object to provide a protein encoded by said DNA, as well as a vector containing said DNA and an expression system comprising said vector, said vector being able to replicate autonomously in an appropriate host cell, such as by comprising a nucleotide sequence required for autonomous replication.

In the alternative, it is a first object of the present invention to provide a nucleotide sequence encoding a novel polypeptide having reducing activity in vivo. It is also an object to provide such DNA which encodes a peptide which is capable of reducing dichloroindophenol and oxidized glutathione.

It is a further object of the present invention to provide a recombinant vector comprising the above-mentioned DNA, said vector being able to replicate autonomously in an appropriate host cell, such as by having a base sequence enabling autonomous replication.

Moreover, it is a yet further object of the present invention to provide a host cell microorganism which has been transformed with the above-mentioned recombinant vector. It is also an object to provide the above-mentioned peptide as an expression product from the transformed host cell, and to provide a monoclonal antibody against the peptide. We have now identified and cloned the novel CYVV protease (NIa) and have surprisingly found that it is possible to use CYVV NIa as part of a fusion protein which can be expressed in such hosts as *E. coli* and which allows the production of large quantities of the fusion protein which can self-cleave to yield the desired exogenous protein. The CYVV NIa gene can be stably maintained and expressed in *Escherichia coli*, and the expressed NIa retains its activity as a specific protease, even when the protein forms part of a fusion protein.

We have also discovered DNA that codes for a novel polypeptide which is capable of reducing dichloroindophenol {also known as dichlorophenol-indophenol, 2,6-dichloroindophenol, or 2,6-dichloro-4-[(4-hydroxyphenyl)imino]-2,5-cyclohexadien-1-one} and oxidized glutathione, said polypeptide being obtainable in large amounts by the use of appropriate genetic engineering techniques. This polypeptide is particularly useful in the therapy of conditions caused by, or related to, oxidative stress, or any disease caused by activated oxygen, such as arteriosclerosis, diabetes and ischemic disorders (including reperfusion disorders, ischemic cardiac diseases, cerebroischemia and ischemic enteritis).

Thus, in a first aspect of the first embodiment of the present invention, there is provided a polynucleotide sequence wherein said sequence comprises, in the 5' to 3' direction and in the same open reading frame:

a) a sequence encoding the clover yellow vein virus Nuclear Inclusion a protein, or a mutant or variant thereof having similar proteolytic specificity to that of clover yellow vein virus Nuclear Inclusion a protein;

b) a sequence encoding a peptide recognizable by and cleavable by said clover yellow vein virus Nuclear Inclusion a protein, or said mutant or variant thereof; and c) at least one sequence encoding a polypeptide.

The present invention also provides a sequence encoding the clover yellow vein virus Nuclear Inclusion a protein, or a mutant or variant thereof having similar proteolytic specificity to that of clover yellow vein virus Nuclear Inclusion a protein.

The present invention further provides a vector, especially an expression vector, containing a sequence as defined above.

The present invention still further provides a host transformed with a vector as defined above, as well as an expression system comprising said host and said expression vector, and also a polypeptide produced by such an expression system.

In the alternative embodiment of the invention, there is provided, in a first aspect, a polynucleotide sequence encoding a polypeptide having the amino acid sequence of amino acid numbers 1 to 526 of sequence ID number 12, or which encodes a mutant or variant of said polypeptide, provided that the polypeptide encoded by the polynucleotide sequence is capable of reducing dichloroindophenol and oxidized glutathione.

There is also provided a vector, especially an expression vector, containing a sequence as defined above.

The present invention still further provides a host transformed with a vector as defined above, as well as an expression system comprising said host and said expression vector, and also a polypeptide produced by such an expression system.

The invention also provides the above polypeptide for use in therapy, as well as the use of such a polypeptide in the treatment and prophylaxis of conditions caused by, or related to, oxidative stress, or any disease caused by activated oxygen, and pharmaceutical compositions comprising the polypeptide.

There is yet further provided an antibody, especially a monoclonal antibody, and equivalents thereof, against the polypeptide, and the invention additionally provides a method of producing such an antibody and a method of purification of the polypeptide using the antibody.

BRIEF DESCRIPTION OF THE DRAWINGS

The present invention will be illustrated with respect to the accompanying drawings, in which:

FIG. 2 shows construction of plasmid pKNI5' containing a 5'-region of NIa;

Figure 4:
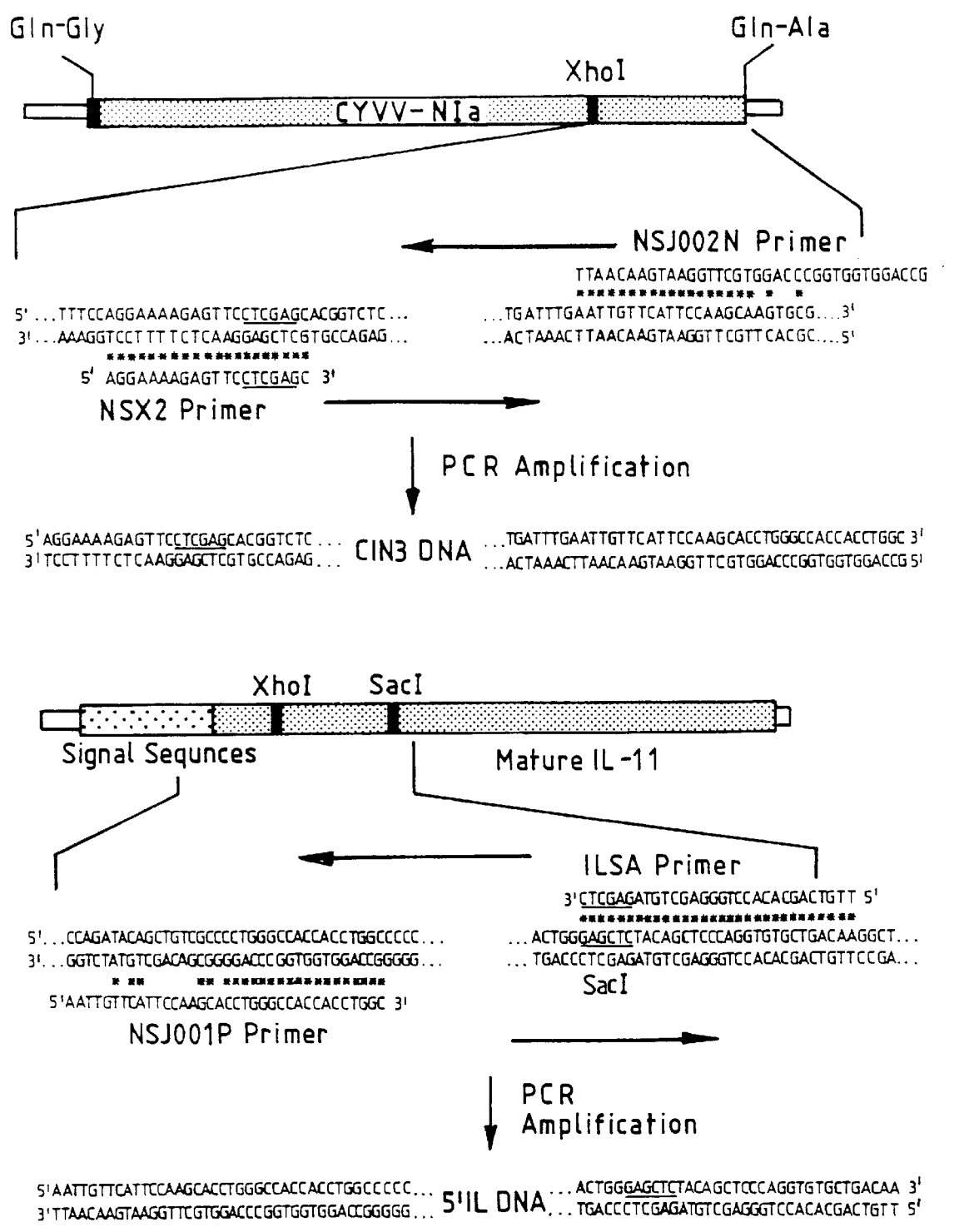

FIG. 4 shows primers which were used to prepare the 5' IL DNA fragment the CIN3 DNA fragment and in which the 3'-terminus of NIa gene and the 5'-terminus of IL-11 gene are fused;

FIG. 5 shows the fusion of the CIN3 DNA fragment and the IL5'DNA fragment by PCR;

FIG. 8 is a comparative diagram of the nucleotide sequences of the 3' terminals in pUCKM31-7 and pcD-31;

DETAILED DESCRIPTION OF THE INVENTION

Figure 1:
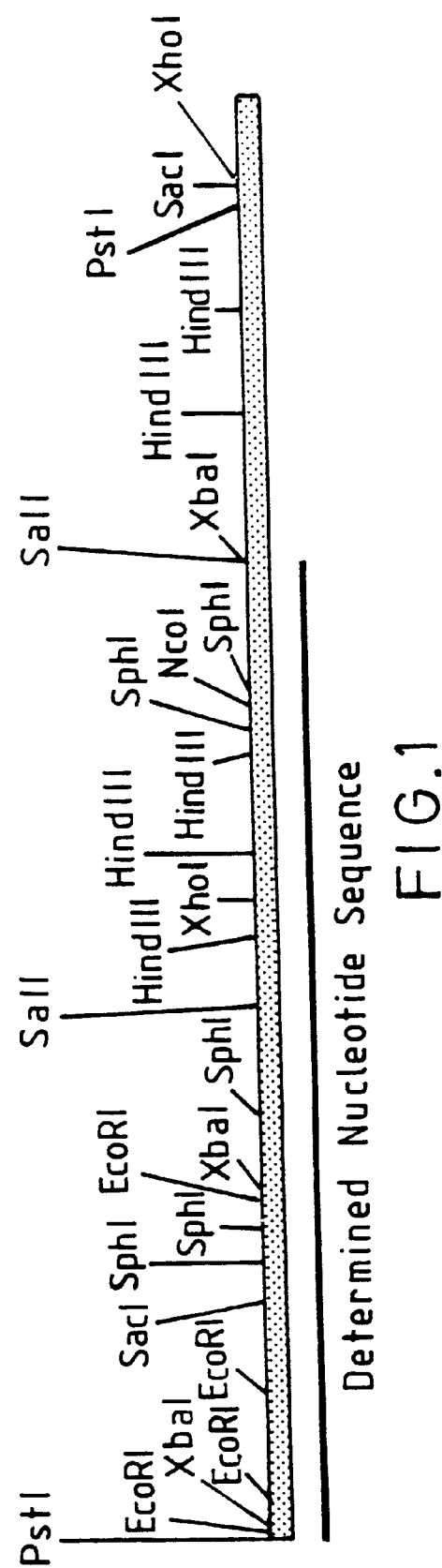
FIG. 1 is a restriction enzyme map of cDNA of the NIa region isolated from CYVV-cDNA.

The present invention will be illustrated firstly by reference to the first embodiment of the present invention, but the following discussion is also appropriate to the second embodiment of the invention, unless it is clear that the discussion is not applicable to the second embodiment.

It will be appreciated that it is preferred for the polynucleotide sequence of the invention generally to be in the form of DNA, and references hereon in will generally be to DNA, for this reason. However, such references also include RNA, where appropriate. RNA is not so preferred, as uses therefor are limited by practicality. For example; mRNA can be expressed in xenopus oocytes or a wheat germ lysate system, but neither of these is practical for producing large amounts of the fusion protein on an economic basis.

As used herein, the term "peptide" means any molecule comprising 2 or more amino acids linked via a peptide bond. As such, the term includes oligopeptides, polypeptides and proteins. The term "fusion protein" relates to any single polypeptide obtained by combining two or more other peptide sequences.

It will also be appreciated that the sequence of the invention is preferred to be in the form of a double strand, and that the present invention also envisages the antisense sequence corresponding to the sequence of the invention. The double strand (or ds) sequence of the invention may have one or two "sticky" ends, in which case the antisense and sense strands will not necessarily correspond exactly.

The protein encoded by the sequence identified in a) above is intended to cleave the peptide encoded by the sequence of b) above in order to release the polypeptide(s) encoded by the sequence of c) above when the sequence of the invention is expressed in a suitable expression system.

Cleavage of the fusion protein may take place at any time after the sequences of a) and b) above have been translated. As such, it will be appreciated that the polypeptide encoded by c) above need not have been fully translated before cleavage. However, in practice, we have found that at least some of the fusion protein, if not the majority, is fully translated prior to cleavage.

Where the sequence of c) above encodes more that one polypeptide, then it is necessary to encode further cleavage sequences between each encoded polypeptide, unless it is desired, for example, to obtain an uncleaved, fused plurality of polypeptides.

If the sequence of c) above encodes more than one polypeptide, then the sequence may be susceptible to attenuation in a transcription environment. In the process of attenuation, transcription of the mRNA sequence of the invention stops before the whole of the mRNA has been read, so that polypeptides encoded nearer the 3' end of the sequence will be produced in smaller amounts than those encoded nearer to the 5' end. Attenuation is not generally a problem, except where several polypeptides are encoded and/or the polypeptides are very long.

It is also generally preferred for the sequence of c) above to encode only one polypeptide, unless it is desired to prepare a plurality of peptides for use together, or where such a plurality is fused. Otherwise, it is necessary to isolate the individual polypeptides after cleavage, and this can be cumbersome and waste the end product through purification procedures.

However, where the sequence in c) above encodes more than one polypeptide, and there is a cleavage sequence between each encoded polypeptide, then the cleavage sequence does not necessarily have to recognized by CYVV NIa. All that is necessary is for the cleavage sequence between the sequence of a) and the 5' end of the sequence of b) to be recognized by the protease encoded by the sequence of a). Where it is desired or acceptable to allow the fusion protein to self-digest to prepare a plurality of polypeptides, then any further cleavage sequences may be recognizable by the protease encoded by the sequence of a). However, such further sequences may be selected so that they are cleavable by other means, so that the fusion protein is cleaved by its NIa portion after transcription to yield NIa and a polyprotein. The NIa can then be removed and the polyprotein cleaved by, for example, Factor Xa or trypsin.

The cleavage peptide encoded by the sequence of b) above (also referred to herein as "cleavage sequence" and "cleavage peptide") may be a sequence which is wholly or partly comprised in either of the sequences encoded for by the sequences of a) and c) ("NIa" or "protease", and "polypeptide", respectively). Thus, the N-terminal end of the cleavage peptide may also be included in the C-terminal sequence of the protease, while the the C-terminal portion of the cleavage peptide may be included in the N-terminal portion of the polypeptide. In such an instance, the cleavage peptide has no independent existence, and the recognition site for the protease is made up from the C-terminal of the protease and the N-terminal of the polypeptide.

The cleavage peptide may also be included in only part of either the protease or the polypeptide. In such an instance, the N-terminal of the cleavage peptide will normally be included in the C-terminal portion of the protease, and the N-terminal portion of the polypeptide will either be linked directly to the cleavage sequence or there may be one or more amino acid residues between the polypeptide and the linker.

Where there are one or more amino acid residues between the cleavage sequence and the protease and/or the cleavage sequence and the polypeptide, then the number and nature of such residues should be such as not to prevent the action of the protease. Excess amino acid residues on the N-terminal of the polypeptide will not generally be advantageous where such residues have to be removed in order to obtain the mature form of the polypeptide. It is generally preferred, where possible, and in the absence of contraindications, to engineer the cleavage peptide so that the mature form of the desired protein is obtained on cleavage of the fusion protein. However, it is entirely possible to obtain a protein having Gly, Ser or Ala attached to the N-terminal for example, and these can be removed by the action of a suitable aminopeptidase, if desired.

In some instances, it may be desirable to encode a proline between the N-terminal of the polypeptide and the cleavage sequence. This allows cleavage of residues up to the proline residue by the action of aminopeptidase P (3.4.11.9), for example, but not beyond. Instead, the proline residue can then be removed by the action of proline iminopeptidase to yield the mature protein. This forms a preferred embodiment of the invention.

The sequence of a) encodes a protease that is capable of cleaving the fusion protein encoded by the sequence of the invention. In the present invention, this protease is clover yellow vein virus Nuclear Inclusion a protease, or a mutant or variant thereof having similar proteolytic specificity to that of clover yellow vein virus Nuclear Inclusion a protease.

The clover yellow vein virus NIa protease is encoded by nucleotide numbers 10 to 1311 in sequence ID number 1 in the sequence listing, while the primary sequence of NIa is given by amino acid numbers 4 to 437 in sequence ID number 2 in the sequence listing. These sequences are novel, and form a part of the present invention, as do mutants and variants thereof.

Nuclear Inclusion a has proteolytic activity which specifically hydrolyzes the peptide bond between Gln-Ala, Gln-Gly or Gln-Ser in a substrate peptide. In addition, we have also found that NIa can cleave Gln-Val. Thus, in contrast to other proteases of the Potyvirus family, we have found that CYVV NIa (references to NIa herein should be taken as meaning CYVV NIa, unless otherwise specified) can cleave the sequence AsnCysSerPheGlnX, wherein X is any amino acid residue, but especially Gly, Ala, Val or Ser, and particularly Gly, Ala or Ser.

It will also be appreciated that peptides comprising the sequence AsnCysSerPheGlnX can be cleaved by NIa, especially where such sequence is sterically exposed to the action of NIa. Thus, the present invention also provides a system for the preparation of a polypeptide, wherein a precursor form of the polypeptide containing the sequence AsnCysSerPheGlnX is cleaved by NIa. This system may also comprise other processing steps, as appropriate, either before, after or contemporaneously with the cleavage by NIa.

Although we generally prefer to use a sequence encoding naturally occurring NIa (in accordance with Sequence ID 2), the present invention equally contemplates the use of mutants or variants of NIa.

As stated, the protease should have the same or similar specificity as that of naturally occurring NIa. In this respect, the protease should generally share substantial sequence homology with amino acid residues 4 to 437 in sequence ID number 2 except where it is apparent to one skilled in the art that substantial variation is possible without changing the recognition sequence or reducing activity below useful levels.

In general, it will be appreciated that the activity of any given protein is dependent upon certain conserved regions of the molecule, while other regions have little importance associated with their particular sequence, and which may be virtually or completely redundant. Accordingly, as stated above, the present invention includes any variants and mutants on the sequence which still show a specificity similar to that of naturally occurring NIa. Such variants and mutants include, for example, deletions, additions, insertions, inversions, repeats and type-substitutions (for example, substituting one hydrophilic residue for another, but not strongly hydrophilic for strongly hydrophobic as a rule). Small changes will generally have little effect on activity, unless they are in an essential part of the molecule, and such changes may be as a side-product of genetic manipulation, for example, when generating extra restriction sites, if such is desired.

In general, there will not usually be any particular reason to want to change the structure of NIa, except in circumstances apparent to those skilled in the art. Indeed, most mutations and variations to either the amino acid or coding sequence will be as a result of the isolation of novel variations on the original wild-type virus. Nevertheless deliberate, and even accidental, modifications are not excluded from the present invention, provided that the protease has the necessary specificity and sufficient proteolytic activity.

As used herein, the term "adverse effect" means any effect on specificity or activity which renders the protease significantly less effective than the naturally occurring NIa identified above, to the extent that activity is reduced below a useful level.

Many substitutions, additions, and the like may be effected, and the only limitation is that activity not be adversely affected. In general, an adverse effect on activity is only likely if the 3-D (tertiary) structure of the NIa is seriously affected The term "mutants" is used herein with reference to deletions, additions, insertions, inversions and replacement of amino acid residues in the sequence which do not adversely affect activity. The present invention further includes "variants", this term being used in relation to naturally occurring CYVV NIa which corresponds closely to sequence ID 2, but which varies therefrom in a manner to be expected within a large population. Within this definition lie allelic variation and those peptides from other cultivars showing a similar type of activity and having a related sequence.

It will be appreciated that neither the NIa nor the protein of the second embodiment of the present invention needs to correspond completely to the sequences depicted in Sequence ID's 2 and 12 respectively. The only requirement is that each has the desired activity, even if the polypeptide is only a fraction of the whole of the natural sequence, or even a mutant or variant of such a fraction.

The genes of eukaryotes, such as the interferon gene, are generally considered to demonstrate polymorphism [c.f., Nishi, T. et al. (1985), J. Biochem. 97, 153–159]. This polymorphism results in some cases where one or more amino acids are substituted in a polypeptide, as well as other cases where there are no changes in the amino acid sequence, despite substitution of the nucleotide sequence.

Thus, it will be appreciated that the polynucleotide coding sequence may also be modified in any manner desired, provided that there is no adverse effect on protease activity. Spot mutations and other changes may be effected to add or delete restriction sites, for example, to otherwise assist in genetic manipulation/expression, or to enhance or otherwise conveniently to modify the NIa molecule.

The terms "mutant" and "variant" are also used herein with reference to the polynucleotide sequence, and such references should be construed in an appropriate manner, mutatis mutandis. It will be appreciated that, while a mutant or variant of a peptide sequence will always be reflected in the coding nucleotide sequence, the reverse is not necessarily true. Accordingly, it may be possible for the nucleotide sequence to be substantially changed (see discussion of degeneracy of the genetic code below), without affecting the peptide sequence in any way. Such mutants and variants of the nucleotide sequence are within the scope of the invention.

For example, it has been established that the protein obtained by replacing a cysteine codon in the interleukin 2 (IL-2) gene with a serine codon is still. capable of expressing IL-2 activity [Wang, A. et al. (1984), Science 224: 1431–1433]. Therefore, as long as a sequence encodes a naturally occurring or a synthetic protein having the appropriate NIa activity, then it is included within the present invention.

A gene encoding the NIa of the invention may easily be reverse-engineered by one skilled in the art from sequence ID 2.

It will be appreciated that any one given reverse-engineered sequence will not necessarily hybridize well, or at all, with any given complementary sequence reverse-engineered from the same peptide, owing to the degeneracy of the genetic code. This is a factor common in the calculations of those skilled in the art, and the degeneracy of any given sequence is frequently so broad as to make it extremely difficult to synthesise even a short complementary oligonucleotide sequence to serve as a probe for the naturally occurring oligonucleotide sequence.

The degeneracy of the code is such that, for example, there may be 4, or more, possible codons for the most frequently occurring amino acids. Accordingly, therefore, it can be seen that the number of possible coding sequences for any given peptide can increase exponentially with the number of residues. As such, it will be appreciated that the number of possible coding sequences for the NIa of the invention may have six or more figures. However, it may be desirable to balance the G+C content according to the expression system concerned, and other factors such as codon frequency for the relevant expression system should generally be taken into account.

As stated above, hybridization can be an unreliable indication of sequence homology but, nevertheless, those sequences showing in excess of 50%, preferably 70% and more preferably 80% homology with sequence ID 1 are generally preferred. In each case, it will be appreciated that a protease, as defined, should be encoded.

The present invention also envisages the possible use of a leader sequence encoded upstream of the protease. This would allow the fusion protein to be externalized from the host, and collected in the culture supernatant, for example. The resulting externalized fusion protein would then be allowed to self-digest, and the polypeptide collected. For such signal sequences, any suitable sequence may be used, especially where such has been specifically developed for a given expression system.

The present invention also envisages vectors containing the sequence of the present invention. The general nature of vectors for use in accordance with the present invention is not crucial to the invention. In general, suitable vectors and expression vectors and constructions therefor will be apparent to those skilled in the art, and will be chosen according to precisely what the practitioner wishes to achieve with the sequence, such as cloning or expression.

Suitable expression vectors may be based on 'phages or plasmids, both of which are generally host-specific, although these can often be engineered for other hosts. Other suitable vectors include cosmids and retroviruses, and any other vehicles, which may or may not be specific for a given system. Suitable control sequences, such as recognition, promoter, operator, inducer, terminator and other sequences essential to and/or useful in the regulation of expression, will be readily apparent to those skilled in the art, and may be those associated with CYVV or with the vector used, or may be derived from any other source as suitable. The vectors may be modified or engineered in any suitable manner.

It will be appreciated that sequence ID 2 represents sufficient sequence to encode entire NIa. Terminators, promoters and other such control sequences as desired may be added so as to, for example, facilitate ligation into a suitable vector, or expression, or both.

It will be appreciated that a DNA fragment encoding the NIa of the invention, together with any fragment encoding the cleavage sequence and that encoding the polypeptide(s) may easily be inserted into any suitable vector. Ideally, the receiving vector has suitable restriction sites for ease of insertion, but blunt-end ligation, for example, may also be used, although this may lead to uncertainty over the open reading frame and direction of insertion. In such an instance, it is a matter of course to test hosts transformed with the transfected vector to select vectors having the necessary fragments inserted in the correct direction and in the correct ORF. In order to ensure that the fragments are in the correct ORF, it may be desirable to create a construct of the sequences a), b) and c) which can then be inserted directly into the vector, thereby reducing the uncertainty of obtaining the desired expression vector. Suitable vectors may be selected as a matter of course by those skilled in the art according to the expression system desired.

By transforming *E. coli*, for example, with the plasmid obtained, selecting the transformant with ampicillin or by other suitable means, and adding tryptophan or other suitable promoter inducer (such as indoleacrylic acid), the desired fusion protein may be expressed. The extent of expression may be analyzed by SDS polyacrylamide gel electrophoresis—SDS-PAGE [Laemmli et al., Nature, (1970), 227, pp.680–685].

It will also be appreciated that, where another vector is used, for example, it will be equally acceptable to employ any suitable selection marker or markers, or an alternative method of selection, and/or to use any suitable promoter as required or convenient.

After cultivation, if the fusion protein is to be collected from the host cells, then the transformant cells are suitably collected, disrupted, for example sonicated, and spun-down. Disruption may also be by such techniques as enzymic digestion, using for example cellulase, or by shaking with an agent such as glass beads, but methods such as sonication are generally preferred, as no extra ingredients are necessary. The resulting supernatant may be assayed for polypeptide activity and the cleavage products can be determined by SDS-PAGE, for example.

Conventional protein purification is suitable to obtain the expression product.

The DNA of the present invention may be prepared by isolating the RNA genome from clover yellow vein virus [Uyeda, I. et al. (1975) Ann. Phytopath. Soc. Japan 41: 92–203]. A suitable source of CYVV is American Type Culture Collection No. PV 123. In any event, clover yellow vein virus may be defined as a virus which causes necrosis in *Vicia faba*.

Genomic RNA may be obtained from CYVV particles which have been purified from an infected plant and then reverse transcribed and double-stranded cDNA prepared by known methods.

For the purposes of determining whether a virus is a mutant or variant of the same strain of CYVV, sequence homology is a good indicator. Many types of Potyvirus are known, and they all vary in pathogenicity. Whether a given virus forms a separate member of the family is based on the serological relation of the viral coat proteins and on the homology of the amino acid sequences. Accordingly, viruses which have primary amino acid sequences which share 90% homology are considered to be the same strain, while viruses which have primary amino acid sequences which share less than 70% homology are considered to distinct family members [Shukla, D. D. and Ward, C. W. (1989), Arch. Virol. 106: 171–200]. Based on the various properties of the coat protein of CYVV used in the present invention [Uyeda, I. et al. (1991), Intervirol. 32: 234–245], CYVV is recognized as an independent member of the Potyvirus family. Therefore, any virus having a coat protein primary amino acid sequence homology of 90% or more, or any virus detecting as positive by ELISA using an anti-CYVV anti-serum (for example, American Type Culture Collection No. PVAS-123: clover yellow vein virus antiserum), is defined as being a strain of clover yellow vein virus.

The various plant species upon which CYVV can be grown include; *Phaseolus vulgaris, Vicia faba* and *Pisum sativum*, but *Vicia faba*, especially *Vicia faba* cultivar Wasesoramame, is preferred.

The preferred method for purifying the virus particle involves homogenizing and squeezing a leaf or leaves of an infected plant in a suitable buffer, followed by extraction with an organic solvent, such as chloroform, and repeating differential centrifugation, followed by sucrose density gradient centrifugation.

One way to confirm that the virus particle thus obtained is CYVV can be performed by examining the virus particle under an electron microscope. Another is by inoculating *Vicia faba* with the virus particle in order to observe whether any symptoms occur.

Suitable methods for extracting the genomic RNA from virus particles include the guanidinium thiocyanate/phenol method, the guanidinium thiocyanate/trifluoro-cesium method and the phenol/SDS method. However, we prefer to use the alkaline sucrose density gradient centrifugation method [Dougherty, W. G. and Hiebert, E. (1980) Virology 101: 466–474].

The RNA obtained as described above can then be tested to confirm that it indeed encodes a protease by translation in a cell-free translation system. Autolysis (self-digestion) can then be detected where the RNA codes for more than just the protease in the total translation product, by monitoring any change in the molecular weights of harvested products from the lysates. Such monitoring can be performed by means of an anti-coat protein antibody, for example.

Should it be required, then the production of translation product can be monitored with passage of time using an anti-coat protein antibody, for example, with the genomic RNA being translated by injection into *Xenopus laevis* oocytes [Gurdon, J. B. (1972), Nature 233: 177–182], or by using a rabbit reticulocyte or a wheat germ lysate system [Schleif, R. F. and Wensink, P. C. (1981), in "Practical Methods in Molecular Biology" Springer-Verlag, N.Y.].

Single stranded DNA can be synthesized by using the thus obtained genomic RNA as a template using a reverse transcriptase, and ds-cDNA can be synthesized from the single-stranded (ss) cDNA by following standard procedures. Suitable methods include the S1 nuclease method [Efstratidiatis, A. et al. (1976), Cell 7: 279–288: Okayama, H. and Berg, P. (1982), Mol. Cell. Biol. 2: 161–170 and others], the Land method [Land, H. et al. (1981) Nucleic Acids Res. 9, 2251–2266] and the O. Joon Yoo method [Yoo, O. J. et al. (1983) Proc. Natl. Acad. Sci. USA 79, 1049–1053]. Of the various options, we prefer to use the Gubler-Hoffman method [Gubler, U. and Hoffman, B. J. (1983), Gene 25: 263–269].

The thus obtained ds-cDNA can then be incorporated into a cloning vector, such as a plasmid or lamdha phage, and the resulting recombinant vector then transformed into a microorganism, such as *Escherichia coli*. *E. coli* strain DH5α is particularly preferred. Transformants can then be selected by their resistance to bactericidal agents, such as tetracycline or ampicillin by techniques well known in the art.

Transformation can, for example, be carried out by the Hanahan method [Hanahan, D. (1983), J. Mol. Biol. 166: 557–580], wherein the recombinant DNA vector is introduced into a cell which has been made competent by treatment with calcium chloride, magnesium chloride or rubidium chloride.

Suitable methods for selecting transformants having NIa DNA are as shown below.

(1) Screening with a Probe

If it is desired to start from wild-type CYVV, then one way to isolate the appropriate RNA is to use a cDNA probe, given that the amino acid sequence of NIa has been elucidated (the portion of the sequence used may be from any region of NIa). Thus, an oligonucleotide corresponding to the relevant amino acid sequence is synthesized. In general, the amino acid sequence chosen will involve the least amount of degeneracy possible, otherwise it will be necessary to produce several probes using the various codons possible. In such an instance, it is likely to be of assistance to take codon usage frequency into consideration. Alternatively, plural nucleotide sequences can be considered, and inosine can be used to replace nucleotides which vary. The probe can then be labeled with a radioisotope, such as $^{32}P$, $^{35}S$ or biotin. Transformant strains can then be detected by fixing denatured plasmid DNA on nitrocellulose filters using the radiolabelled probes, positive clones being detectable by autoradiography.

(2) Using a PCR Probe

In this technique, oligonucleotides both from the sense strand and from the anti-sense strand corresponding to a portion of the known amino acid sequence can be synthesized and the polymerase chain reaction [Saiki, R. K. et al. (1988), Science 239, 487–491] carried out. These can then be used in combination to amplify a DNA fragment encoding NIa. Suitable template DNA is cDNA obtained through reverse transcription of viral genomic RNA known to encode NIa. The thus prepared DNA fragments are labeled, such as with $^{32}P$, $^{35}S$ or biotin, and colony hybridization or plaque hybridization is carried out with this probe to select the clone of interest.

(3) Screening by Exogenous Production in an Animal Cell

This method involves culturing a transformant strain to amplify a gene, followed by transfecting the gene into an animal cell (generally using either a plasmid which is replication competent and containing a transcription promoter region, or using a plasmid which can be integrated into an appropriate chromosome) to express a protein encoded by the gene. By measuring the relevant activity, a strain c an be selected.

(4) Selection Using an Antibody Against NIa

Antibody is produced against the nuclear inclusions (NIa and Nib) from a plant infected with CYVV, or is produced against a protein produced by an expression vector in an appropriate system. The antibody, or its anti-antibody, can then detect the desired NIa or strain of interest.

(5) Selective Hybridization Translation System

Transformant cDNA is hybridized with mRNA from cells which express NIa, as described above, and the mRNA bound to the cDNA is dissociated and recovered. The recovered mRNA is translated into protein in a translation system, for example, by injection into *Xenopus laevis* oocytes, or into such cell-free systems as rabbit reticulocyte lysate or wheat germ lysate. The strain of interest is selected by examining the activity of NIa or by detecting Nia by means of an antibody to NIa.

The DNA encoding CYVV NIa can be obtained from the transformant strains of interest by known methods [c.f.

Maniatis, T. et al. (1982), in "Molecular Cloning A Laboratory Manual" Cold Spring Harbor Laboratory, N.Y.]. For example, a fraction which corresponds to a vector DNA is separated from the cells, and the DNA region which codes for said protein is excised from said plasmid DNA.

Determination of the thus obtained DNA sequence can be carried out by using, for example, the Maxam-Gilbert chemical modification method [Maxam, A. M. and Gilbert, W. (1980), in "Methods in Enzymology" 65: 499–276], or by using, for example, a dideoxynucleotide chain termination method using the M13 phage [Messing, J. and Vieira, J. (1982), Gene 19: 269–276].

In recent years, fluorochromes have tended to replace the use of the more dangerous radioisotope for the determination of DNA sequences. In addition, dideoxynucleotide chain termination is now generally performed by a robot under computer control. Systems which read base sequences after electrophoresis are also proliferating, and examples include the "CATALYST 800" sequencing robot and the 373A DNA sequencer (Perkin-Elmer Japan Applied Biosystems). These systems enable DNA base sequence determination procedures to be performed both efficiently and safely.

The vectors of the present invention can generally be so organized that they can be expressed in "standard cells", either prokaryotic or eukaryotic. In addition, by introducing an appropriate promoter and a sequence for phenotypic expression into the vector, the gene can be expressed in assorted host cells.

Suitable prokaryotic hosts include *Escherichia coli* and *Bacillus subtilis*. For phenotypic expression of the relevant gene, the vector can suitably contain a replicon originating from a species which is compatible with the host. In *E. coli*, a plasmid might contain a replication origin and a promoter sequence such as lac or UV5. Vectors which can confer selectivity based on phenotypic character (phenotype) to a transformed cell are preferred.

*Escherichia coli* is often used as the host, and strain JM 109 derived from *E. coli* strain K12 is a preferred host. Vectors for *E. coli* are, presently, generally selected from pBR322 or the pUC series of plasmids, but other strains and vectors can be used, as desired. Suitable promoters for *Escherichia coli* include the lactose promoter (lac), the tryptophan promoter (trp), the tryptophan-lactose (tac) promoter, the lipoprotein (lpp) promoter, the lambda (λ) PL promoter (from λ phage) and the polypeptide chain elongation factor Tu (tufb) promoter, but the present invention is not limited to these promoters.

Suitable strains of *Bacillus subtilis* include strain 207–25. Suitable vectors include pTUB228 [Ohmura, K. et al. (1984), J. Biochem. 95: 87–93] and others. A suitable promoter is the regulatory sequence of the *Bacillus subtilis* α-amylase gene. This is an appropriate example wherein a signal peptide sequence (from α-amylase), can be used for extracellular secretion.

If it is desired to express the fusion protein in eukaryotic cells, then cells from vertebrates, insects, yeasts, plants, etc. may be used. The preferred vertebrate cells are COS cells, especially COS-1 cells [e.g. Gluzman, Y. (1981), Cell 23: 175–182], or a Chinese hamster ovary cell line (CHO) deficient in dihydrofolate reductase [Urlaub, G. and Chasin, L. A. (1980), Proc. Natl. Acad. Sci. USA 77, 4216–4220], although the present invention is not limited to these.

As stated above, COS cells are suitably employed as vertebrate host cells, and these may be used as an example. Expression vectors containing an SV40 replicon are able to replicate autonomously in COS cells, and these are provided with a transcription promoter, a transcription termination sequence and one or more splicing sites. Expression vectors containing the desired DNA sequence can be used to transform COS cells by various methods, such as, for example, the DEAE-dextran method [Luthman, H. and Magnusson, G. (1983), Nucleic Acids Res. 11, 1295–1308], the calcium phosphate-DNA coprecipitation method [Graham, F. L. and van der Eb, A. J. (1973), Virology 52, 456–457] and the electroporation method [Neumann, E. et al. (1982), EMBO J. 1, 841–845].

If CHO cells are used as the host cells, then it is appropriate to use a vector capable of expressing the neo gene which serves to provide G418 resistance. Suitable vectors carrying this marker include pR SVneo [Sambrook, J. et al. (1989): "Molecular Cloning—A Laboratory Manual", Cold Spring Harbor Laboratory, NY] and pSV2-neo [Southern, P. J. and Berg, P. (1982), J. Mol. Appl. Genet. 1, 327–341]. Transformants can then be selected by their resistance to G418.

The selected transformant can be cultured by conventional methods and, in the case of the second embodiment of the invention, polypeptide is produced both intracellularly and extracellularly. Suitable culture media can be selected from those commonly used, in accordance with the host cells employed. For example, for COS cells, a medium containing blood components, such as fetal bovine serum, can be added as necessary to media such as RPMI-1640 medium or Dulbecco's modified Eagle's medium (DMEM).

Should the practitioner prefer to use insect cells,, then cells derived from *Spodoptera frugiperda* [Smith, G. E. et al. (1983), Mol. Cell. Biol. 3: 2156–2165] may be used.

Suitable yeasts include baker's yeast (*Saccharomyces cerevisiae*) and fission yeast (*Schizosaccharomyces pombe*).

Suitable plant cells include those from *Nicotiana tabacum* and *Oryza sativa*.

It will be appreciated that the hosts enumerated above are standard hosts in the art, and that the skilled person in the art will be able to choose amongst these and other hosts as appropriate.

Suitable expression vectors for vertebrate cells include those which have a promotor located upstream from the gene to be expressed, together with such sites as an RNA splicing site, a polyadenylation site, and a transcription-termination sequence, and further having a replication origin, if required. A suitable example of such an expression vector is pSV2dhfr, which has the SV40 early promotor [Subramani, S. et al. (1981), Mol. Cell. Bio. 1: 854–864].

A suitable expression system for insect cells includes cultured cells of *Spodoptera frugiperda*. Suitable expression vectors have, for example, the Baculovirus Polyhedrin promoter located upstream from the gene to be expressed, together with a polyadenylation site and a portion of the AcMNPV (*Acutographa californica* nuclear polyhedrosis virus) genome required for homologous recombination. One example is pBacPAK8 [Matuura, Y. et al. (1987), J. Gen. Virol. 68: 1233–1250].

For eukaryotic expression, yeast is commonly used, such as baker's yeast (*S. cerevisiae*). Suitable expression vectors for yeast may include the alcohol dehydrogenase promoter [Bennetzen, J. L. and Hall, B. D. (1982), J. Biol. Chem. 257: 3018–3025], the acidic phosphatase promoter [Miyahara, A. et al. (1983), Proc. Natl. Acad. Sci. USA 80, 1–51, or the carboxypeptidase Y promoter [Ichikawa, K. et al. (1993), Biosci. Biotech. Biochem. 57: 1686–1690], for example. In such an instance, the signal peptide sequence from carboxypeptidase Y may also be used, in order to effect secretion to the extracellular space.

Suitable expression vectors for plants include, for example, pBI121 which has a 35S promoter (derived from the early promoter of cauliflower mosaic virus), the polyadenylation sequence of the nopaline synthesis gene from *Agrobacterium tumefaciens*, and the *Agrobacterium tumefaciens* gene transfer sequence [Jefferson, R. A. et al. (1987), EMBO J. 6: 3901–3907]. Such vectors can be introduced into plant cells by such methods as infection with *Agrobacterium tumefaciens* and electroporation.

Plasmid pKK388–1 (manufactured by Clonetech Co.) has a trc promoter and is suitable for use in *Escherichia coli*. This expression vector is able to autonomously replicate in a strain derived from *Escherichia coli* strain K12, such as strain JM109. This vector can easily be introduced into *Escherichia coli* by such well. known methods as are mentioned above. The thus obtained strain can be inoculated into a medium, such as the well known LB medium, and cultured for a while.

The trc promoter can then be activated by adding, for example, isopropyl-β-galactopyranoside (IPTG), to induce the promoter. After further culturing, the expressed protein then can be extracted from the cells by disrupting the cells, such as with a sonicator. If it is desired to produce a protein having Pro at the N-terminus, then it will generally be appropriate to use *Escherichia coli* as the host.

By applying the above description and, if necessary, taking into account the accompanying Examples, a fraction from the culture of suitably transformed cells containing the desired polypeptide can be isolated and purified by known methods, depending on the physical and chemical properties of the polypeptide. Suitable such methods include treatment with a protein precipitant, ultrafiltration, various chromatographies [such as molecular sieve chromatography (gel filtration), adsorption chromatography, ion exchange chromatography, affinity chromatography and high performance liquid chromatography (HPLC)], dialysis and combinations of the above methods.

In order to determine whether the expressed NIa protein has the necessary protease activity, the purified NIa protein may be reacted with a substrate protein containing a cleavage sequence for the protease, such as the expression product of the gene encoding the fusion protein which includes the viral coat protein (the natural substrate of NIa) together with nuclear inclusion b (NIb) [Dougherty, W. G. et al. (1988), EMBO J. 7: 1281–1287]. Such a fusion protein may be isolated from the viral genomic cDNA and inserted into an expression vector. The resulting expression vector is then introduced into a suitable host cell to produce the fusion protein. By treating the resultant fusion protein in known manner, such as with a protein precipitant or by chromatography, the fusion protein can be separated and purified.

The thus separated and purified substrate protein can then be reacted with said protease in a suitable buffer solution at a suitable temperature to recover a reaction product. The recovered reaction product can then be subjected to electrophoresis and to Western blotting using an anti-coat protein antibody to allow the protease activity to be detected as a difference in the mobility of a band. In this method, it is also possible for a a synthetic oligopeptide containing an appropriate cleavage sequence to be used.

The proteolytic activity of the protease of the present invention can be detected without purification. Thus, activity can be measured by connecting the protease gene in sequence and in the same open reading frame, downstream from a promoter, such as the trc promoter, and upstream from a cleavage sequence for the protease. If the protease is active in the expression product, then a band of higher mobility than the fusion protein will be observable by Western blotting.

By recovering the band from the gel in which the cleavage is observed and by analyzing the amino terminal. sequence thereof by conventional methodology, it can be established whether the protein is cleaved at the desired peptide bond.

The protein which it is desired to produce may be produced, for example, as a fusion protein together with a protein such as glutathione S-transferase, and the NIa of the present invention can then be used to cleave the linker sequence in vitro. In one alternative, the desired protein is directly expressed in a host cell as a fusion protein together with said protease and the desired protein is prepared by self-cleavage.

If desired, NIa can easily be produced in a high yield and high purity using the above methods, and the thus obtained recombinant NIa of the present invention can be used as a protease.

If it is desired to chemically synthesize the DNA's of the present invention, then these can be prepared by conventional methodology, such as the phosphite triester method [Hunkapiller, M. et al. (1984), Nature 310: 105–111] or by the chemical synthesis of nucleic acids [Grantham, R. et al. (1981), Nucleic Acids Res. 9: r43–r74]. If desired, partial modification of these nucleotide sequences can be effected by conventional methods, such as by site-specific mutagenesis, using a primer comprising a synthetic oligonucleotide encoding the desired modification [Mark, D. F. et al. (1984), Proc. Natl. Acad. Sci. USA. 81: 5662–5666].

Hybridization, as mentioned above, can be established, for example, by using a probe labeled with [$\alpha$-$^{32}$P]dCTP, for example, in the random primer method (Feinberg, A. P. and Vogelstein, B. (1983) Anal. Biochem. 132: 6–13], or by nick translation [Maniatis, T. et al. (1982), in "Molecular Cloning A Laboratory Manual" Cold Spring Harbor Laboratory, N.Y.]. The DNA is fixed to a solid phase by a conventional method, for example by adsorbing to a nitrocellulose membrane or a nylon membrane, and then heating or using ultraviolet radiation. The solid phase is then typically immersed in a prehybridization solution containing 6×SSC, 5% Denhardt's solution and 0.1% SDS and incubated at 55° C. for 4 hours or longer. Then, the previously prepared probe is added to the prehybridization solution to a final specific activity of 1 ×10$^6$ cpm/ml, and the mixture incubated at 60° C. overnight. Then, the solid phase is washed five times repeatedly with 6×SSC for 5 minutes at room temperature, followed by washing at 57° C. for 20 minutes, and autoradiography is carried out to determine whether the DNA has hybridized or not. It will be appreciated that this is a specific example, and that other methods are equally possible.

The desired protein may be prepared by either an intracellular direct cutting method and an extracellular cutting method.

Intracellular Direct Cutting Method

DNA encoding NIa is connected with DNA encoding the desired protein via a cleavage sequence, preferably Gln-Gly, Gln-Ser or Gln-Ala. The resulting DNA encodes a fusion protein and is inserted into a vector comprising a promoter and a terminator and is used to obtain expression in an appropriate host cell. The resulting, expressed fusion protein self-cleaves through the protease activity, thereby affording a peptide in which Gly, Ser or Ala is attached by a peptide bond at the N-terminus of the protein of interest. A particularly preferred protein for expression is IL-11.

Where it is desired to cleave any residues from the N-terminus of the resulting protein, then this may be done as described above, using aminopeptidase P, for example, to leave an N-terminal Pro residue, should this be desired.

Some expression systems already have aminopeptidase P present. However, if aminopeptidase P is not present, and it is desired to cleave N-terminal amino acid residues in situ, then an expression vector for aminopeptidase P may be introduced into the host cell. Aminopeptidase P is a known protein, and a gene sequence for the enzyme is readily available to those in the art.

When it is desired to obtain a protein which starts with Pro at the N-terminus, then it is generally advantageous to extend culture duration in order to allow the cellular aminopeptidase P to act.

As described above, the N-terminal Pro residue can be removed by the catalytic action of proline iminopeptidase (3.4.11.5), endogenously expressed or expressed by an exogenous expression vector (the enzyme is a known protein, and a gene sequence for the enzyme is readily available to those in the art). Alternatively, the proline residue can be cleaved after recovery from the expression system, such as where the fusion protein is secreted from the cell.

Thus, it can be seen that the present invention permits the production of proteins having any desired N-terminal residue.

Where the sequence of the present invention results in a polypeptide having an Ala N-terminus, then this alanine residue can be removed by the catalytic action of alanine aminopeptidase (3.4.11.14) which, again, is a known enzyme, and wherein the gene sequence is readily available to those skilled in the art. This technique also allows the production of a polypeptide having a freely chosen N-terminal residue.

The desired protein can then be isolated and purified by well known methods.

Extracellular Cutting Method

NIa can be produced by incorporation of suitable DNk into a vector which is then included in a suitable expression system. The resulting NIa expressed by the transformed cell can then purified by use of such as an ion exchange column, a gel filtration column or a reverse phase column. Alternatively, the NIa may be expressed as a fusion protein with another polypeptide, such as glutathione-S-transferase or maltose-binding protein, which can be separated and purified using a glutathione column or a maltose column, respectively. After cutting the purified product with enterokinase or Factor Xa, the NIa can be purified and used.

Meanwhile, the protein precursor is prepared which contains the NIa recognition sequence (cleavage sequence). This may be present in a given place, or the protein may form part of a fusion protein with, for example, glutathione-S-transferase or maltose-binding protein, linked by an appropriate linker (cleavage sequence). Reaction of the precursor with NIa in a suitable buffer solution cleaves the precursor in vitro. If desired, N-terminal amino acid residues can be removed, as described above.

As before, the resulting protein can be isolated and purified by known methods.

In respect of the second embodiment of the present invention, we believe the naturally occurring reducing peptide has the sequence shown in Sequence ID 12, and consists of 526 amino acids, with a valine residue as the N-terminal.

The naturally occurring DNA encoding the peptide has, we believe, the nucleotide sequence 70 to 1647 indicated in sequence ID number 11.

The peptide of the invention is capable of reducing oxidized glutathione and dichloroindophenol. This is an accurate description of the peptide, but is somewhat cumbersome, so that the peptide of the invention will also be referred to herein as the KM31-7 peptide or protein.

The KM31-7 protein originates in the body, or is a mutant or variant thereof, so that there are minimal problems with toxicity and/or antigenicity.

In the second embodiment of the present invention, the polypeptide having the sequence −23 to 526 of sequence ID 12 is believed to be a precursor of the KM31-7 protein. As such, the present invention also encompasses this precursor, as well as mutants and variants thereof, and polynucleotide sequences encoding any of these.

The following discussion is essentially with regard to the second embodiment of the present invention. It will be understood that many of the procedures described above in relation to CYVV NIa are also appropriate to the isolation, cloning and expression of DNA encoding the peptide of the invention. Any differences essentially arise from the fact that CYVV NIa is a plant virus protein, while the peptide of the invention is a mammalian protein. General steps for obtaining an expressed specific polypeptide from mammalian cells by genetic recombination techniques will now be described.

mRNA encoding the KM31-7 peptide can be obtained and reverse-transcribed into ds-DNA by well known methods. Any appropriate mammalian cells, cell lines or tissue can be used as the source of the original mRNA, but we prefer to use the cell line KM-102 derived from human bone marrow stromal cells [Harigaya, K. and Handa, H. (1985), Proc. Natl. Acad. Sci. USA, 82, 3447–3480].

To extract mRNA from mammalian cells, various methods can be used, such as the guanidine thiocyanate hot phenol method or guanidine thiocyanate guanidine hydrochloric acid method, but the guanidine thiocyanate cesium chloride method is generally preferable.

Since the majority of mRNA present in the cytoplasm of eukaryotic cells is known to have a 3' terminal poly A sequence, purification of mammalian mRNA can be effected by adsorption onto an oligo(dT) cellulose column, thereby taking advantage of this characteristic. The eluted mRNA can then be further fractionated by methods such as sucrose density gradient centrifugation.

Confirmation that the mRNA does indeed encode the desired peptide can be achieved by translating the mRNA in a suitable system, such as the *Xenopus laevis* oocyte system, the rabbit reticulocyte system or the wheat germ system (supra).

Measurement of the reducing activity of the expression product can be performed as described below.

i) Determination of Dichloroindophenol Reducing Activity

The methodology for this determination is described by Beinert, H. in "Methods in Enzymology" (1962), 5, 546.

A 50 $\mu$M dichloroindophenol (Sigma) preparation is made up with 20 mM phosphate buffer and 0.5 M NaCl (pH 7.8). 1 ml of this preparation is then placed in a cuvette (SARSTEDT, 10×4×45 mm) and the sample is then added for measurement. 15 $\mu$l of 1 mM NADPH (Boeringer-Mannheim), made up in the same buffer, is added to the cuvette at room temperature to start the reaction. Reductase activity can then be determined by following the decrease in absorption of oxidized dichloroindophenol at 600 nm or by following the decrease in absorption of NADPH at 340 nm.

ii) Determination of Oxidized Glutathione Reducing Activity

The methodology for this assay is described by Nakajima, T. et al. in "New Basic Experimental Methods in Biochemistry (6)—Assay Methods Using Biological Activity", 3–34.

A preparation of 10 mM oxidized glutathione (Boeringer-Mannheim) is made up with 20 mM phosphate buffer and 0.5 M NaCl to a pH of 7.8. 15 µl of this preparation are placed in a cuvette (10×4×4 mm) after the sample has first been placed in the cuvette. 15 µl of 1 mM NADPH pr epared in the same buffer is then added to the cuvette at room temperature to start the reaction. Glutathione reductase activity can then be determined by following the decrease in absorption at 340 nm.

Various methods, as described above, can be used to derive ds-DNA from mRNA. These include the Sl nuclease method, the Land method and the O. Joon Yoo method (supra) but we prefer to use the Okayama-Berg method [Okayama H. and Berg, P. (1982), Mol. Cell. Biol. 2, 161–170] in this instance.

The thus obtained ds-cDNA can then be incorporated into a cloning vector and the resulting recombinant plasmid can be introduced into *Escherichia coli* as described above.

A strain containing the desired DNA encoding the peptide of the invention can be selected by various methods, such as those described above in relation to selecting transformants containing NIa DNA, with any appropriate modifications of procedure. For example, if PCR is used to prepare a probe, then suitable template DNA may either be the cDNA described above, or genomic DNA.

In the second embodiment of the present invention, it is possible to use a primary screen to reduce the number of transformant strains to be tested. The primary screen is possible, because the peptide of the invention is related to the cytokines, so that its mRNA. shares the AUUUA motif common to the mRNA of cytokines [Shaw, G. and Kamen, R. (1986), Cell 46, 659–667]. Thus, a synthetic oligonucleotide probe which is complementary to the AUUUA motif can be used in the primary screen. Screening by assay of the production of exogenous protein in mammalian cells can the n be performed.

DNA encoding the peptide can then be excised from the vector and sequenced in similar fashion to that described above in relation to NIa DNA. Again, as described above, the DNA fragment can then be introduced into an appropriate vector and used to transform a prokaryotic or eukaryotic host, as desired.

The KM31-7 protein may be used either alone or in combination with one or more other therapeutic drugs in the prevention and treatment of conditions caused by, or related to, oxidative stress, or any disease caused by activated oxygen. Such conditions include, but are not limited to, arteriosclerosis, diabetes, ischemic disorders (such as reperfusion disorders, ischemic heart disease, cerebroischemia and ischemic enteritis), edema, vascular hyperpermeability, inflammation, gastric mucosa disorders, acute pancreatitis, Crohn's disease, ulcerative colitis, liver disorders, Paraquat's disease, pulmonary emphysema, chemocarcinogenesis, carcinogenic metastasis, adult respiratory distress syndrome, disseminated intravascular coagulation (DIC), cataracts, premature retinopathy, auto-immune diseases, porphyremia, hemolytic diseases, Mediterranean anemia, Parkinson's disease, Alzheimer's disease, epilepsy, ultraviolet radiation disorders, radioactive disorders, frostbite and burns.

Pharmaceutical compositions of the second embodiment of the present invention comprise a pharmaceutically active amount of the KM31-7 peptide and a pharmaceutically acceptable carrier therefor.

The compositions of the present invention may be administered in various forms, such as by oral administration in the form of tablets, capsules, granules, powders and syrups, or by parenteral administration in the form of injections, infusions and suppositories. Other suitable administration forms will be apparent to those skilled in the art.

In the event that the peptide of the invention is to be administered as an injection or infusion, then a pyrogen-free preparation of the peptide is made up in a pharmaceutically acceptable aqueous solution suitable for parenteral administration. The preparation of the polypeptide solution so as to conform with the requirements of pH, isotonicity and stability is within the technical expertise of those skilled in the art.

Dosage and form of administration can readily be determined by one skilled in the art, taking into account such criteria as patient condition, body weight, sex, age, diet, severity of other infections, administration time and other clinically significant factors. In general, the normal adult oral dose will be in the range of about 0.01 mg to about 1000 mg per day. This amount can be administered in a single dose or as several sub-doses over a period of 24 hours. When the peptide is administered parenterally, about 0.01 mg to about 100 mg per administration can be given by subcutaneous, intramuscular or intravenous injection.

In order to fully characterize the KM31-7 protein, it was important to obtain an antibody that was specific for this protein. Such an antibody would be useful in assaying the function, quantification, purification and tissue distribution of the KM31-7 protein.

Accordingly, a hybridoma producing anti-KM31-7 antibody was obtained by inoculating laboratory animals with the polypeptide produced by *E. coli* transformed by pMAL31-7, preparing a hybridoma of antibody-producing cells together with myeloma cells, followed by screening and cloning the hybridoma. The antibodies produced by the resulting hybridoma were capable of recognizing the polypeptide obtained from serum-free culture supernatant of COS-1 cells transformed with pSRα31-7.

Thus, the prevent invention further provides an antibody, preferably a monoclonal antibody, or an equivalent thereof, which specifically recognizes KM31-7 protein, or a mutant or variant of KM31-7 protein.

The antibody of the present invention is directed against the KM31-7 protein or a mutant or variant thereof. It will be appreciated that the antibody may be polyclonal or monoclonal, but that the monoclonal form is preferred. This is because of the uncertainty generally associated with polyclonal antibodies. For consistency of results, whether for therapy or for purification of KM31-7 protein, for example, it is preferred to use monoclonal antibodies.

The antibodies of the invention may be prepared from any suitable animal. However, problems with antigenicity can arise where the antibody is non-human. In this respect, it is possible to engineer the antibodies to more closely resemble human antibodies. This may be achieved either by chemical or genetic modification by methods well known in the art.

The present invention also envisages anti-idiotypic antibodies, that is, antibodies whose recognition site recognizes the recognition site of the above antibodies. Such anti-idiotypic antibodies can be prepared by administering the original antibody to a suitable animal. It will be appreciated that this process can continue, effectively ad infinitum, with each generation corresponding to either the original or the anti-idiotype. However, it the antibodies are not selected for the correct recognition after each generation, then specificity may effectively be lost. Anti-idiotypic antibodies may be useful, for example, in assaying free anti-KM31-7 antibody.

The present invention also envisages fragments of the antibodies of the invention which are capable of recognizing KM31-7 protein, and molecules carrying the recognition site of such antibodies. Such fragments and molecules are referred to herein as "equivalents" of the antibodies of the invention.

The plasmid pMAL31-7 was used to transform *E. coli*, and the expression product was purified and used to immunize laboratory animals. Spleen cells from the immunized animals were used to prepare a hybridoma by fusion with myeloma cells, and a clone producing anti-KM31-7 monoclonal antibodies was obtained in high concentration and with good stability (this clone was named MKM150-2 and deposited at the Fermentation Research Institute of the Agency of Industrial Science and Technology, Japan, under the deposit number FERM BP-5086). A culture of this clone yields anti-KM31-7 monoclonal antibodies from the culture supernatant.

The resulting anti-KM31-7 monoclonal antibody reacts immunochemically with the fusion protein obtained by introducing and expressing pMAL31-7 in *E. coli*. This antibody also reacts immunochemically with KM31-7 protein obtained from the culture supernatants of mammalian cells transformed with cDNA encoding KM31-7.

In order to produce a monoclonal antibody, the procedures outlined below will generally have to be followed. These consist of:

(a) purification of the biopolymer to be used as the antigen;

(b) immunization of mice by injection of the antigen, and preparing antibody-producing cells at the appropriate time from the spleen by sampling and assaying blood;

(c) preparation of myeloma cells;

(d) fusing spleen and myeloma cells;

(e) screening to select the hybridoma group that produces the desired antibodies;

(f) preparing a single clone (cloning);

(g) culturing the hybridoma for large-scale production of monoclonal antibody, or husbanding mice infected with the hybridoma, as the case may be; and (h) assaying the physiological activity or properties as a labelling reagent of the resulting monoclonal antibody.

The production of anti-KM31-7 monoclonal antibodies will now be described with reference to the procedures outlined above. It will be appreciated that it is not necessary to follow precisely the following description, and that it is possible to use any suitable procedure. For example, it is possible to use antibody-producing cells and myelomas other than spleen cells as well as antibody-producing cells and myelomas of other mammals. The following procedure represents the currently preferred method for obtaining anti-KM31-7 monoclonal antibodies.

(a) Antigen Purification

The fusion protein obtained by expressing pMAL31-7 in *E. coli* and purifying the product is an effective antigen. A culture of *E. coli* TB-1 transformed with pMAL31-7 was induced with isopropyl β-D-thiogalactopyranoside (IPTG). The expressed fusion protein was then purified by affinity chromatography using an amylose resin column (New England BioLabs). KM31-7 protein purified from the serum-free culture supernatant of COS-1 cells transformed with pSRα31-7 is also an effective antigen.

(b) Preparation of Antibody-Producing Cells

The purified fusion protein obtained in (a) is mixed with Freund's complete or incomplete adjuvant, or an adjuvant such as potash alum, and laboratory animals are then immunized with the resulting vaccine. BALB/c mice are a preferred choice for use as the laboratory animals, because the majority of useful myelomas derived from mice are derived from BALB/c mice. Moreover, the characteristics of these mice have been studied in a great amount of detail. Furthermore, if both the antibody-producing cells and the myeloma are from BALB/c mice, then the resulting hybridoma can be grown in the abdominal cavity of BALB/c mice. Thus, the use of BALB/c mice offers the advantage of enabling monoclonal antibodies to be easily obtained from ascites without having to employ complex procedures. Nevertheless, the present invention is not limited to the use of BALB/c mice.

The antigen may be administered in any suitable form, such as by subcutaneous injection, intraperitoneal injection, intravenous injection, intracutaneous injection or intramuscular injection, and we prefer subcutaneous injection or intraperitoneal injection.

Immunization may be performed once or on a plurality of occasions with suitable intervals. The preferred regimen is to immunize and then boost, one or more times, at intervals of from 1 to 5 weeks. The effectiveness of later procedures can be improved if the antibody titer to said antigen in the serum of the immunized animals is regularly assayed, and animals having a sufficiently high antibody titer are used to provide antibody-producing cells. Antibody-producing cells for subsequent fusion are preferably isolated front an animal 3 to 5 days after the final immunization.

Methods for assaying antibody titer include, for example, various known techniques, such as radioisotope immunoassay (RIA), enzyme-linked immunosorbent assay (ELISA), the fluorescent antibody technique and passive hemagglutination, but RIA and ELISA are preferable for their sensitivity, speed, accuracy and potential for automation.

A suitable form of ELISA is as follows. Antigen is adsorbed onto a solid phase and then the solid phase surface is exposed to a protein unrelated to the antigen, such as bovine serum albumin (BSA), to block any areas of the surface which have no adsorbed antigen. The solid phase is then washed, after which it is exposed to a serially diluted sample of the primary antibody (e.g. mouse serum). Any anti-KM31-7 antibody in the sample binds to the antigen. After washing, secondary, enzyme-linked, anti-mouse-antibody is added and is allowed to bind to bound mouse antibody. After washing, enzyme substrate is added and the antibody titer can then be calculated by measuring a parameter, such as color change, caused by decomposition of the substrate.

(c) Myeloma Cell Preparation

Established mouse cell lines are preferably used as the source of myeloma cells. Suitable examples of such cell lines include myeloma cell line P3-X63 Ag8-U1 (P3-U1) from 8-azaguanine resistant mice of BALB/c origin [Current Topics in Microbiology and Immunology, 81, 1–7 (1978)], P3-NSI/1-Ag4.1 (NS-1) [European J. Immunology, 6, 511–519 (1976)], SP2/O-Ag14 (SP-2) [Nature, 276, 269–270 (1978)], P3-X63-Ag8.653 (653) [J. Immunology, 123, 1548–1550 (1979)] and P3-X63-Ag8 (X63) [Nature 256, 495–497 (1975)]. These cell lines may be subcultured in suitable media, such as 8-azaguanine medium (RPMI-1640 medium containing 8-azaguanine, 1.5 mM glutamine, $5\times10^{-5}$ M 2-mercaptoethanol, 10 µg/ml gentamycin and 10% fetal calf serum), Iscove's Modified. Dulbecco's Medium (IMDM) or Dulbecco's Modified Eagle's Medium (DMEM). The cell count is elevated to at least $2\times10^7$, on the day of fusion, by subculturing with normal medium, also known as complete GIT [5.5 ml of MEM non-essential amino acids solution (NEAA, Gibco), 27.5 ml of NCTC109 (Gibco), 6 ml of penicillin-streptomycin solution (Sigma) and 11 ml of glutamine 200 mM solution (Sigma) in 500 ml of GIT medium (Wako Pure Chemical Industry)], 3 to 4 days before cell fusion.

(d) Cell Fusion

The antibody-producing cells are plasma cells and their precursor lymphocytes. These may be obtained from any appropriate site of an individual animal, such as the spleen, lymph nodes, peripheral blood or any suitable combination of these. However, spleen cells are most commonly used.

Antibody-producing cells are harvested, 3 to 5 days after the final immunization, from mice having at least the prescribed antibody titer. The resulting antibody-producing cells are then fused with the myeloma cells obtained in (c) above. The process most commonly used at present is to fuse the spleen cells with the myeloma cells using polyethylene glycol, owing to the relatively low level of cellular toxicity and ease of manipulation of this compound. This process is performed as follows.

Spleen cells and myeloma cells are thoroughly washed with medium or phosphate buffered saline (PBS), mixed so that the ratio of spleen cells to myeloma cells becomes roughly between 5 and 10:1, and then subjected to centrifugal separation. The supernatant is discarded and the clump of cells is thoroughly broken up, and the a a mixed solution of polyethylene glycol (PEG, molecular weight: 1000 to 4000) is added with stirring. After several minutes, the cells are subjected to centrifugal separation. The supernatant is again discarded, and the settled cells are suspended in a suitable amount of complete GIT containing 5 to 10 ng/ml of mouse IL-6 and then transferred to the wells of a culture plate. Once cell growth has been confirmed in each well, the medium is replaced with HAT medium (complete GIT containing 5 to 10 ng/ml of mouse IL-6, $10^{-6}$ to $10^{-3}$ M hypoxanthine, $10^{-8}$ to $10^{-7}$ M aminopterin and $10^{-6}$ to $10^{-4}$ M thymidine).

(e) Selection of Hybridoma Groups

The culture plate is incubated in a $CO_2$ incubator at 35 to 40° C. for 10 to 14 days. During this time, fresh HAT medium equivalent to half the amount of medium is added every 1 to 3 days.

The myeloma cells are from an 8-azaguanine-resistant cell line and both the myeloma cells and hybridomas consisting only of myeloma cells cannot survive in HAT medium. However, hybridomas comprising an antibody-producing cell part, including hybridomas of antibody-producing cells and myeloma cells, can survive. Hybridomas consisting only of antibody-producing cells are mortal, so that hybridomas consisting of both myeloma and antibody-producing cells can be selected by culturing in HAT medium.

HAT medium is replaced with HT medium (wherein aminopterin has been omitted from HAT medium) in those wells in which hybridomas which have been observed to develop colonies. A portion of the culture supernatant is then removed and anti-KM31-7 antibody titer is assayed by, for example, ELISA.

The above process is described with respect to an 8-azaguanine-resistant cell line, but other cell lines can also be used, provided that they permit the selection of hybridomas. The composition of the medium used naturally also changes in such cases.

(f) Cloning

Hybridomas from (e) which have been determined to produce anti-KM31-7 specific antibody are transferred to a different plate for cloning. Various cloning methods can be used, such as the seeding method (wherein the hybridomas are subjected to limiting dilution analysis so that each well contains only one hybridoma), the soft agar method (wherein seeded colonies are taken in soft agar medium), the seeding method (wherein a single cell is removed by a micro-manipulator), and the sorter cloning method (wherein individual cells are separated by a cell sorter). Limiting dilution analysis is used most frequently due to its simplicity.

Cloning, such as by limiting dilution analysis, is repeated 2 to 4 times for those wells in which an antibody titer continues to be observed. A clone consistently exhibiting the production of anti-KM31-7 antibody is selected as the hybridoma of choice.

(g) Preparation of Monoclonal Antibody by Hybridoma Culture

The hybridoma of choice from (f) is then cultured in ordinary medium. Large-volume culture is performed by rotary culturing using either a large culture bottle or a spinner. Anti-KM31-7 monoclonal antibodies can be obtained by subjecting the cell supernatant to gel filtration, and then collecting and purifying the IgG fraction. In addition, the hybridoma can also be grown in the abdominal cavity of the same strain of mouse (e.g. the above-mentioned BALB/c mice) or Nu/Nu mice, for example. A simple method for performing this step is to use a monoclonal antibody preparation kit (e.g., MAbTrap GII of Pharmacia).

(h) Identification of Monoclonal Antibody

Determination of the isotype and subclass of the monoclonal antibody obtained in (g) can be performed as described below. Examples of identification techniques which can be used include the Ouchterlony method, ELISA and RIA. Although the Ouchterlony method is simple, there is a drawback, in that the monoclonal antibody must be concentrated in cases in where concentration is excessively low.

If either ELISA or RIA is used, the culture supernatant can be directly exposed to a solid phase on which antigen has been adsorbed. Secondary antibodies specific for each type of IgG subclass can then be used to identify subclass type. In the alternative, an isotyping kit (for example, the mouse monoclonal antibody isotyping kit of Amersham). can be used. Protein quantification can be performed by the Folin-Lowry method or by measuring absorbance at 280 nm [1.4 ($OD_{280}$)=1 mg/ml of immunoglobulin].

In the accompanying Examples, the monoclonal antibody obtained from the hybridoma designated MKM150-2 was determined to be of the IgG class isotype and was identified as belonging to the IgG1 subclass.

The monoclonal antibody obtained in accordance with the present invention has a high specificity for KM31-7 protein. Moreover, since monoclonal antibody is obtained consistently and in good quantities by culturing the above-mentioned hybridoma, it can be used for the isolation and purification of KM31-7 protein, and the isolation and purification of KM31-7 protein with said monoclonal antibody by immune precipitation using an antigen-antibody reaction forms a part of the present invention.

The present invention will now be illustrated with reference to the accompanying, non-limiting Examples. All solutions are aqueous and prepared from deionized water, and those expressed in the form of percentages are w/v, unless otherwise specified. If methods are not specified, then they can be found in "Molecular Cloning—A Laboratory Manual" [second edition, Sambrook, J., Fritsch, E. F. and Maniatis, T. (1989), Cold Spring Harbor Laboratory Press]. Methods of preparation of solutions and other media are given in the later section entitled "Media" where they are not given in the Examples. Methods referred to in the Examples without techniques should be construed in the context of preceding Examples.

A) Source Material for CYVV

A leaf infected with the clover yellow vein virus and which had been stored in the frozen state [CYVV-isolate No. 30: Uyeda, I. et al. (1975), Ann. Phytopath. Soc. Japan 41: 192–203] was milled with 10 volumes of inoculation buffer.

Propagation of CYVV was carried out using *Vicia faba* cultivar Wase-Soramame which had developed a second adult leaf. An adult leaf was sprayed with carborundum (400 mesh) and was then inoculated with the liquid obtained above using a glass spatula. About eight to ten days after the inoculation, the inoculated leaf had developed a mesh-like mosaic condition. This leaf was removed and used as a source of CYVV.

B) Purification of Virus

Leaves isolated in A) above were chopped with a mincer containing 3 volumes of extraction buffer. After chopping, the leaves were further ground in a mortar and pestle. The resulting preparation was stirred slowly at room temperature for 1 hour using a motor equipped with a stainless steel agitating blade. The liquid preparation was then squeezed out through a double layer of gauze.

All of the subsequent procedures were carried out at 4° C.

The crude liquid was mixed with a half volume of chloroform and the mixture was blended in a Waring blender, after which the preparation was centrifuged at 6,000×g for 15 minutes. Following centrifugation, the aqueous layer was collected, and polyethylene glycol (PEG #6,000) was added to this fraction to a final concentration of 4% v/v.

The resulting mixture was stirred over ice for 1 hour and allowed to stand on ice for another 1 hour. The thus obtained liquid was subjected to centrifugation at 6,000×g for 15 minutes, and the precipitate was recovered as the virus-containing fraction. This precipitate was suspended in 50 ml of a 10 mM phosphate buffer (pH 7.4) containing 0.5 M urea and then mixed with an equal volume of carbon tetrachloride, and the resulting preparation was stirred vigorously for 5 minutes, after which time the preparation was subjected to centrifugation at 3,000×g for 10 minutes. The aqueous phase was then ultracentrifuged at 4° C. at 30,000 rpm for 90 minutes using an Hitachi RP-30 rotor. The resulting pellet was recovered as the virus-containing fraction.

The pellet was suspended in 10 mM phosphate buffer containing 1% Triton X100 (pH 7.4) and this suspension was subjected to centrifugation at 4° C. at 8,000×g for 1 minute. The resulting supernatant was layered on a graduated 10 to 40% sucrose density gradient column tube (40%: 10 ml, 30%: 10 ml, 20%: 10 ml, 10%: 10 ml; and which had been allowed to stand overnight at 4° C.) which, had previously been prepared with 10 mM phosphate buffer (pH 7.4). Once the tube had been layered with the supernatant, it was subjected to ultracentrifugation at 4° C. at 23,000 rpm for 120 minutes in a Hitachi PRS25 rotor.

After centrifugation, the sucrose density gradient column tube was fractionated using a fractionater (Model UA-2: manufactured by ISCO Co.) equipped with an $OD_{260nm}$ detector. The fractions having a sucrose density of about 20 to 30% and absorbing at $OD_{260nm}$ were taken as the virus-containing fraction.

The recovered virus fraction was diluted 2-fold with 10 mM phosphate buffer (pH 7.4) and subjected to centrifugation at 4° C. at 40,000 rpm for 90 minutes using a Hitachi RP-65 rotor. The resulting precipitate was resuspended in 10 mM phosphate buffer (pH 7.4) to yield a purified virus solution.

C) Isolation of Viral RNA

The genomic RNA of CYVV comprises about 10,000 bases and is polyadenylated at its 3'-terminus. The combination of length and polyadenylation make it difficult to extract the full-length RNA without any loss when using either the conventional phenol/sodium dodecyl sulfate method or the guanidinium thiocyanate method. Accordingly, the viral genomic RNA was prepared by the alkaline sucrose density gradient centrifugation method.

500 µl of the virus solution (which we had calculated to contain 2 mg of the virus on the basis that 1 mg/ml of virus has an $OD_{260nm}$ of 2.5) was added to 500 µl of degradation solution and the mixture was allowed to stand at room temperature for 20 minutes. After this time, the mixture was layered over a 0% to 33.4% sucrose density gradient column tube (33.4%: 1.4 ml, 30.4%: 7.6 ml, 27%: 7.0 ml, 23%: 6.3 ml, 18.7%: 5 ml, 12%: 3.2 ml, 0%: 2.7 ml; and which had been allowed to stand at 4° C. overnight) which had been prepared with 1×SSC. The buffer used was also 1×SSC, and the layered tube was then subjected to ultracentrifugation in a Hitachi RPS-27 rotor at 15° C. at 24,000 rpm for 9 hours. After this time, the bottom of the tube was punctured in order to fractionate the sucrose density gradient. The viral genomic RNA fraction was identified by measuring the absorbance of each fraction at 260 nm. Sedimentation of the viral genomic RNA occurred at a sucrose concentration of about 20 to 30%. Genomic RNA was obtained in a yield of about 25 µg.

D) Synthesis of Viral cDNA cDNA was synthesized using the genomic RNA prepared in C) above as a template. cDNA synthesis was carried out using the cDNA Synthesis System Plus (manufactured by Amersham). The resulting cDNA was purified on a Sephadex G50 column (registered trademark, manufactured by Pharmacia), and a poly C chain was added to the 5' terminus of the purified cDNA using dCTP and terminal deoxynucleotide transferase (manufactured by Bethesda Research Laboratories). A preparation of plasmid pBR322 (manufactured by Bethesda Research Laboratories) was made by digesting the plasmid with the restriction enzyme PstI and then adding a 3' poly G chain at both termini. The cDNA was then added to this preparation, and the mixture was incubated at 65° C. for 5 minutes, after which time it was incubated at 57° C. for 2 hours. The resulting mixture was then gradually cooled to allow annealing of the poly C chain of the cDNA with the poly G chain of the plasmid.

E) Transformation

*Escherichia coli* strain HB 101 was transformed with the novel plasmid prepared in D) above by the calcium chloride method. A seed culture of *E. coli* strain HB 101 was prepared by shaking overnight in liquid LB medium. 0.5 ml of this seed culture was used to inoculate 50 ml of fresh liquid LB medium and the inoculum was cultured with shaking at 37° C. until an $OD_{550nm}$ of 0.5 was obtained. Bacterial cells were recovered by centrifugation at 4° C. at 5,000×g for 5 minutes and the resulting pellet was gently suspended in 25 ml of Tris-calcium buffer and allowed to stand on ice for 5 minutes. The resulting suspension was centrifuged again at 4,000×g for 4 minutes and the pellet was suspended in 5 ml of Tris-calcium buffer and allowed to stand on ice for 2 hours to yield competent cells.

100 µl of the novel plasmid obtained in D) above were added to 200 µl of the competent cells obtained above, and the mixture was allowed to stand on ice for 30 minutes. After this time, the mixture was incubated at 42° C. for 2 minutes and then 1 ml of liquid LB medium was added, and the resulting mixture was cultured with shaking at 37° C. for a further one hour. The resulting mixture was spread onto solid LB medium containing 12.5 μg/ml tetracycline hydrochloride and 1.5% w/w agar. The cells were cultured at 37° C. overnight to provide a cDNA clone library.

F) Preparation and Selection of Plasmid pNS51

The cDNA recombinant plasmid library was analyzed using the alkaline-SDS method. In more detail, the method was as follows.

2 ml of liquid LB medium was inoculated with a colony of bacteria resistant to tetracycline but sensitive to ampicillin, obtained from the solid LB culture of E) above, and the resulting suspension was cultured with shaking at 37° C. overnight. Cells were recovered by centrifugation at 10,000×g and suspended in 70 μl of lysis buffer containing a further 16 μl of lysozyme solution (10 mg/ml). After agitating for 5 seconds to create a suspension, the suspension was allowed to stand at room temperature for 5 minutes. After this time, 160 μl of alkaline-SDS solution were added to the suspension and the resulting mixture was first mixed by inverting the tube several times and then allowed to stand on ice for 5 minutes. 120 μl of 5 M potassium acetate were next added to the mixture which was then again allowed to stand on ice for 5 minutes. After this time, the mixture was centrifuged at 10,000×g for 5 minutes at 4° C.

After centrifugation, the supernatant was transferred to a fresh tube, and 250 μl of isopropanol was further added to the tube and the resulting mixture was allowed to stand on ice for 30 minutes. After this time, the mixture was again centrifuged at 10,000×g for 5 minutes, and the resulting pellet was dissolved in 100 μl of TE buffer [10 mM Tris, 1 mM EDTA (pH 8.0)]. Phenol extraction was then performed by adding an equal amount of phenol/chloroform/isoamyl alcohol (25:24:1) to the resulting mixture with vigorous mixing, and centrifuging the mixture at 10,000×g for 5 minutes at 4° C. (hereinafter, this procedure is referred to as phenol extraction).

100 μl of the aqueous layer obtained from the centrifugation was mixed with 10 μl of 3 M sodium acetate (pH 5.2) and 250 μl of ethanol, and the resulting mixture was allowed to stand on dry ice for 10 minutes, followed by centrifugation at 10,000×g for 5 minutes to recover the nucleic acid fraction (hereinafter, this procedure, using the same relative volumes of supernatant, ethanol and sodium acetate solution, is referred to as ethanol precipitation).

The resulting pellet was suspended in 50 μl of a solution of RNase A (10 μg/ml in TE buffer) and then incubated at 37° C. for 1 hour. After this time, 30 μl of a solution of polyethylene glycol (2.5 M sodium chloride, 20% polyethylene glycol #8,000) was added to the incubated suspension, and the mixture was allowed to stand on ice for 1 hour. After this time, the mixture was centrifuged at 10,000×g for 5 minutes at 4° C. to recover the DNA fraction as a pellet, and ethanol precipitation was performed twice more to yield purified plasmid DNA.

The purified plasmid DNA was cleaved with restriction enzyme PstI and subjected to 1% agarose gel electrophoresis using TBE solution. After electrophoresis, the gel was subjected to Southern blot hybridization [Southern, E. M. (1975), J. Mol. Biol. 89: 503–517]. More specifically, the gel was shaken in denaturation solution for 40 minutes, and transferred to and shaken in neutralization buffer for 2 hours.

After shaking, the gel was transferred onto a polyurethane ester sponge containing 20×SSC to transfer the DNA to a piece of Hybond-N membrane (registered trademark of Amersham) situated on the sponge. After the DNA had been allowed to transfer to the Hybond-N membrane, the membrane was shaken in 1×SSC for 10 minutes and then dried at 80° C. for 1 hour to fix the DNA. The membrane was then placed in prehybridization solution [5 ml of formamide, 1 ml of 50×Denhardt's solution, 2.5 ml of 20×SSC, 100 μl of yeast tRNA (50 mg/ml), 100 μl of 10% SDS and 1.3 ml of redistilled water] and incubated at 50° C. for 3 hours.

Viral genomic RNA which had been cleaved with $Mg^{2+}$ was used as a probe. More particularly, 4 μl of 5×denaturation buffer was added to 16 μl of the solution obtained in C) above containing 1 μg viral RNA, and the mixture was incubated at 37° C. for 3 hours. 5 μl of denatured RNA solution containing 100 ng of RNA (calculated on the basis that 1 mg/ml of RNA has an $OD_{260}$ of 20) was recovered by ethanol precipitation followed by heating at 70° C. for 5 minutes and then quenching on ice.

4 μl of 5×labelling buffer, 1 μl of 3.3 mM [γ-$^{32}$P] ATP (0.37 MBq), and 10 μl of redistilled water were added to the denatured RNA solution. 20 U of T4 polynucleotide kinase solution [manufactured by Takara Shuzo] were then added to the mixture, followed by incubation at 37° C. for 30 minutes. Unincorporated [γ-$^{32}$P] ATP was removed by repeating ethanol precipitation five times.

The resulting labelled probe was added to hybridization solution [5 ml of formamide, 2 ml of 50% dextran sulfate, 200 μl of 50×Denhardt's solution, 2.5 ml of 20×SSC, 50 μl of yeast tRNA (50 mg/ml), 100 μl of 10% SDS, 1.3 ml of redistilled water] to a final concentration of $5\times10^5$ cpm/ml, and the Hybond-N membrane obtained above was transferred to this solution and subjected to hybridization by incubation at 50° C. overnight, followed by washing with shaking at 60° C. with 2×SSC containing 0.1% sodium dodecyl sulfate (SDS). This procedure was repeated three times, and the Hybond-N membrane was then further washed with 0.1×SSC containing 0.1% SDS with shaking at room temperature for 1 hour, and then dried.

Autoradiography revealed a plasmid which we designated pNS51 which had an insertion fragment comprising about 6,500 base pairs (bp) which had hybridized with the viral genomic RNA.

G) Sequence Determination of DNS51 Insert

In order to prepare a restriction map of the cDNA cloned in pNS51, the plasmid was digested with each of the restriction enzymes; BamHI, EcoRI, Hind III, KpnI, NcoI, PstI, SalI, SphI, SacI, SmaI, XhoI, XbaI, and pairs thereof. The resulting map is shown in FIG. 1.

Subsequently, each of the fragments obtained by digestion with the restriction enzymes SalI and PstI was inserted into M13mp19 RF DNA. This was done by digesting pNS51 with the restriction enzymes PstI and SalI and running the cleavage products on a 5% polyacrylamide electrophoresis gel using 1×TBE. After electrophoresis, the gel was stained with 1 μg/ml of ethidium bromide in order to be able to identify the bands under UV light. Strips of the gel containing each DNA band were excised with a razor and subjected to electroelution with an electroeluter (manufactured by Amicon) equipped with Centricon-30 (manufactured by Amicon).

Each fragment was then inserted, using a DNA ligation kit [manufactured by Takara Shuzo], into M13mp19 which had previously been digested either with SalI only, or with both of PstI and SalI, and which had then been treated with alkaline phosphatase.

The resulting recombinant M13mp19 RF-DNA (wherein the fragments had been inserted using T4 DNA ligase) was introduced into E. coli strain JM109 using the rubidium chloride method. A single colony of strain JM109 which had been cultured on M9 minimum agar medium was inoculated into and cultured in liquid SOB medium with shaking overnight. 0.6 ml of this overnight culture was inoculated into 50 ml of fresh liquid SOB medium and cultured with shaking at 37° C. until the $OD_{600nm}$ reached 0.5. The cells were then recovered by centrifugation at 5,000×g at 4° C. for 10 minutes and the pellet was gently suspended in 25 ml of TFB1 buffer and allowed to stand on ice for 20 minutes.

The suspension was again centrifuged at 3,000×g for 5 minutes, and the pellet was suspended in 2 ml of TFB2 buffer and then allowed to stand on ice for 20 minutes to provide competent cells.

The recombinant M13mp19 RF-DNA obtained above was used in amounts of between 1 and 10 µl after ligation and mixed with 100 µl of the competent cells and allowed to stand on ice for 1 hour. After this time, the mixture was incubated at 42° C. for 1.5 minutes and then 500 µl of liquid SOC medium was added to the mixture which was cultured with shaking at 37° C. for a further 1 hour.

2×YT medium containing 0.8% agar, 30 µl of 100 mM IPTG, 10 µl of 10% 5-bromo-4-chloro-3-indolyl-↓-galactoside (X-gal) and 100 µl of an indicator bacteria (an overnight culture of strain JM109 cultured with shaking in 2×YT medium at 37° C.) were added to the resulting culture with shaking, and the mixture was poured onto solid 2×YT medium containing 1.2% agar. After the mixture had solidified, it was cultured at 37° C. overnight. Recombinant phages subsequently showed as white plaques.

Each of the resulting white plaques was inoculated into liquid 2×YT medium containing the indicator bacteria in an amount of 1/100, and this was cultured with shaking at 37° C. overnight. After centrifugation at 10,000×g for 1 minute, the supernatant was frozen or stored at 4° C. as a phage solution, and the cell pellet was processed in a standard procedure for preparing a plasmid to recover RF double-stranded DNA (hereinafter, abbreviated as RF-DNA), which is a replication intermediate of the phage. The presence of an insertion fragment was confirmed by digestion with a restriction enzyme.

Thus, 51SS/M13mp19 (i.e. M13mp19 containing a SalI/SalI fragment which, in turn, is a portion of 51PS5'/M13mp19 genome containing a PstI-SalI fragment from the 5' region of the CYVV genome) was obtained. RF-DNA's were purified from these phage clones by alkaline-SDS and cesium chloride density gradient centrifugation in accordance with standard procedures.

5 μg of the resulting purified DNA was first cleaved with BamHI to obtain a 5' sticky end, and then cleaved further with KpnI to obtain a 3' sticky end. Next, in accordance with the protocol accompanying the Erase-a-base system (manufactured by Promega), exonuclease was added for the stepwise deletion of bases from the 5' sticky end of each cDNA linearized plasmid. Treatment with exonuclease was continued for 10 minutes, and samples were removed at different times between 1 and 10 minutes. Since the vector has a 3' sticky end, it is not attacked by the exonuclease. The various samples obtained over the period of 1 to 10 minutes were then blunt-ended by treatment with S1 nuclease and ligated into a circular form using T4 DNA ligase.

The resulting, circular, recombinant M13mp19 RF-DNA was introduced into *E. coli* strain JM 109 using the rubidium chloride method described above. Accordingly, recombinant phages having variable length cDNA inserts were obtained as a white plaques.

RF-DNA was extracted from the recombinant phage subclones obtained above by conventional means to select clones having inserts of different length. The selected clones were separately cultured by inoculation into liquid 2×YT medium containing an indicator strain of *E. coli* and were cultured with shaking at 37° C. overnight. After this time, 1.5 ml of each culture was centrifuged at 4° C. at 10,000×g for 5 minutes. One ml of the supernatant was transferred to a fresh tube and 250 μl of a 20% polyethylene glycol aqueous solution (20% polyethylene glycol #8000, 2.5 M sodium chloride) was then added to the tube with mixing and then allowed to stand on ice for 30 minutes. The mixture was subsequently centrifuged at 10,000×g for 5 minutes at 4° C., and the resulting pellet was suspended in 100 μl of TE buffer. Single stranded DNA (hereinafter abbreviated as ssDNA) phage genomes were then recovered from each preparation by phenol extraction and ethanol precipitation as before.

Nucleotide sequencing of each of the subclones obtained above was then performed by the dideoxy chain termination procedure, using the ssDNA as a template. More specifically, the phage ssDNA was labeled with [α-$^{32}$P]dCTP (220 TBq/mmol, manufactured by Amersham) using the 7-deaza-sequenase version 2.0 dCTP kit (manufactured by USB). The resulting reaction product was run on a 5% polyacrylamide electrophoresis gel containing 8 M urea and using 1×TBE as the buffer. The gel was dried, and the nucleotide sequence was then determined by autoradiography.

By analyzing the nucleotide sequences of the 5'-PstI-SalI fragment and the M-SalI-SalI fragment of pNS51, we were able to determine a total of 3,839 bases.

As a result of the search for an open reading frame (hereinafter abbreviated as ORF) in the sequence obtained above, a single ORF for a polypeptide was detected on the+sense strand of the viral genome. The polypeptide sequence encoded in the ORF was then determined. A homology search comparing this polypeptide sequence with known sequences using GeneBank revealed homology with TEV-HAT.

It is known that viruses such as TEV, plum pox virus or poliovirus (an animal virus) mature through the action of a protease, and that the protease generally cleaves a peptide bond containing a Gln-Ala, Gln-Ser or Gln-Gly link [Willink J. and van Kammen, A. (1988), Arch. Virol. 98: 1–26]. We were also able to detect three cleavage sequences in the deduced polypeptide sequence, as a result of analysis of the cleavage site(s) of the coat protein of CYVV-No. 30 [Uyeda, I. et al. (1991), Intervirology 32: 234–245]. From one of these cleavage sites, a polypeptide of from Gly at position 4 to Gln at position 437 of the amino acid sequence was determined to be Nuclear Inclusion a from CYVV.

H) Preparation of a CYVV-NIa/IL-11 Fusion Protein

The DNA identified in G) above as coding for CYVV NIa was tandemly linked, in-frame, at its 3' end to DNA encoding human interleukin 11 (IL-11), via a linking sequence encoding Gln-Ala.

The following were examined:

first, whether or not the DNA identified in G) above encodes an NIa having proteolytic activity;

second, whether or not the protease cuts the desired amino acid sequence;

third, whether or not the protease activity of the NIa is still exhibited when the NIa is part of a fusion protein together with a desired heterologous protein in a manner similar to that existing in a virus-infected cell; and fourth, whether or not any heterologous protein obtained through the cleavage of such a fusion protein maintains integrity, structure and function.

Since the NIa itself is produced by excision from a viral precursor polypeptide, the NIa cistron has no initiation codon. Therefore, it is necessary to add an initiation codon, ATG, to the 5' terminus of the NIa gene. The 3' terminus of the NIa gene must also be connected with the 5' terminus of the IL-11 gene within the same ORF. In order to solve these problems, the NIa was modified using the polymerase chain reaction (PCR) technique by utilizing a XhoI cleavage site present in the center of the NIa gene.

In order to add the initiation codon ATG and a recognition site for the restriction enzyme NcoI suitable for cloning to the 5' terminus of NIa (NIa5'), PCR primers were prepared. The sequences prepared were 5'GTCCATGGGGAAAAG-TAAGAGAACA3' (referred to as NSATG; sequence ID number: 3) and 5'ACTCTGAGACCGTGCTCGAG3' (referred to as NSX1; sequence ID number: 4).

0.8 µl of a dNTP solution (25 mM each of DATP, dTTP, dCTP and dGTP), 10×Taq buffer (manufactured by Promega) and 1 µg of each of the resulting primers were added to 1 µg of plasmid pNS51 DNA, and the mixture was made up to 100 µl with redistilled water. 5 U of DNA polymerase made up in 10×Taq buffer were added to effect PCR. For the PCR program, a cycle of 92° C. for 1 minute, 37° C. for 1 minute and 72° C. for 2 minutes was repeated 20 times followed by a single cycle of 92° C. for 1 minute, 37° C. for 1 minute and 72° C. for 30 minutes.

The resulting amplified DNA was subjected to phenol extraction and ethanol precipitation, and then run on a 5% polyacrylamide electrophoresis gel. One band containing DNA was detected by ethidium bromide staining, and this band was excised from the gel and subjected to electroelution with a Centreluter (manufactured by Amicon) equipped with Centricon-30 (manufactured by Amicon). After the elution, the eluteci DNA fragment was concentrated and recovered by centrifugation at 7,500×g using Centricon (Amicon) at 4° C. for 45 minutes. The resulting DNA concentrate was further purified by phenol extraction and ethanol precipitation.

Figure 2:
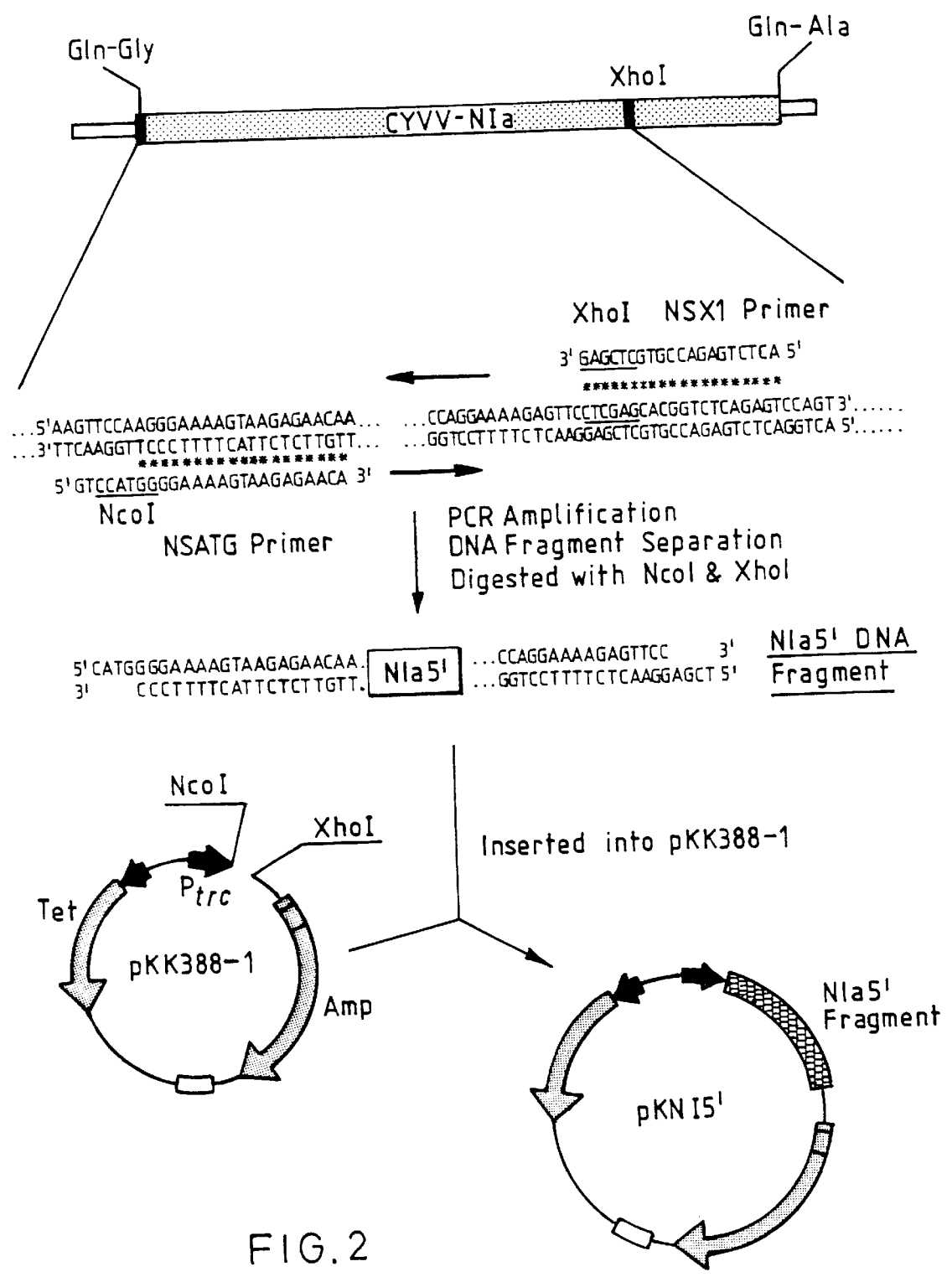

Separately, 1 µg of plasmid pKK388-1 (manufactured by Clonetech) in which a SacI recognition site had been replaced with a recognition site for XhoI, was cleaved with the restriction enzymes NcoI and XhoI and dephosphorylated with Calf Intestine Alkaline Phosphatase [hereinafter abbreviated as CIAP; manufactured by Takara Shuzo]. The resulting DNA was ligated by means of a ligation kit (manufactured by Takara Shuzo) with 100 ng of pKX388-1 which had also been cleaved with NcoI and XhoI and dephosphorylated as above, and the recombinant DNA thus obtained was cloned. into E. coli JM 109. Plasmid pKNI5' which had an insertion in the normal orientation downstream from the trc promoter of pKK388-1 was thereby obtained (FIG. 2).

Plasmid pCD20-2 [Kawashima, I. et al. (1991), FEBS L. 283: 199–202] contains cDNA coding for an IL-11 precursor (Pre-IL-11) and having a secretion signal sequence. This plasmid was cleaved with the restriction enzymes BamHI and ApaI, and a region having both the IL-11 precursor (Pre-IL-11) and SV40 promoter was excised. The fragment was ligated into the BamHI and ApaI sites of pBLUE-SCRIPT II SK+ and then again cleaved with the restriction enzymes XhoI and KpnI, resulting in a gene which codes for a protein devoid of the N-terminus of mature IL-11 (Mat-IL-11).

Figure 3:
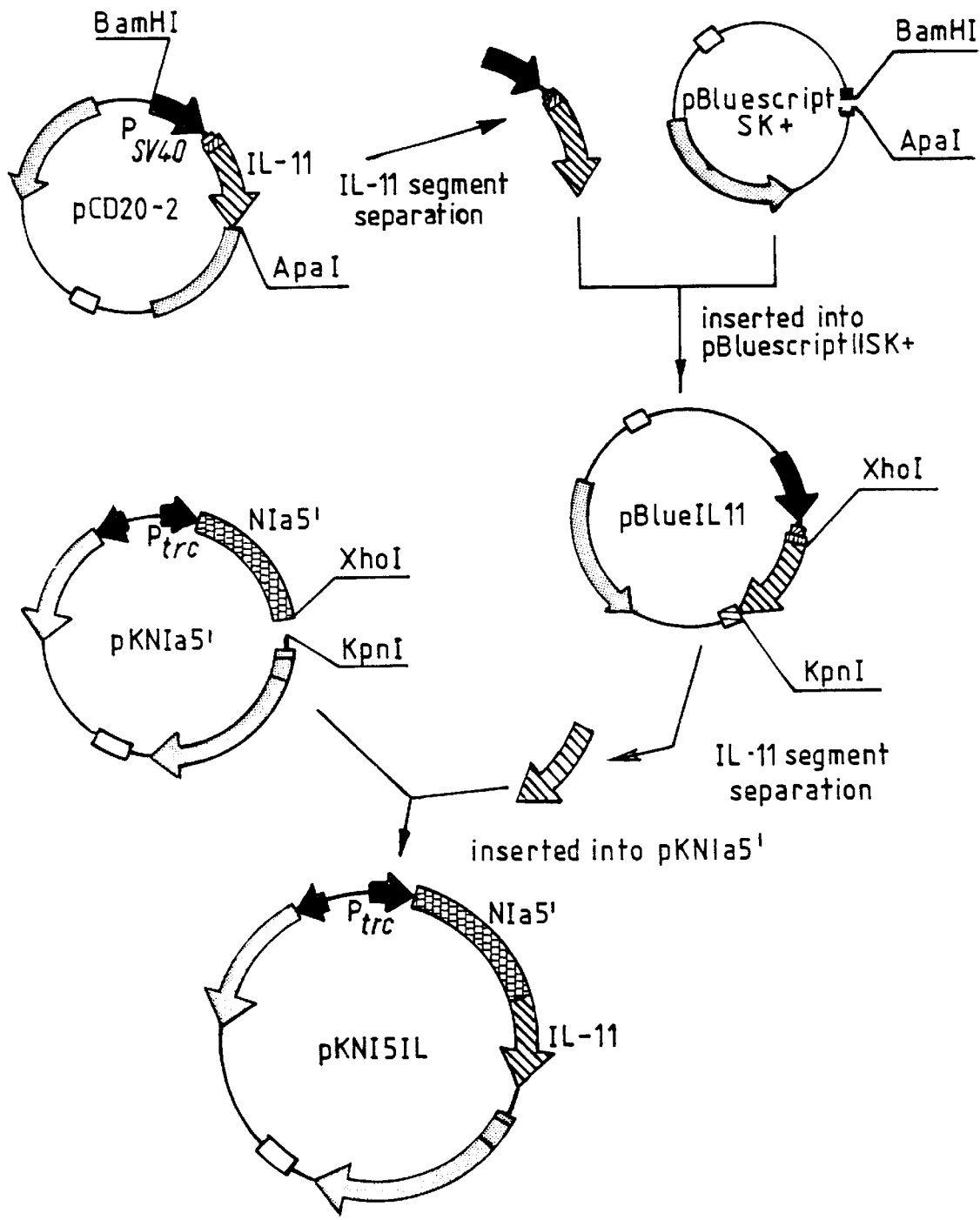
FIG. 3 shows construction of plasmid pKNI5IL containing a part of IL-11 gene and a 5'-region of NIa.
Figure 6:
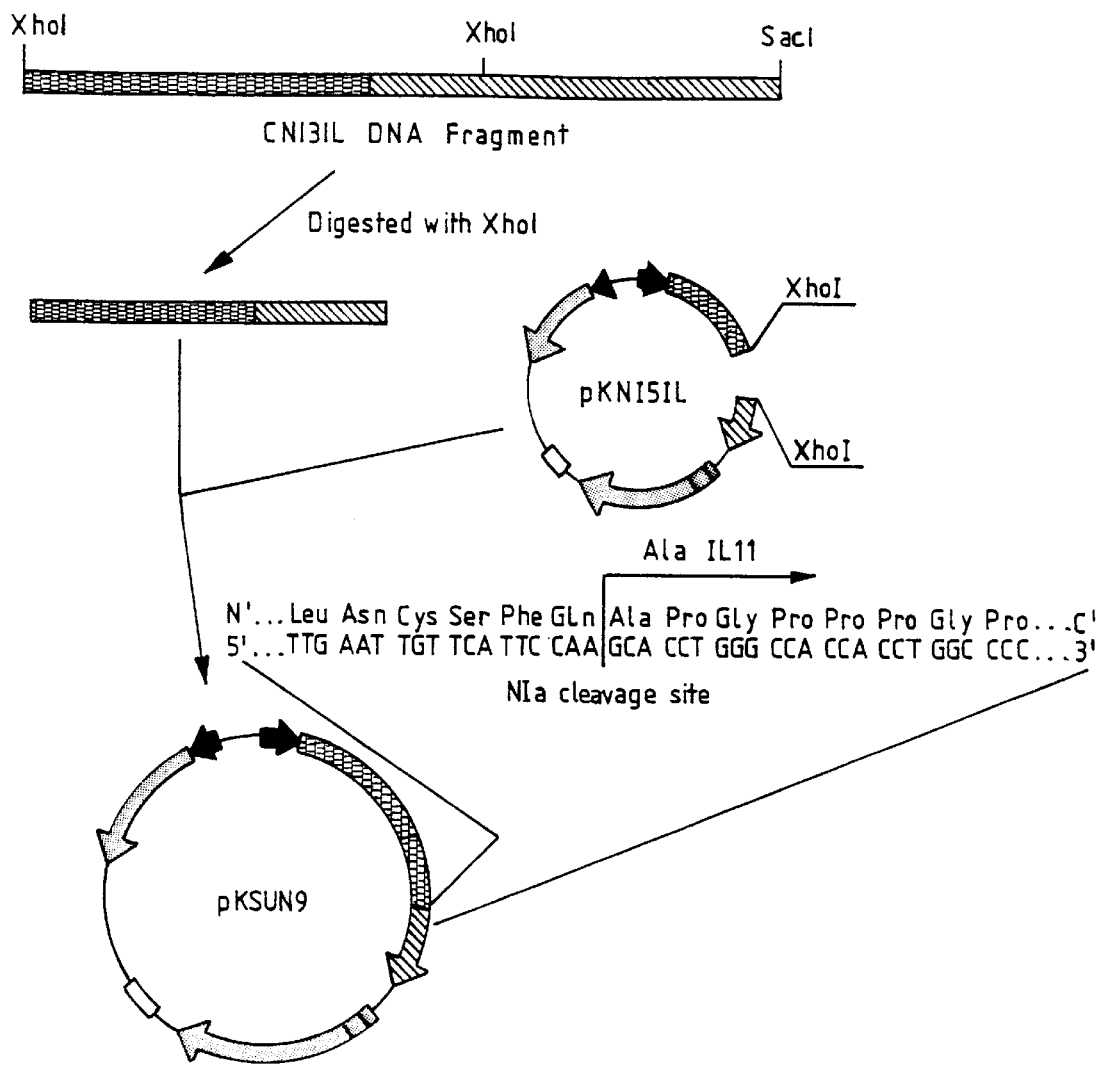
FIG. 6 shows the construction of plasmid pKSUN9.

The resulting Mat-IL-11 fragment (devoid of its N-terminus) was integrated using T4 ligase into pKNI5' which had previously been cleaved with the restriction enzymes XhoI and KpnI and also treated with CIAP. We designated the resulting construct pKNI5IL (FIG. 3). In order to ligate the specific sequence at the C-terminus of NIa with Mat-IL-11 via Ala while keeping the same reading frame, four kinds of PCR primers were synthesized:
5'AGGAAAAGAGTTCCTCGAGC 3' (referred to as NSX2; sequence ID number: 5),
5'AATTGTTCATTCCAAGCACCTGGGCCAC-CACCTGGC 3' (referred to as NSJ001P; sequence ID number: 6),
5'GCCAGGTGGTGGCCCAGGTGCTTGGAAT-GAACAATT 3' (referred to as NSJ002N; sequence ID number: 7), and
5'TTGTCAGCACACCTGGGAGCTGTAGAGCTC3' (referred to as ILSAC; sequence ID number: 8).

The first PCR reaction carried out used the pair of primers NSX2 and NSJ002N, with pNS51 DNA as template to amplify a region of the insert coding for the C-terminus of NIa (designated the CNI3 region). Separately, another PCR reaction was performed using the pair of primers NSJ001P and ILSAC, with pNS51 DNA as template to amplify a region of the insert coding for N-terminus of the IL-11 peptide (designated the 5' IL region). For the PCR program, a cycle of 92° C. for 1 minute, 37° C. for 1 minute and 72° C. for 2 minutes was repeated 20 times followed by a single cycle of 92° C. for 1 minute, 37° C. for 1 minute and 72° C. for 30 minutes. The products obtained from each PCR procedure were extracted with phenol and precipitated with ethanol, and then subjected to 5% polyacrylamide gel electrophoresis. A gel band containing the amplified DNA band with the gel was excised and the DNA was electrically recovered from the gel slice using the electroelution method described above. The results are shown in FIG. 4.

The resulting two amplified DNA fragments were regions of the primers NSJ001P and NSJ002N, i.e., a 3' terminal portion of the CIN3 DNA fragment and a 5' terminal portion of the 5'IL DNA fragment, which have partial homology in the nucleotide sequences. Thus, if PCR is carried out again using the primers NSX2 and ILSAC, the homologous portions will hybridize so that a fused DNA comprising portions of both genes can be obtained, the homologous portion acting as a linking part (FIG. 5). Accordingly, the recovered CIN3 DNA fragment and 5'IL DNA fragment were mixed and PCR was carried out again using only NSX2 and ILSAC as primers. The PCR program consisted of 10 cycles of: 92° C. for 1 minute, 37° C. for 1 minute and 72° C. for 2 minutes; followed by 20 cycles of: 92° C. for 1 minute, 45° C. for 1 minute and 72° C. for 2 minutes; followed by a single cycle of: 92° C. for 1 minute, 55° C. for 1 minute and 72° C. for 30 minutes. After treatment with phenol and precipitation with ethanol, 5% polyacrylamide gel electrophoresis was performed to obtain a CNI3IL DNA fragment in which CNI3 and 5'IL were fused. The method is shown in FIG. 5.

The CNI3IL DNA fragment was cleaved with the restriction enzyme XhoI and the resulting fragment was inserted using T4 DNA ligase into pKNI5' which had previously been cleaved with the restriction enzyme XhoI and dephosphorylated with CIAP. The resulting plasmid was cloned into *E. coli* strain JM 109. In order to select a clone in which the CNI3IL fragment had been inserted in the correct orientation, plasmids were extracted from the resulting clones and PCR was carried out by using the primers NSX2 and ILSAC. Using this system, only a DNA band from a clone in which the fragment has been inserted in the correct orientation is detectable. Plasmid pKSUN9 in which NIa and Mat-IL-11 are ligated in the same reading frame via a cleavage sequence, Gln-Ala, was obtained (FIG. 6).

I) Expression of Ala-IL-11 in a Bacterial Cell

*E. coli* carrying plasmid pKSUN9 (hereinafter, abbreviated as strain KSUN9) was cultured with shaking at 37° C. overnight in 5 ml of LB medium containing 42 μg/ml of ampicillin. 2.5 ml of the resulting KSUN9 culture was added to 250 ml of fresh LB medium (containing the same amount of ampicillin) and cultured with shaking at 37° C. until the $OD_{600nm}$ reached 1.0. Once the $OD_{600nm}$ had reached 1.0, IPTG was added to a final concentration of 0.1 mM and the mixture was cultured with shaking at 28° C. for a further 12 hours.

A second culture was produced following exactly the same procedure, except that the final culture at 28° C. was performed for 36 hours or longer with an IPTG concentration of 1 mM, in order to obtain mature IL-11 (which has an N-terminal Pro).

J) Western Blotting

Western blotting was performed in order to determine whether pKSUN9 is functional in *E. coli* and also whether the constructed recombinant gene is expressed.

Each of the 12 and 36 hour cultures induced with IPTG was further processed as follows. Cells were recovered from 2 ml of the culture by centrifugation at 3,000×g at 4° C. for 5 minutes, and the pellet was suspended in 100 μl of 20 mM sodium borate buffer (adjusted to pH 9.0 with 0.1 N NaOH). The resulting suspension was treated with a sonicator (Handysonic UR-20P, manufactured by Tomy Seiko Co.) at a setting of 8 for 2 minutes to disrupt the cells and then centrifuged at 10,000×g at 4° C. for 10 minutes. The supernatant containing the soluble protein fraction was recovered. Five μl of the supernatant was then run on a 12% SDS polyacrylamide electrophoresis gel following the Laemmli method [Laemmli, U. K. (1970), Nature 227: 680–685].

After electrophoresis, the gel was shaken in a transfer buffer (25 mM Tris, 192 mM glycine, 20% methanol) for 5 minutes and blotted onto a piece of PVDF membrane (Trans-Blot Transfer Medium, manufactured by Bio-Rad Laboratories) by treatment at 15 V for 1 hour using Trans-Blot-SD Semi-Dry Transfer Cell (manufactured by Bio-Rad Laboratories). The blotted PVDF membrane was washed in PBS-Tw medium for 10 minutes. The washed PVDF membrane was transferred to PBS-Tw containing 5% Skim Milk (manufactured by Snow Brand Milk Products) at 37° C. for 1 hour for blocking.

After blocking, the PVDF membrane was further washed in PBS-Tw once for 10 minutes and twice for 5 minutes, and then transferred to anti-IL-11 rabbit serum which had been diluted 10,000 fold in PBS-Tw, and incubated at: 37° C. for 20 minutes. The PVDF membrane was then washed again with PBS-Tw, once for 10 minutes and twice for 5 minutes.

The PVDF membrane was then transferred to anti-rabbit IgG goat antibody labeled with horse radish peroxidase (manufactured by Amersham) which had been diluted 5,000 fold with PBS-Tw, and incubated at 37° C. for 20 minutes. After this time, the PVDF membrane was again washed in PBS-Tw, once for 10 minutes and 4 times, each for 5 minutes.

After this further washing, the PVDF membrane was treated with enhanced chemiluminescence (ECL) detection reagent (manufactured by Amersham), and the bands which reacted with the anti-IL-11 antibody were shown up by bringing the PVDF membrane into contact with an X-ray film for a period of between 30 seconds and 5 minutes.

As a result of the above Western blotting, signal bands corresponding to molecular weights of about 50 kDa and about 23 kDa were detected from both the 12-hour and the 36-hour cultures. The 23 kDa band exhibited substantially the same mobility as that of the mature IL-11 used as a control. Thus, the 23 kDa signal band appeared to be IL-11 which had been cleaved out of the NIa/IL-11 fusion protein by the proteolytic activity of NIa at the Gln-Ala linking sequence. It was deduced that the heavier band (50 kDa) was the uncleaved fusion protein.

Hereinafter, the 23 kDa protein obtained from the 12-hour culture will be referred to as 23 kDa-ON and the 23 kDa protein obtained from the 36-hour culture will be referred to as 23 kDa-36hr.

K) Purification of the 23 kDa-ON and 23 kDa-36 hr Proteins

The 23 kDa-ON and 23 kDa-36 hr proteins were purified in order to determine the amino acid sequences of their N-termini. 250 ml of each of the 12-hour and the 36-hour cultures were obtained by following the same procedure described in I) above. Each culture was then further processed as follows. The culture was centrifuged at 5,000×g at 4° C. for 15 minutes and the pellet was suspended in 10 ml of 20 mM borate buffer (pH 9.0) and disrupted with each of a French press and a sonicator. The soluble protein fraction was recovered as the supernatant after centrifugation at 15,000×g at 4° C. for 30 minutes.

The resulting soluble protein fraction was then subjected to weak ion exchange column chromatography using FPLC manufactured by Pharmacia using the following conditions:

| | |
|---|---|
| Column: | CM Toyopearl Pack 650M (2.2 × 20 cm, manufactured by Toso) |
| Elution buffers: | A = 10 mM boric acid - sodium hydroxide (pH 9.0), 13 mM potassium chloride |
| | B = 10 mM boric acid - sodium hydroxide (pH 9.0), 13 mM potassium chloride, 400 mM sodium chloride |
| Flow rate: | 2.5 ml/min |
| Fraction volume: | 5 ml/tube |

The concentration gradient used was a linear gradient from eluent A to eluent B over a period of 120 minutes.

Each eluted fraction was subsequently subjected to an enzyme-linked immunosorbent assay (ELISA), to identity fractions containing IL-11.

The ELISA was performed as follows. Each well of a 96 well-immunoplate (Maxisoap; manufactured by Nunc) was loaded with 100 μl of 50 mM sodium carbonate buffer (pH 9.6) containing 1 μg/ml of anti-IL-11 mouse monoclonal antibody and the plate was then incubated at 37° C. for 1 hour. After this time, each well was washed four times with PBS-T medium (PBS containing 0.1% Tween 20).

Each of the FPLC fractions obtained above was diluted 100 fold with PBS-T and loaded into the wells in aliquots of 100 μl/well. The plate was incubated at 37° C. for 1 hour, the wells were again washed with PBS-T, and then each well was loaded with 100 μl of anti-IL-11 rabbit IgG diluted with PBS-T to a final concentration of 1 μg/ml.

The plate was further incubated at 37° C. for 1 hour and washed with PBS-T, and then each well was loaded with 100 μl of alkaline phosphatase-labeled goat anti-rabbit IgG antibody (manufactured by Gibco Bethesda Research Laboratories) which had been diluted 3,000 fold in PBS-T. The plate was again incubated at 37° C. for 1 hour and then washed with PBS-T. Each well was then loaded with 100 μl of alkaline phosphatase substrate solution. The plate was incubated at room temperature for a further 30 minutes to 1 hour, after which time the coloring of each well was measured as absorbance at 405 nm to identify the fraction(s) of interest.

The fractions from the FPLC procedure identified by the above ELISA procedure as containing a substance reacting with rabbit anti-IL-11 antibody (fraction nos. 19 to 25) were pooled, concentrated 100-fold with Centprep-10 (manufactured by Amicon), and then run on a 12% SDS polyacrylamide electrophoresis gel in accordance with the Laemmli method (supra). The gel was then electro-blotted onto a piece of PVDF membrane in a manner similar to that used in the above in the Western blotting procedure, but using the Problot membrane (manufactured by Applied Biosystems) as the PVDF membrane.

After blotting, the membrane was thoroughly washed with redistilled water, stained with Coomassie Brilliant Blue R-250, destained with 50% methanol, and then the band containing the protein which reacted with anti-IL-11 antibody in the Western blot was excised.

The amino acid sequence of the N-terminus of the protein was analyzed using a protein sequencer (manufactured by Applied Biosystems). The N-terminal sequence of the band from 23 kDa-ON which reacted with the anti-IL-11 antibody was determined to be:
Ala-Pro-Gly-Pro-Pro-Pro-Gly- (sequence ID No. 9)

This sequence corresponds to the amino acid sequence −1 to +6 of the amino acid sequence of the mature IL-11 protein. Based on this finding, it could be deduced that the 23 kDa protein obtained from the 12-hour culture and which reacted with anti-IL-11 antibody was Ala-IL-11. Accordingly, it seemed apparent that this protein was generated by the proteolytic activity of NIa cleaving the NIa/IL-11 fusion protein at the Gln-Ala site in the specific cleavage sequence.

The N-terminal sequence of the band from 23 kDa-36 hr which reacted with the anti-IL-11 antibody was determined to be:
Pro-Gly-Pro-Pro-Pro-Gly-Pro- (sequence ID No. 10) This sequence corresponds to the amino acid sequence +1 to +7 of mature IL-11. Accordingly, we were able to reach the following conclusions.

Following induction with IPTG, the NIa/IL-11 fusion protein was expressed in $E.$ $coli.$ By 12 hours culturing subsequent to induction, the expressed NIa/IL-11 fusion protein was cleaved at the Gln-Ala peptide bond in the specific cleavage sequence by the protease activity of NIa.

After cleavage of the peptide bond with NIa, mature IL-11 but having an extra Ala on its N-terminus was expressed in $E.$ $coli.$ By culturing for a further 24 hours after the expression of Ala-IL-11 had been established, Ala-IL-11 matured to IL-11 in which the Ala residue which had been present at the N-terminus of Ala-IL-11 was deleted.

Based on the above findings, it was concluded that the 23 kDa protein obtained after culturing for 36 hours was a mature type of IL-11 whose N-terminus was Pro.

Therefore, it was established that IL-11 could be expressed as a fusion protein with NIa and that the activity of NIa could cleave a specific linker sequence containing Gln-Ala to afford Ala-IL-11. Continued culture was then able to afford mature IL-11 wherein the alanine residue had been deleted to expose a proline N-terminal by a factor present in $E.$ $coli.$ In order to ensure that the expressed IL-11 and Ala-IL-11 were biologically active, adipogenesis inhibitory factor (AGIF) activity was determined as an index. The fact that IL-11 has adipogenesis inhibitory activity has previously been demonstrated [Kawashima, I. et al. (1991), FEBS L. 283: 199–202].

L) Measuring Inhibitory Effects on the Morphological Changes from 3T3-L1 Cells to Adipocytes The method for determining the AGIF activity used in the present invention is as follows. Mouse embryonic fibroblast cell line 3T3-L1 [Green, H. and Kehinde, O. (1974), Cell 1: 113–116] purchased from ATCC is used. The cells are in all cases cultured in a mixed humid atmosphere of 10% $CO_2$—90% air at 37° C. and subcultured with medium A. Induction of adipogenic differentiation is carried out following the procedure described by Rubin et al. [Rubin, C. S. et al. (1978), J. Biol. Chem. 253: 7570–7578].

3T3-L1 cells are suspended in medium A to a density of $1.0\times10^4$ cells/ml, seeded onto a 48 well multicluster dish (manufactured by Coaster, 0.5 ml/well), and then cultured. After 3 days of culturing, the cells reach confluence. The medium is then replaced with fresh medium A and, after culturing for a further 2 days, the medium is replaced with an adipogenesis induction medium, medium B, together with the simultaneous addition of 0.5 ml of the test sample. The medium is replaced with fresh medium B and a fresh sample every two days.

Instead of medium B, adipocyte maintaining medium, medium C is used to replace exhausted medium in the wells, starting at varying times for different wells between days 4 and 7 after the first test sample is added.

After culturing in medium C for 2 days, the cells are fixed with 5% formaldehyde, and any fat particles which have accumulated in the cells and cell nuclei are stained with Oil Red 0 and hematoxylin, respectively. A micrograph is taken and the number of nuclei and the number of cells which have accumulated stained fat particles are counted. The adipogenetic ratio (AR) is calculated according to the following equation:

$$AR(\%) = 100 \times \frac{\text{number of cells accumulating fat particles}}{\text{total number of nuclei}}$$

Fixation of the cells and staining with Oil Red 0 and hematoxylin are carried out in accordance with the procedures described by Yoshio Mitomo and Shojiro Takayama in "Lectures on Clinical Testing" Vol. 12, "Pathology" (1982), published by Ishiyaku Shuppan.

M) Method for the Determination of Lipoprotein Lipase Inhibitory Activity

The determination is carried out in accordance with the method described by Beutler et al. [Beutler, B. A. et al. (1985), J. Immonol. 135: 3972–3977]. Adipogenically differentiated 3T3-L1 cells are prepared as described in L) above, except that no test sample is added when differentiation into adipocytes is induced. Instead, the test sample is added together with fresh medium C and the cells are cultured for 18 hours.

After this time, the medium is removed and the cells are washed twice with PBS(−) (phosphate-buffered saline, manufactured by Nissui Seiyaku) and each well is then loaded with 300 $\mu$l of medium D and cultured for a further 1 hour. 100-$\mu$l aliquots of each of the culture supernatants are taken for use in measuring lipoprotein lipase (LPL) activity, which is measured in triplicate for each sample to obtain an average.

LPL activity is measured as described by Nilsson-Ehle and Schotz [Nilsson-Ehle, P. and Schotz, M. C. (1976), J. Lipid Res. 17: 536–541]. The aliquots of supernatant obtained above are each mixed with an equal volume of LPL substrate solution and allowed to react at 37° C. for 120 minutes. The reaction is stopped by adding 1.05 ml of 0.1 M potassium carbonate buffer (adjusted to pH 10.5 with 0.1 M potassium borate) and 3.25 ml of a mixture of methanol:chloroform:heptane [141:125:100 (v/v)] with vigorous stirring. The mixture is then centrifuged at 3,000×g for 15 minutes at room temperature. The H content of the water-methanol phase is counted with a liquid scintillation counter.

One unit of LPL activity is defined as being that activity which generates 1 $\mu$mol of fatty acid per minute. The 13 mM glycerol tri[9,10(n)-³H]oleate in the substrate solution is prepared by diluting glycerol tri-[9,10(n)-³H]oleate (37.0 GBq/mol), manufactured by Amersham with triolein (manufactured by Sigma), followed by purification on a silica gel column chromatography.

The following Examples relate to the glutathione reducing protein embodiment of the present invention.

EXAMPLE 1

Extraction of Poly(A)⁺ RNA from KM-102 Cells

KM-102 cells were cultured in 36 plastic, 15 cm diameter, culture dishes with Iscove's modified minimum essential medium (Boeringer-Mannheim) containing 10% fetal bovine serum. After growing the cells to confluence, phorbol myristyl acetate (PMA) and calcium ionophore A23187 (Sigma) were added to final concentrations of 10 ng/ml and 0.2 μM, respectively, and culturing was continued at 37° C. Lots of 12 dishes were harvested 3, 6 and 14 hours later, and each dish was separately dissolved in guanidine thiocyanate solution and the liquid phase was collected.

Isolation of poly(A)⁺ RNA was basically performed as described in "Molecular Cloning—A Laboratory Manual" [Maniatis, T. et al. (1982) pp. 196–198]. The following provides a detailed description of the procedure.

Each recovered liquid phase was individually treated as follows. The liquid was repeatedly drawn up and discharged from a 10 ml syringe barrel equipped with a 21G syringe needle. 3 ml of a solution of 5.7 M CsCl-0.1 M EDTA (pH 7.5) was added in advance to a Polyaromar centrifuge tube matching the size of a rotor bucket of an RPS40-T centrifuge (Hitachi Koki). The cell preparation was then overlaid on the solution in the tube until the tube was full.

After centrifuging at 30,000 rpm for 18 hours at 20° C., the resulting pellet was suspended in 400 μl of distilled water followed by ethanol precipitation. The resulting pellet was dissolved in 400 μl of distilled water and added to an equal volume of chloroform/1-butanol mixture (4:1 v/v) with stirring and the aqueous layer was collected by centrifugal separation. Ethanol precipitation was performed once again, and the resulting pellet was dissolved in 600 μl of distilled water to obtain whole RNA. About 4.5 mg of whole RNA was obtained from each of the pooled PMA/A23187-stimulated samples from 3, 6 and 14 hours.

600 μg of each of the three types of whole RNA obtained in this manner were pooled and subjected to oligo(dT) cellulose column chromatography to purify the poly(A)⁺ RNA.

The whole RNA was dissolved in adsorption buffer, and heated at 65° C. for 5 minutes. The resulting solution was applied to an oligo(dT) cellulose column (Pharmacia, type 7) loaded with adsorption buffer, and eluted with eluting solution to recover 100 μg of poly(A)⁺ RNA.

EXAMPLE 2

Preparation of a cDNA Library

A cDNA library was prepared by the Okayama-Berg method.

5 μg of poly(A)⁺RNA and 24 units of reverse transcriptase (Seikagaku Corp.) were allowed to react at 42° C. for 1 hour in 20 μl of reverse transcriptase reaction solution.

The reaction was stopped by the addition of 2 μl of 0.25 M EDTA and 1 μl of 10% SDS, and the solution was then deproteinized with 20 μl of a phenol/chloroform mixture (1:1 v/v). Following centrifugation to remove the proteinaceous fraction, 20 μl of 4 M ammonium acetate and 80 μl of ethanol were added to the supernatant which was then cooled at −70° C. for 15 minutes. After this time, the precipitate was collected by centrifugal separation, washed with 75% ethanol and then dried under reduced pressure.

The dried precipitate was dissolved in 15 μl of terminal transferase reaction solution and warmed at 37° C. for 3 minutes. At the end of this time, .18 units of terminal deoxynucleotidyl transferase (Pharmacia) were added to the reaction solution and allowed to react for 5 minutes. 1 μl of 0.25 M EDTA and 0.5 μl of 10% SDS were added to stop the reaction and the solution was then deproteinized with phenol-chloroform (as described above) and centrifuged to remove the proteinaceous fraction. The supernatant was collected and thoroughly mixed with 15 μl of 4 M ammonium acetate and 60 μl of ethanol. This mixture was cooled at −70° C. for 15 minutes and the precipitate was collected by centrifugation.

The resulting pellet was dissolved in 10 μl of restriction enzyme buffer, and 2.5 units of restriction enzyme HindIII were added to the resulting solution which was allowed to stand at 37° C. for 1 hour to effect digestion.

The reaction solution was then deproteinized with phenol-chloroform followed by ethanol precipitation, and the supernatant was cooled at −70° C. for 15 minutes. The resulting precipitate was collected by centrifugation and dissolved in 10 μl of TE buffer [10 mM Tris-HCl (pH 7.5) and 1 mM EDTA]. 1 μl of the resulting solution was made up to 10 μl of a reaction solution containing 10 mM Tris-HCl (pH 7.5), 1 mM EDTA, 100 mM NaCl and 10 ng of oligo(dG)-tailed linker DNA [3'-oligo(dG)-tailed pL-1 HindIII linker, Pharmacia], followed by heating at 65° C. for 5 minutes and then warming at 42° C. for 30 minutes. The reaction mixture was cooled over ice water, followed by the addition thereto of 10 μl of 10×ligase buffer, 78 μl of distilled water and 8 units of T4 DNA ligase. The reaction solution was then kept overnight at 12° C.

The following day, the reaction mixture was combined with 10 μl of 1 M KCl, 1 unit of ribonuclease H, 33 units of DNA polymerase I, 4 units of T4 DNA ligase, 0.5 μl of dNTP solution (20 mM DATP, 20 mM dCTP, 20 mM dGTP and 20 mM dTTP) and 0.1 μl of 50 μg/ml bovine serum albumin (BSA), and the resulting mixture was warmed first at 12° C. for 1 hour and then at 25° C. for 1 hour. After this time, the reaction solution was diluted five-fold with distilled water and was then immediately used to transform E. coli DH5 α using the Hanahan method [Hanahan, D. (1983) J. Mol. Biol. 166, 557–580] thereby to prepare a cDNA library of KM-102 cells.

EXAMPLE 3

Preparation of an Oligonucleotide Probe

Based on the AUUUA sequence in the 3' non-translated region of the mRNA of cytokines, the 15-base oligonucleotide 5'-TAAATAAATAAATAA-3' (sequence ID number 13), designated ATT-3, was chemically synthesized. Synthesis was performed using the 380B automatic DNA synthesizer (Perkin-Elmer Japan Applied Biosystems) following the directions supplied in the accompanying manual. The method employed was the phosphoamidite method described by Caruthers et al. [Matteucci, M. D. and Caruthers, M. H. (1981) J. Am. Chem. Soc. 103, 3185–3191]. After synthesis of the 15-mer, the resulting oligonuculeotide was severed from the support and the protecting groups were removed. The resulting oligonucleotide solution was lyophilized to form a powder which was then dissolved in distilled water and stored frozen at −20° C. until the time of use.

EXAMPLE 4

Screening the cDNA Library 6,500 colonies generated from the cDNA library prepared in Example 2 above were fixed on a nitrocellulose filter in accordance with the method described by Grunstein and Hogness [Grunstein, M. and Hogness, D. S. (1975) Proc. Natl. Acad. Sci. USA 72, 3961–3965]. The ATT-3 probe prepared in Example 3 was 5'-labelled with $^{32}$P following standard procedures (see "Molecular Cloning—A Laboratory Manual"), and the labelled probe was used for colony hybridization.

Pre-hybridization was performed at 37° C. for 3 hours in the following: 6×SSC, 1×Denhardt solution, 0.25% SDS, 0.05% sodium pyrophosphate and 100 μg/ml of denatured salmon sperm DNA. Hybridization was then performed overnight at 31° C. in the following: 6×SSC, 1×Denhardt solution, 17 μg/ml of yeast tRNA and 0.05% sodium pyrophosphate containing the $^{32}$P-labeled probe ATTT-3.

On the following day, the nitrocellulose filter was washed at room temperature for 2 hours with a 6×SSC solution containing 0.05% sodium pyrophosphate. Subsequent autoradiography revealed 33 positive clones.

The plasmid DNA was extracted from the positive clones by following standard procedures. Several clones were then selected at random and their partial cDNA nucleotide sequences were determined by the dideoxy method. These partial sequences were then examined for homology with nucleotide sequences registered in the EMBL or GenBank databases via a personal computer and it: was established that some of the partial sequences of clones detected by ATT-3 had homology with parts of the Alu repeat [Schmid, C. W. and Jelinek, W. R. (1982) Science 216, 1065–1070].

A DNA fragment containing the Alu repeat sequence was prepared from human genome DNA and labeled with $^{32}$P, following standard procedures. This labeled DNA was used as a probe in colony hybridization using the 33 clones identified above, and it became clear that 12 of the clones possessed the Alu repeat. The length of the cDNA insert of each of the remaining 21 clones was determined, and it was established that the length was variable over a range of 50 to 3,600 bases.

Restriction enzyme mapping was performed on the cDNA inserts of the remaining 21 clones, and partial nucleotide sequences were determined as above. These partial sequences were then examined as above for homology with nucleotide sequences registered in the EMBL or GenBank databases via a personal computer, and those clones having novel sequences were selected.

EXAMPLE 5

Northern Hybridization of Clone No. 31

One of the clones, clone no. 31 (designated pcD-31) had a cDNA insert of about 560 bp. A PstI-AatI fragment (292 bp) was obtained from the cDNA insert of pcD-31 and was labeled with $^{32}$P for use as a probe in a Northern blot procedure using poly(A)$^+$ RNA prepared from KM-102 cells, following a procedure similar to that of Example 1. This hybridization was used to determine the length of the naturally occurring mRNA which corresponds to the insert of pcD-31.

The procedure of the Northern hybridization was as follows. 5.5 μg of poly(A)$^+$ RNA was prepared from KM-102 cells and incubated at 50° C. for 1 hour in a mixture of 1 M glyoxal, 50% dimethyl sulfoxide (DMSO) and 0.01 M disodium hydrogen phosphate (pH 7.0). At the end of this time, 4 μl of electrophoresis pigment were added to the incubated mixture which was then electrophoresed on a 1% agarose gel in 1×TAE.

Following the electrophoresis, the RNA on the agarose gel was transferred overnight onto a nylon membrane filter (Bio Rad, Zeta-Probe) using 20×SSC using the capillary transfer method (see "Molecular Cloning—A Laboratory Manual"). After transferrence, the filter was gently washed with 2×SSC, air dried, and then additionally dried at 80° C. for 2 hours to fix the mRNA.

The PstI-AatI fragment of pcD-31 was labeled with $^{32}$P using the Multiprime DNA Labeling System (Amersham).

Pre-hybridization was performed on the filter for 3 hours at 37° C. in a solution containing 5×SSCP, 2.5×Denhardt solution, 50% formamide, 10 mM disodium hydrogen phosphate (pH 7.0), 0.5% SDS and 100 μg/ml of denatured salmon sperm DNA.

Hybridization was then performed on the filter overnight at 42° C. in a solution containing the $^{32}$P-labeled probe, 5×SSCP, 1×Denhardt solution, 50% formamide, 10 mM disodium hydrogen phosphate (pH 7.0), 0.1% SDS and 100 μg/ml of denatured salmon sperm DNA. The following day, the filter first was washed for 1 hour at 37° C. with a solution containing 50% formamide, 5×SSC and 0.1% SDS, then washed for 2 hours at the same temperature with a solution containing 40% formamide, 5×SSC and 0.1% SDS, and finally washed at room temperature for 15 minutes with a solution of 2×SSC. Subsequent autoradiography showed that the cDNA insert of clone pcD-31 is not full length, and that the full length of the corresponding mRNA is 3.9 kb (determined from a calibration curve based on molecular weight markers).

EXAMPLE 6

Preparing a Fresh Library for Screening Clone pcD-31 cDNA

A fresh cDNA library was prepared using the cDNA Synthesis System Plus and cDNA Cloning System (λgt10, adapter method, supplied by Amersham).

5 μg of poly(A)$^+$ RNA extracted from KM-102 cells (following a procedure similar to that of Example 1) and 100 units of reverse transcriptase were reacted at 42° C. for 40 minutes in 50 μl of reverse transcriptase reaction solution. After this time, 20 μCi of [α-$^{32}$P]dCTP, 93.5 μl of second strand buffer, 4 units of ribonuclease H and 115 units of DNA polymerase I (all provided with the kit) were added to the reaction solution which was then first incubated at 12° C. for 1 hour, then incubated at 22° C. for 1 hour and finally heated at 70° C. for 10 minutes. After this heating treatment, 10 units of T4 DNA polymerase (provided with the kit) were added to the reaction solution and allowed to react at 37° C. for 10 minutes.

The reaction mixture was then subjected to phenol-chloroform deproteinization. The reaction solution was centrifuged and the supernatant was collected and mixed well with 250 μl of 4M ammonium acetate and 1 ml of ethanol. The mixture was cooled overnight at −20° C. and the precipitate was collected by centrifugation. The resulting pellet was dissolved in 30 μl of sterile water. 10 μl of the resulting solution were removed and added to a mixture of 2 μl of ligase/kinase buffer, 250 pmole of EcoRI adapter and 5 units of T4 DNA ligase (all provided with the kit) and the resulting mixture was incubated overnight at 15° C.

The whole of the reaction solution was then applied to the size fractionation column provided with the kit in order to remove the EcoRI adapter. The reaction solution was collected in 120 µl aliquots and each aliquot was mixed with 200 µl of 0.25×TE buffer. The 10th to 17th fractions were pooled and concentrated with butanol to a total volume of 120 µl.

The whole of concentrated preparation was then mixed with 55 µl of sterile water, 20 µl of ligase/kinase buffer and 40 units of T4 polynucleotide kinase (all provided with the kit), and the resulting mixture was incubated at 37° C. for 30 minutes. After this time, the reaction mixture was deproteinized by the phenol-chloroform method three times and then precipitated with ethanol and cooled overnight at −20° C. The resulting precipitate was collected by centrifugation and dissolved in 10 µl of sterile water to provide the cDNA sample.

1 µg of the EcoRI arm of λgt10, 1 µl of ligase/kinase buffer and 2.5 units of T4 DNA ligase (all provided with the kit) were added to either 2 µl of the cDNA sample, followed by incubation overnight at 15° C. A sample containing 4 µl of the cDNA sample was prepared in the same way. Each sample was then further treated as follows. The whole of the resulting reaction solution was first added to 10 µl of Extract A (provided with kit) and the resulting mixture was then added to 15 µl of Extract B (provided with kit), and the resulting mixture was incubated at 20° C. for 20 minutes to allow the in vitro packaging reaction to take place.

After this time, 470 µl of SM buffer were added to the reaction solution which was then stored at 4° C. *E. coli* strain NM514 treated with 10 mM MgSO$_4$ was then infected with the stored solution to create a λgt10 library of KM-102 cDNA.

EXAMPLE 7

Screening the cDNA Library

2×10$^5$ plaques obtained from the combined cDNA libraries prepared in Example 6 were fixed to nylon filters (Hybond N, Amersham) by the following procedure.

Infected *E. coli* prepared in Example 6 were cultured on ten 9 cm plates containing solid LB medium so that between 1 and 2×10$^4$ plaques were formed per plate.

The plaques were transferred onto the plate by gently pressing the nylon filter onto the plate. An 18G syringe needle was then used to puncture the filter and mark the gel at 3 locations for reference. The filter was then allowed to stand at 4° C. for 5 to 10 minutes and was then peeled off and dipped in an alkaline solution (0.1 N NaOH, 1.5 M NaCl) for 20 seconds. The filter was then transferred to a neutral solution [0.2 M Tris-HCl (pH 7.5), 2×SSCP] for a period of between 20 seconds and 1 minute, and was next air-dried at room temperature for 2 hours. Finally, the filter was dried at 80° C. for 2 hours.

EXAMPLE 8

Probe Preparation and Hybridization $^{32}$P-Labeled probes were created from from pcD-31 (obtained in Example 4) by labeling the PstI-AatI fragment and the EcoT22I-AatI fragment (223 bp) from pcD-31 using the Multiprime DNA Labelling System. Plaque hybridization was performed on the filter obtained in Example 7 using the above probes.

Pre-hybridization was performed by placing the filter in a bath of 50% formamide, 5×SSCP, 2.5×Denhardt solution, 0.01 M disodium hydrogen phosphate (pH 7.0), 0.5% SDS and 100 µg/ml of denatured salmon sperm DNA and incubating at 37° C. for 2 hours.

Hybridization was then performed by placing the filter in a reaction solution containing the $^{32}$P labeled probes prepared above and 50% formamide, 5×SSCP, 1×Denhardt solution, 0.01 M disodium hydrogen phosphate (pH 7.0), 0.1% SDS and 100 µg/ml of denatured salmon sperm DNA, and incubating overnight at 37° C.

The following day, the filter was first washed at room temperature for 3 hours with a solution containing 50% formamide, 5×SSC and 0.1% SDS, and then washed at room temperature for 5 minutes with 2×SSC. Autoradiography showed 80 positive clones obtained in this primary screen.

Using the clones identified as positive each time, the procedures of Examples 7 and 8 were repeated a further three times (quaternary screening), and a total of 17 positive clones were ultimately obtained. The cDNA was isolated from each of the 17 clones and the inserts were cut out with EcoRI. The length of each cDNA insert was investigated by agarose gel electrophoresis and clone no. 31-7 was isolated, which had a cDNA insert of 3.9 kbp, corresponding to the complete length of the original mRNA.

EXAMPLE 9

Restriction Mapping of Clone No. 31-7

Figure 7:
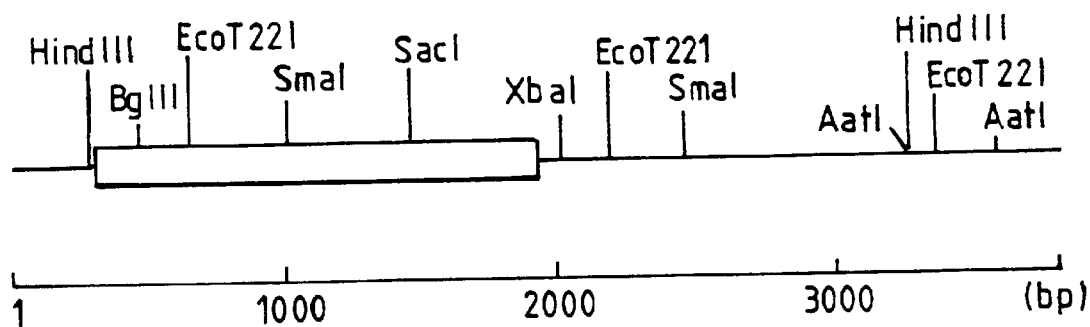
FIG. 7 is a restriction enzyme map of pUCKM31-7.

Clone no. 31-7 was digested with EcoRI to isolate and purify the 3.9 kb fragment containing the cDNA insert. This fragment was then inserted into pUC18 using T4 DNA ligase. *E. coli* DH5α was transformed with this new plasmid. Transformed cells were selected by their resistance to ampicillin and clone pUCKM31-7 having a 3.9 kbp cDNA insert was identified by digesting the DNA with EcoRI and subjecting the cleaved DNA to agarose gel electrophoresis.

pUCKM31-7 was cleaved with each of the restriction enzymes HindIII, SacI, XbaI, SmaI, BglII, EcoT22I and AatI, or pairs thereof. Agarose gel electrophoresis was performed on the resulting fragments and the length of each fragment was measured using the λHindIII/φX174HaeIII marker as an indicator. The resulting restriction map is shown in FIG. 7.

EXAMPLE 10

Sequence Determination of Clone No. 31-7

The entire nucleotide sequence of the cDNA insert of pUCKM31-7 was determined by the dideoxy method using an M13 phage. In addition, a portion of the sequence was analyzed with the 373A DNA Sequencer (Perkin-Elmer Japan Applied Biosystems). The resulting nucleotide sequence is ID number 11 in the accompanying Sequence Listing.

The cDNA insert of pUCKM31-7 is 3815 bases long, and clearly has an open reading frame composed of 549 amino acids, starting with methionine. A poly(A) tail is apparently absent. A comparison of the base sequence of the 3' terminal of the insert of pcD-31 with the sequence of clone pUCKM31-7 reveals that the insert of pUCKM31-7 is only missing the poly(A) tail portion (FIG. 8), and nothing else.

The EMBL and GenBank nucleotide databases and the NBRF and SWISS-PROT databases were accessed in order to compare the base and amino acid sequences, respectively. The closest match which was discovered was a 35.3% homology of the peptide sequence with human glutathione reductase. Accordingly, it was concluded that the ORF of the cDNA insert of pUCKM31-7 clearly encodes a novel polypeptide. This novel polypeptide is shown as sequence ID number 12 in the accompanying Sequence Listing.

EXAMPLE 11

Expression and Purification of the Novel Polypeptide

Construction of a High Expression Vector and Expression in COS-1 Cells pUCKM31-7 was digested with HindIII and the 3003 bp fragment containing the cDNA insert was isolated and purified following standard procedures. The terminals of the resulting fragment were blunted using a DNA blunting kit (Takara Shuzo).

Meanwhile, the high expression vector pcDL-SRα296 [Takabe, Y. et al. (1988) Mol. Cell. Biol. 8, 466–472] was digested with PstI and KpnI and the terminals were blunted using a DNA blunting kit. The blunted insert was then ligated into the blunted plasmid in a reaction using T4 DNA ligase. E. coli was then transformed with the resulting DNA by the calcium chloride method, and the resulting $Amp^R$ transformants were selected and the plasmid DNA retained by the organisms was analyzed.

Figure 9:
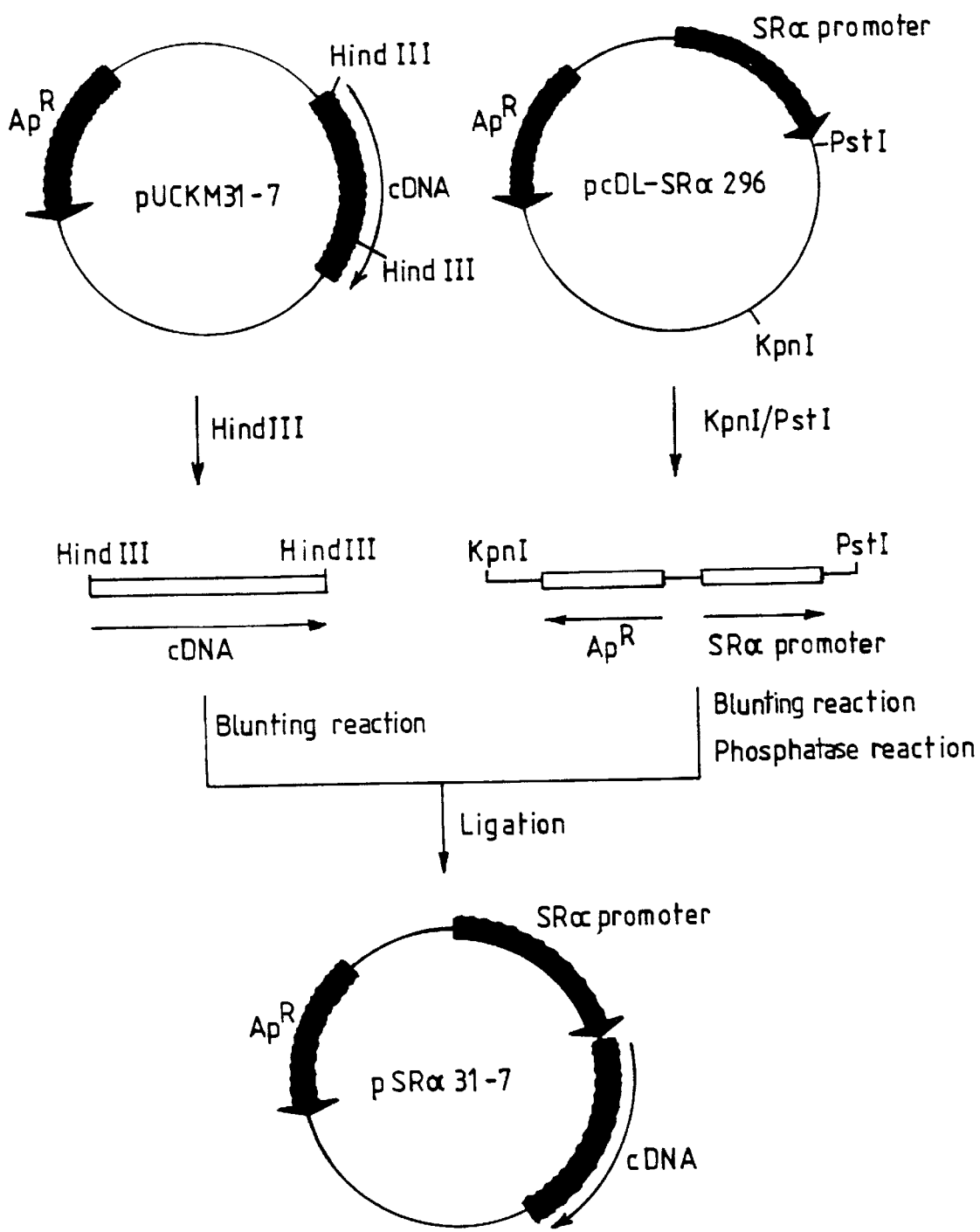
FIG. 9 is a construction diagram of pSR α31-7.

Specifically, a strain in which the direction of cDNA transcription was identical to the direction of the SRα promoter was selected by digestion of the plasmid with HindIII and BglII followed by agarose gel electrophoresis to locate an 800 bp fragment, and the plasmid which was selected was designated pSRα31-7 (FIG. 9). The SRα promoter comprises the SV40 initial promoter and the R-U5 sequence of the long terminal repeat (LTR) of HTLV-1, and has promoter activity which is 10 to 100 times stronger than the SV40 initial promoter alone.

Next, COS-1 cells were transfected with the resulting plasmid pSRα31-7. Transfection of COS-1 cells was performed by electroporation using the GTE-1 gene introduction device (Shimadzu).

COS-1 cells were grown to semi-confluence over the bottoms of seven 150 $cm^3$ flasks, each containing 25 ml DMEM (containing 10% fetal bovine serum). The cultures were then collected and each was treated with 3 ml of Trypsin-EDTA solution (10×solution available from Sigma) and allowed to stand at room temperature until the cells had separated. 1 ml of inactivated fetal bovine serum and 9 ml of fresh trypsin-EDTA solution were then added and the cells were collected by centrifugation. The collected cells were then washed twice with PBS(-) buffer and suspended in PBS(-) buffer to a density of $6 \times 10^7$ cells/ml.

Meanwhile, plasmid DNA was prepared by the cesium chloride method and made up to 200 µg/ml in PBS(-) buffer.

20 µl of each of the above-mentioned PBS(-) preparations of cells and plasmid were mixed and the resulting mixture was placed in a chamber containing electrodes spaced apart at an interval of 2 mm. Two 600V pulses, each for a duration of 30 µsec were then applied to the mixture at an interval of 1 second.

The electrode chamber was cooled at 4° C. for 5 minutes and then the cell-DNA mixture inside was mixed with 10 ml of DMEM containing 10% fetal bovine serum. This mixture was transferred to a Petri Plate and cultured overnight at 37° C. in a 5% $CO_2$ atmosphere. The following day, the culture supernatant was discarded, the cells were washed with serum-free DMEM and then suspended in 10 ml of DMEM and cultured at 37° C. for 3 days. After this time, the cell supernatant was harvested.

Culture supernatant was also harvested from the negative control. The negative control used the plasmid pcDL-SRα296 containing no cDNA insert, but was otherwise prepared in similar manner to the test culture.

1 ml of each of the culture supernatants of the negative control and the test culture were separately processed as follows. The supernatant was first treated with trichloroacetic acid (TCA) to precipitate protein, and the precipitate was collected by centrifugal separation. The resulting precipitate was washed with ice-cooled acetone and air-dried and then dissolved in SDS-polyacrylamide gel electrophoresis (SDS-PAGE) sample buffer containing 2-mercaptoethanol. SDS-PAGE was then performed on a 12.5 gel under reducing conditions.

Silver staining using the silver stain reagent "Daiichi" (Daiichi Chemical Detection) was performed on the bands following electrophoresis. Several specific bands (molecular weight: about 60,000) from the culture supernatant of the test sample were stained.

Since the molecular weight of the polypeptide encoded in pSRα31-7 is about 60,000, and it was also deduced from the amino acid sequence that post-translational modification to add saccharide side chains was unlikely, it was concluded that these several specific bands corresponded to the polypeptide encoded by the cDNA of pSRα31-7.

EXAMPLE 12

Preparation of a High Expression Plasmid for COS-1 Cells

The next step was to verify that the several specific 60 kDa bands identified in Example 11 are the same as the polypeptide encoded by the insert of pSRα31-7. It was also desired to determine the N-terminal amino acid sequence of this polypeptide. Accordingly, a clone was prepared wherein an extra six His residues were encoded for the C-terminal of the polypeptide encoded by the pSRα31-7 insert, immediately before the stop codon. Histidine residues have a high affinity for $Ni^{2+}$ and the objective was to express a polypeptide having a histidine hexamer (6×His), which could be purified using an affinity resin column charged with $NI^{2+}$.

First, a 66 base oligonucleotide 5'-CTAGCGCTCTGGGGCAAGCATCCTCCAGGCTGG CTGCCACCACCACC ACCACCACTGATCTAGACT-3' (sequence ID No. 14) and the complementary 66 base strand were synthesized and purified using an Automated DNA Synthesizer 394 (Perkin-Elmer Japan Applied Biosystems). Both oligonucleotide preparations were mixed and incubated at 70° C. for 3 minutes and then were additionally warmed at 37° C. for 30 minutes to allow annealing. Subsequently, the terminals were phosphorylated using T4 polynucleotide kinase.

Figure 10:
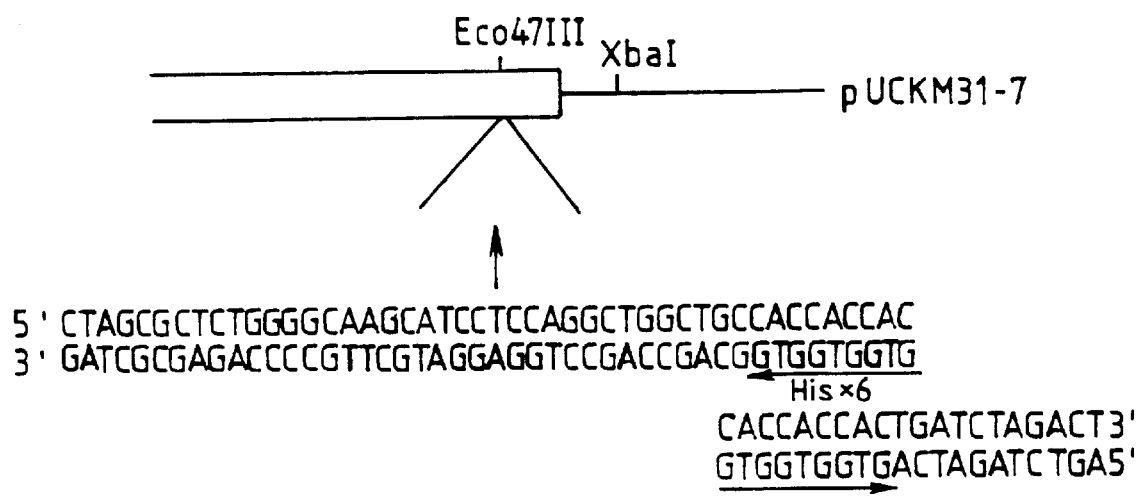
FIG. 10 is a diagram of the introduction of a histidine hexamer encoding sequence into pUCKM31-7.

The resulting double-stranded (ds) fragment was ligated using T4 DNA ligase into pUCKM31-7 which had previously been digested with Eco47III. The construct is shown in FIG. 10. E coli DH5α was transformed with this DNA by the calcium chloride method and the resulting transformed strains were selected and screened to obtain pUCKM31-7His. It was confirmed that there were no abnormalities in the portion of pUCKM31-7His where the fragment was inserted by analyzing a portion of the relevant base sequence of this pUCKM31-7His.

A high-expression plasmid for COS-1 cells was then prepared by subcloning the insert of pUCKM31-7His into pcDL-SRα296.

pUCKM31-7His was digested with XbaI and HindIII, the fragments were purified and the terminals of the fragments were blunted using 1 unit of Klenow fragment in the presence of 2 mM DATP, 2 mM dCTP, 2 mM dGTP, 2 mM dTTP, 50 mM Tris-HCl (pH 7.2), 10 mM MgSO$_4$, 0.1 mM dithiothreitol and 50 µg/ml of BSA.

Meanwhile, the high expression vector pcDL-SRα296 was digested with PstI and KpnI and blunt-ended with a DNA blunting kit. The blunted fragment was then ligated into the blunted plasmid using T4 DNA ligase. The resulting plasmid was then used to transform *E. coli* DH5α. Transformants were then selected and screened. A strain in which the direction of cDNA transcription was identical to the direction of the SRα promoter was selected, and the plasmid of this strain was designated pSRα31-7His. COS-1 cells were transfected with the resulting plasmid pSRα31-7His and serum-free supernatant was obtained in a manner similar to that described in Example 11.

EXAMPLE 13

Purification and N-Terminal Amino Acid Sequence Analysis 600 ml of the supernatant obtained in Example 12 were subject to dialysis against 17 volumes of dialysis buffer at 4° C. for 15 hours. The buffer was replaced with a further 17 volumes of dialysis buffer and dialysis was continued at 4° C. for an additional 4 hours.

The dialyzed preparation was then subjected to affinity chromatography using FPLC (Fast Protein Polynucleotide Liquid Chromatography—Pharmacia) under the following conditions:

Column: 20 ml of ProBond™ Resin (Invitrogen) filled into XK16/20 (φ2.0×20 cm, Pharmacia)

Elution buffer:
  A) 20 mM phosphate buffer (pH 7.8) containing 200 mM imidazole, 0.5 M NaCl
  B) 20 mM phosphate buffer (pH 7.8) containing 300 mM imidazole, 0.5 M NaCl Flow rate: 1 ml/min Fraction solution: 5 ml/tube Elution conditions: After recovering 4 fractions with elution buffer A), 16 fractions were recovered with elution buffer B), and the fractions were numbered in order from 1 to 20.

300 µl of each of the resulting fraction samples were taken and separately treated subjected to TCA precipitation treatment and the resulting precipitate was prepared and subjected to SDS-PAGE using a 12.5% gel under reducing conditions as before. Bands were detected by the silver stain method and three bands were detected centering around fraction no. 10. The existence of 3 bands indicates that the pSRα31-7His insert encodes a polypeptide having 3 different lengths with different N-terminal sequences.

The remainder of fractions 7 to 14 was concentrated by TCA precipitation and the precipitate was subjected to SDS-PAGE using a 10% gel under reducing conditions. The protein bands were then transferred from the polyacrylamide gel onto a polyvinylidine difluoride (PVDF) film (ProBlot™, Applied Biosystems) using a gel membrane transfer device (Marisol, KS-8441) operating at 9 V in the presence of transfer buffer [0.02% SDS, 20% methanol, 25 mM Tris-Borate (pH 9.5)] at 4° C. for 2.5 hours.

After this time, the membrane was stained with 0.2% naphthol blue black (Sigma), and the three bands corresponding to those previously identified were excised from the membrane, and the sequence of each band was determined to the 6th amino acid from the N-terminal using a gas phase protein sequencer (Shimadzu, PPSQ-10). The N terminal of the band with the second largest apparent molecular weight (molecular weight about 60,000) was as follows:

Val-Val-Phe-Val-Lys-Gln (amino acid nos. 1 to 6 of sequence ID no. 12)

These six amino acids correspond to the first six amino acids of the ORF from clone 31-7 and also correspond to the sequence of six amino acids starting from the 24th amino acid (val) from the N terminal of the precursor polypeptide encoded by the cDNA inserts of pSRα31-7His and pSRα31-7. Accordingly, deletion of amino acid numbers 1 to 23 from the N terminal of this precursor polypeptide should result in the secretion of a mature form of the protein starting with a Val residue.

EXAMPLE 14

Determination of Reducing Activity i) Construction of an Expression Vector

The polypeptide purified in the previous Examples was only obtainable in extremely small amounts as it was expressed from COS-1 cells. It was not, therefore, possible to use the polypeptide for other purposes, such as activity assays. Accordingly, it was necessary to find a way to express the polypeptide encoded by the cDNA insert of pSRα31-7 in an alternative host permitting production of suitable quantities for purification and assaying. To achieve this, the following procedure was performed.

pUCKM31-7 was digested with HindIII, the 3003 bp fragment containing the cDNA insert was isolated and purified and the terminals were blunted using a DNA blunting kit. The fragment was then further digested with XbaI.

Figure 11:
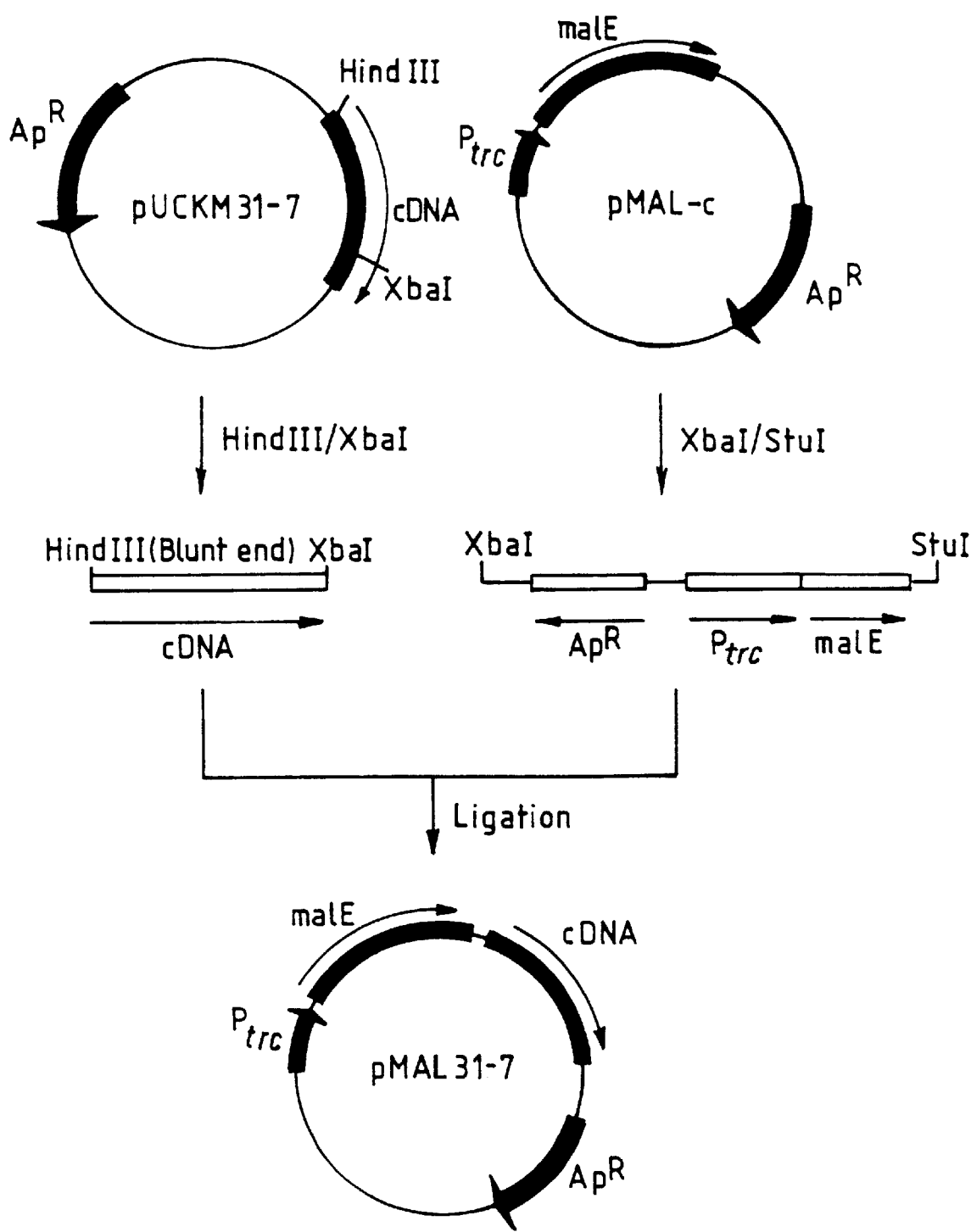
FIG. 11 is a construction diagram of pMAL31-7.

The expression vector pMAL-c [Guan, C. et al. (1987) Gene 67, 21–30] was digested with XbaI and StuI, and then the above XbaI-modified HindII fragment was ligated into this cleaved plasmid using T4 DNA ligase. The resulting construct is shown in FIG. 11. The construct was then used to transform *E. coli* TB-1 and Amp$^R$ transformants were selected and screened. A strain in which the direction of cDNA transcription was identical to the direction of the promoter was selected, and the plasmid thus obtained was designated pMAL31-7.

ii) Expression and Purification of Fusion Protein

A seed culture of *E. coli* harboring pMAL31-7 was prepared by culturing with shaking overnight at 37° C. in 3 ml of LB medium containing 50 µg/ml of ampicillin. The following day, 1 ml of the seed culture was added to 100 ml of fresh LB culture medium containing 50 µg/ml of ampicillin and cultured with shaking at 37° C. until the OD$_{600nm}$ reached 0.5. At this stage, IPTG was added to the culture to a final concentration of 0.1 mM, and the culture broth was further cultured with shaking overnight at 37° C.

The following day, bacterial cells were recovered from the overnight culture by centrifuging at 6500 rpm for 20 minutes at 4° C. The pellet was then suspended in 10 ml of column buffer and the cells in the resulting suspension were disrupted by treating with an ultrasonic disintegrator. Whole cells and cell fragments were then removed by centrifuging at 8800 rpm for 30 minutes at 0° C., and the soluble protein fraction was recovered as the supernatant. 1 ml of this soluble fraction was then subjected to chromatography on an amylose resin column (New England Biolabs).

The elution buffer for the chromatography was prepared by adding maltose to 10 ml of the column buffer to a final concentration of 10 mM.

The negative control sample was also chromatographed. This negative control was prepared using a similar procedure, except that the pMAL-c vector was used without any cDNA insert. The reducing activity of the protein in the chromatography samples was then assayed.

iii) Determination of Reducing Activity

Figure 12A:
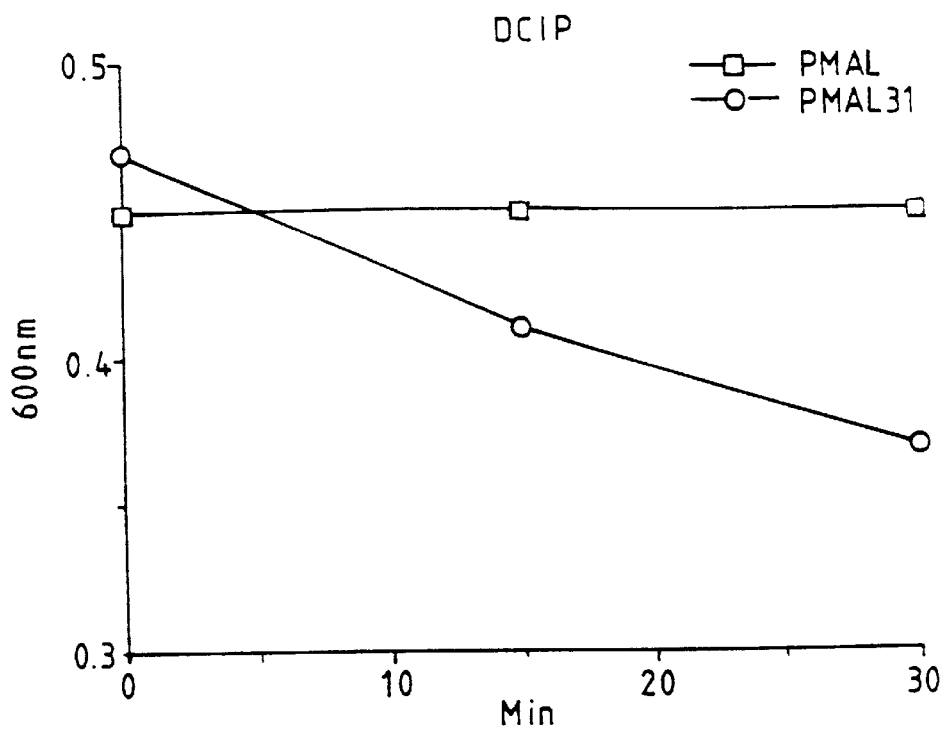
FIGS. 12A and 12B are graphs showing the results.
Figure 12B:
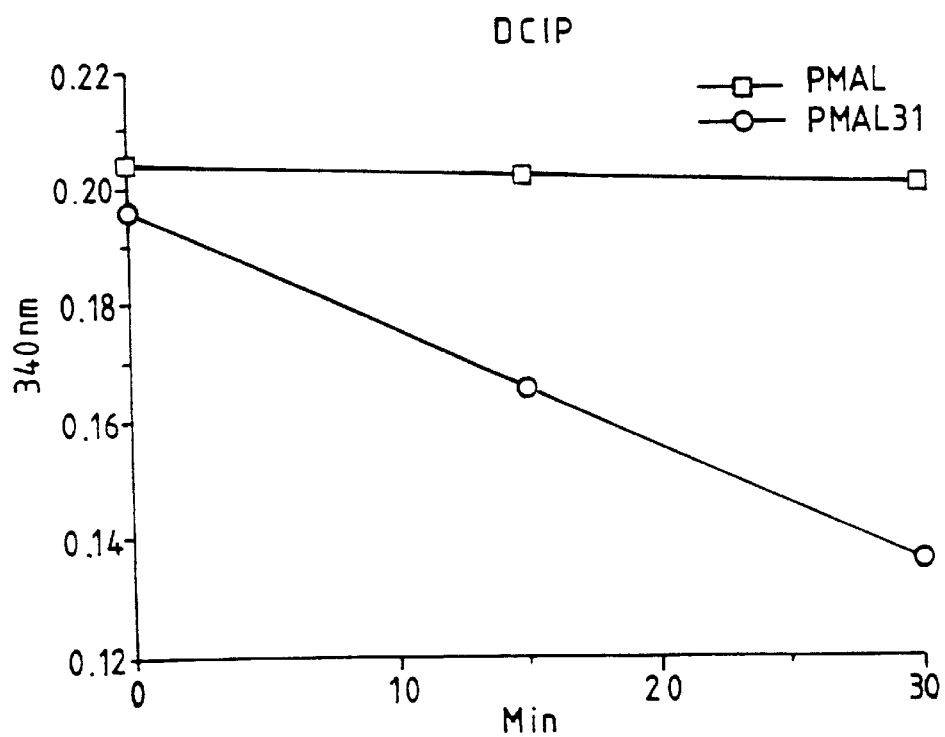
Figure 13:
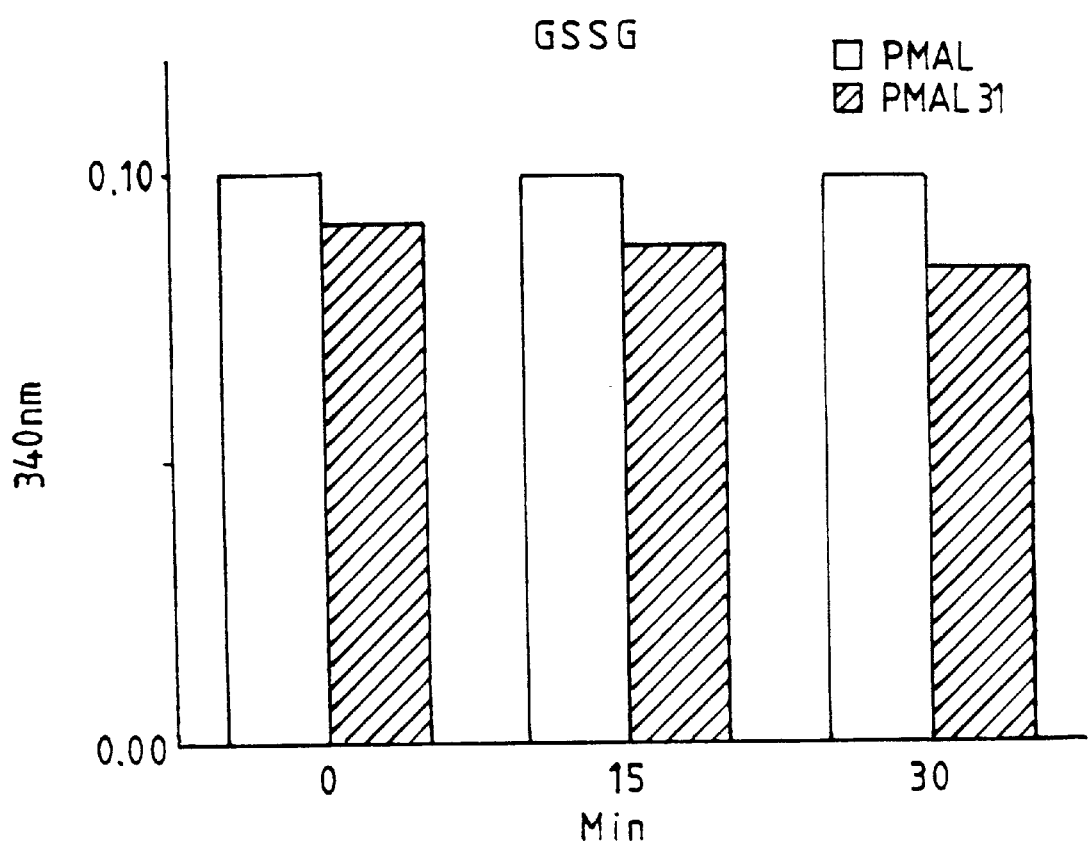
FIG. 13 is a determination of oxidized glutathione reducing activity.

Determination of reducing activity was performed in a cuvette (SARSTEDT, 10×4×45 mm) using dichlorophenol-indophenol (DCIP) and oxidized glutathione.

a) Determination of Reducing Activity Using DCIP 90.4 µg, as determined using the Protein Assay Kit (Bio-Rad), of each of the chromatography samples obtained in ii) above were separately mixed with 1 ml of 50 µM DCIP (Sigma). 15 µl of 1 mM NADPH (Boehringer-Mannheim) were then added to each of the samples and the $OD_{600nm}$ and $OD_{340nm}$ absorbance values were monitored with time. The resulting decrease in absorbance at both wavelengths is shown in FIG. 12, and it can be seen that only the pMAL31-7 sample contains a factor that reduces DCIP.

b) Determination of Reducing Activity Using Oxidized Glutathione 15 ml of 10 mM oxidized glutathione (Boeringer-Mannheim) were added to 90.4 µg of each of the chromatography samples obtained in ii) above and which had previously been loaded into separate cuvettes. 15 µl of 1 mM NADPH were added to each cuvette, and the absorbance at $OD_{340nm}$ was monitored with time. The results are shown in FIG. 13, and it can be seen that only the protein from the pMAL31-7 sample is capable of reducing oxidized glutathione. It was also observed that there is no consumption of NADPH when no oxidized glutathione is present, so that it was concluded that the protein from the pMAL31-7 sample can only reduce oxidized glutathione in the presence of NADPH.

EXAMPLE 15

Purification and Analysis of N-Terminal Amino Acid Sequence

From Example 13, it was concluded that COS-1 cells transfected with pSRα31-7His expressed a polypeptide having three types of N-terminal.

In a separate experiment, rabbits were immunized with fusion protein recovered from *E. coli* transformed with pMAL31-7 to obtain a polyclonal antibody preparation against KM31-7 protein. Western blotting was performed using this polyclonal antibody, and it was clear that three types of bands are also detected in the serum-free culture supernatant obtained from COS-1 cells transfected with pSRα31-7. This result is similar to that obtained in Example 13.

Accordingly, COS-1 cells were transfected with pSRα31-7 with the aim of collecting of a large volume of serum-free culture supernatant to allow purification and analysis of the N-terminal sequence of the KM31-7 protein.

COS-1 cells were transfected with pSRα31-7 and were cultured for 3 days in 150 mm petridishes each containing 30 ml of DMEM. The culture supernatant was harvested after this time, and 30 ml of fresh medium were added to each dish and culture was continued for a further three days. Once again, the culture supernatant was harvested. Other aspects of the transfection and culture were as described in Example 11, but 199 dishes were cultured.

The harvested supernatants were pooled and 10 liters of serum-free culture supernatant were collected after centrifugation and this was dialyzed overnight against 10 mM Tris-HCl (pH 9.0). Ion exchange chromatography was then performed eight times on the dialyzed preparation under the following conditions using FPLC (Pharmacia):

Column: 20 ml of DEAE Sepharose Fast Flow (Pharmacia) filled into XK16/20 (φ2.0×20 cm, Pharmacia)

Elution buffers:
A) 10 mM Tris-HCl (pH 9.0)
B) 10 mM Tris-HCl (pH 9.0)–0.5 M NaCl Flow rate: 1 ml/min Fraction solution: 3 ml/tube Elution conditions: Elution buffer A changing over to Elution buffer B in a linear concentration gradient over a period of 60 minutes.

The fractions eluted at each NaCl concentration from 0.1 M to 0.4 M were collected and pooled, and dialyzed overnight against a dialysis buffer containing 0.1 M Tris-HCl, 5 mM EDTA (pH 7.6) and 1 mM 2-mercaptoethanol. The dialyzed preparation was then subjected to affinity chromatography using 2',5'-ADP Sepharose 4B (Pharmacia) under the following conditions:

Column: 20 ml of 2',5'-ADP Sepharose 4B filled into XK16/20 (φ2.0×20 cm, Pharmacia)

Elution buffers:
A) 0.1 M Tris-HCl, 5 mM EDTA (pH 7.6), 1 mM 2-mercaptoethanol
B) 0.1 M Tris-HCl, 5 mM EDTA (pH 7.6), 1 mM 2-mercaptoethanol, 10 mM NADPH Flow rate: 0.5 ml/min Fraction solution: 2 ml/tube Elution conditions: Elution buffer A changing over to Elution buffer B in a linear concentration gradient over a period of 120 minutes.

100 µl aliquots of each of the resulting fractions were precipitated with TCA and the precipitates were subjected to SDS-PAGE using a 12.5% gel under reducing conditions.

After electrophoresis, the gel was silver-stained to detect the protein bands. Three bands were obtained starting with fraction #11.

The whole of the remainder of fractions #11 to #14 were then concentrated by TCA precipitation and the precipitate was subjected to SDS-PAGE using a 12.5% gel under reducing conditions. The protein was then transferred from the gel to a ProBlot PVDF membrane (Applied Biosystems) following electrophoresis. After transfer of the protein to the membrane, the membrane was stained with 0.2% naphthol, blue black and the three proteinaceous bands were excised. N terminal sequence analysis was then performed using a gaseous phase protein sequencer.

The N terminal of the band apparently having the smallest molecular weight of the three types was determined to be Lys-Leu-Leu-Lys-Met. These five amino acids correspond to the five amino acids starting from the 49th amino acid from the N terminal of the polypeptide encoded by the cDNA insert of pSRα31-7. Accordingly, it was concluded that cleavage of the peptide at the 48th residue resulted in one mature form of the protein starting with an N-terminal Lys.

EXAMPLE 16

Preparation of a Monoclonal Antibody Against the KM31-7 Protein (a) Preparation of Antigen Protein A seed culture of *E. coli* harboring pMAL31-7 was prepared by culturing a loop of cells with shaking overnight at 37° C. in 3 ml of LB medium containing 50 µg/ml of ampicillin. 1 ml of the resulting seed culture was inoculated into 100 ml of fresh LB medium containing 50 µg/ml of ampicillin and this was cultured with shaking at 37° C. until the $OD_{600nm}$ reached 0.5. At this stage, IPTG was added to the culture broth a final concentration of 0.1 mM which was then further cultured with shaking overnight at 37° C.

Cells were recovered from the resulting overnight culture by centrifugal separation at 6500 r.p.m. for 20 minutes at 4° C., and the pellet was suspended in 10 ml of column buffer. The cells in the resulting suspension were disrupted using an ultrasonic disintegrator and the resulting liquid was centrifuged at 8,000 r.p.m. and at 0° C. for 30 minutes. The resulting supernatant contained the soluble protein fraction.

This soluble protein fraction was subjected to chromatography on a 1 ml amylose resin column. Elution was performed with 10 ml of column buffer containing 10 mM of maltose. The fusion protein obtained from the chromatography was then stored and subsequently used as the antigen.

(b) Preparation of Immunized Mice Spleen Cells 2 ml of Freund's complete adjuvant was added to 2 ml of the antigen (equivalent to 200 µg) purified in a) above to form an emulsion. This emulsion was taken up in a 5 ml syringe barrel equipped with a glass junction, and the emulsion was used to immunize 8 week-old, male BALB/c mice by subcutaneous injection.

Starting with the second round of immunization, Freund's incomplete adjuvant was used as the adjuvant, but following the same procedure as with the first immunization. Immunization was performed four times altogether, at a rate of one immunization roughly every 2 weeks.

Starting with the second immunization, blood was sampled from the venous plexus of the fundus oculi immediately before immunization, and the titer of anti-KM31-7 antibody in the serum was determined by solid-phase, enzyme-linked immunosorbent assay (ELISA).

Solid Phase Anti-KM31-7 ELISA

Between 150 and 200 µl (corresponding to about 200 ng of fusion protein) of the serum-free culture supernatant obtained from COS-1 cells transfected with pSRα31-7 were placed in each well of a 96 well ELISA plate (Costar) for use as the antigen. The plate was then allowed to stand overnight at 4° C. to coat the bottom surfaces of the plate wells. The following day, the plate was washed 3 times with 0.1% Tween 20/phosphate buffered saline (0.1% Tween 20/PBS) and then each well was loaded with 100 µl of BSA prepared to 10 µg/ml with PBS and allowed to stand at room temperature for 1 hour.

After this time, the plate was washed for a further three times with 0.1% Tween 20/PBS. 30–100 µl of primary antibody in the form of a serially diluted sample (for example, mouse serum, hybridoma culture supernatant or monoclonal antibody) were loaded into each well, and the plate was allowed to stand at room temperature for 1 hour.

After this time, the plate was again washed three times with 0.1% Tween 20/PBS and then 100 µl of secondary antibody was added to each well. The secondary antibody was prepared as a 3000-fold dilution solution of goat anti-mouse IgG-peroxidase complex (Amersham) or a 3000-fold dilution solution of goat anti-mouse IgG alkaline phosphatase complex (BIO-RAD). The plate was then allowed to stand at room temperature for 1 to 2 hours.

After this time, the plate was again washed three times with 0.1% Tween 20/PBS, and then 100 µl of either peroxidase substrate solution (BIO-RAD, Peroxidase Substrate Kit ABTS) or 10% diethanolamine containing 0.001% paranitrophenyl phosphate solution were added to each well. The plate was then allowed to stand at room temperature for 15 to 30 minutes, whereafter the antibody titer could be calculated by measuring the absorbance at 415 nm or 405 nm using a microplate reader (BIO-RAD).

(c) Preparation of Mouse Myeloma Cells

8-Azaguanine-resistant mouse myeloma cells P3-X63-Ag8.653 (653) (ATCC no. CRL-1580) were cultured in a normal medium (complete GIT) to obtain a minimum of $2 \times 10^7$ cells.

(d) Preparation of Hybridoma $1.4 \times 10^8$ immunized mouse spleen cells obtained after the immunization regimen described in b) above were thoroughly washed with DMEM (Nissui Pharmaceutical). The washed cells were then mixed with $1.5 \times 10^7$ mouse myeloma cells P3-X63-Ag8.653 (653) prepared in c) above, and the resulting mixture was centrifuged at 800 r.p.m. for 6 minutes.

The cell group, consisting of a mixture of the spleen cells and P3-X63-Ag8.653 (653) cells, was collected as the pellet and was broken up. Polyethylene glycol 4000 (polyethylene glycol #4000) as a 50% solution with DMEM was prepared in advance, and this solution was dripped onto the broken up cells over a period of 1 minute with stirring at a rate of 2 ml/min. DMEM was then added to the cell preparation in a similar manner for 1 minute at a rate of 2 ml/min. This procedure was repeated one more time for both of the polyethylene glycol and DMEM solutions. Finally, 16 ml of DMEM was added gradually over a period of 3 minutes. The resulting cell preparation was then centrifuged at 800 r.p.m. for 6 minutes. The resulting supernatant was discarded and the cells were suspended in 35 ml of complete GIT containing 5 to 10 ng/ml of mouse IL-6.

(e) Screening of Hybridomas 100 l of the suspension prepared in d) above were loaded into each well of a 96 well plate (Sumitomo Bakelite) which was then cultured at 37° C. in a 7.5% $CO_2$ incubator. After 7 days of incubation, 50 µl of HAT medium were added to each well. After a further 4 days of incubation, another 50 µl of HAT medium were added to each well. The plate was then incubated for 3 more days. After this time, a portion of the culture supernatant was sampled from wells in which colony growth of fused cells could be observed, and the titer of anti-KM31-7 antibody was assayed by the solid-phase ELISA described in b) above. Sampled medium was immediately replaced with HT medium.

(f) Cloning

Cloning of cells from wells testing as positive was repeated three times by limiting dilution analysis. Those clones observed to have a consistent antibody titer were selected for use as anti-KM31-7 monoclonal antibody-producing hybridoma cell lines. At this stage in particular, ELISA was performed not only as described in b) above, but also a control ELISA was performed using the serum-free culture supernatant obtained from COS-1 cells transfected with pcDL-pSRα296 to prepare the solid phase. Accordingly, those cell lines that reacted to the former but did not react to the control ELISA were selected for cloning.

(g) Purification of Monoclonal Antibody

Culture supernatant from the anti-KM31-7 monoclonal antibody-producing hybridoma cell line was collected, filter sterilized with a 0.22 µm filter (Millipore), and then the antibody was purified using MAbTrap GII (Pharmacia).

(h) Assaying the Monoclonal Antibody

1) Antigen Specificity of the Monoclonal Antibody

Monoclonal antibodies were confirmed to be specific for KM31-7 protein by the immune precipitation test using the serum-free culture supernatant obtained from COS-1 cells transfected with pSRα31-7.

2) Classification of the Monoclonal Antibody

This test was performed using a mouse monoclonal antibody isotyping kit (Amersham), and the antibody was identified as belonging to the IgG1 subclass.

EXAMPLE 17

Isolation and Purification of EM31-7 Protein Using an Antigen-Antibody Reaction

This was performed as described in Example 16 h) 1) above. The same test was also repeated using the antibody and serum-free supernatant obtained from COS-1 cells transfected with pcDL-pSRα296.

1.4 µg of monoclonal antibody was added to 1.7 ml of each of the serum-free supernatants and allowed to react at room temperature for 1 hour while centrifuging at 20 r.p.m. in 2.2 ml microcentrifuge tubes. The control was performed using serum-free supernatant obtained from COS-1 cells transfected with pSRα31-7 but without adding monoclonal antibody.

30 µl of Protein G Sepharose 4 Fast Flow (Pharmacia), which had previously been washed with 0.1% Tween 20/PBS, were added to each tube to adsorb the antibody and centrifuging was continued at a speed of 20 r.p.m. for 30 minutes at room temperature.

After this time, each mixture was centrifuged for several seconds at 10000 r.p.m. in a microcentrifuge, and then the supernatant was carefully discarded so as not to lose any of the sediment. The pellets were then individually washed with 0.1% Tween 20/PBS and then microcentrifuged and washed in a similar manner a further 5 times.

The resulting sediment was suspended in SDS-PAGE sample buffer sulution containing 10 µl of 2-mercaptoethanol. Each suspension was heated at 90° C. for 2 minutes, and then SDS-PAGE was performed under reducing conditions using a 12.5% gel. Following electrophoresis, the product was transferred from polyacrylamide gel to a nitrocellulose film (BIO-RAD). Western blotting was performed using the polyclonal anti-KM31-7 antibody described in Example 1, part (a) and the anti-KM31-7 monoclonal antibody was determined to specifically precipitate KM31-7 protein from COS-1/pSRα31-7 serum-free culture supernatant.

EXAMPLE 18

Preparation of CYVV-NIa/KM31-7 Fusion Protein

In order to express KM31-7 protein using the CYVV-NIa protease technique, it is necessary to link the 3' terminal of the NIa gene in the same ORF as the KM31-7 protein DNA. Accordingly, the following two-stage procedure was performed.

i) Introduction of the 3' Side Chain (SmaI-XbaI. 1006 bp) of KM31-7 cDNA into pKSUN9

In order to obtain a SmaI-XbaI fragment (1,006 bp) containing the 3' end of KM31-7 cDNA, 7 µg of pSRα31-7 plasmid DNA were digested with the restriction enzymes SmaI and XbaI, and the resulting fragment was collected and purified using GENECLEAN II. (Funakoshi Japan) using a 0.8% agarose gel.

Meanwhile, 5 µg of pKSUN9 plasmid DNA were similarly digested with SmaI and XbaI, and the cleavage fragment was dephosphorylated with bovine alkaline phosphatase (Alkaline Phosphatase E. coli C75, Takara Shuzo, Japan). The resulting dephosphorylated, linearized DNA was ligated with the SmaI-XbaI KM-31 fragment using a ligation kit (Takara Shuzo), and the resulting construct was used to transform E. coli strain JM109. Transformants were selected and screened to obtain a clone pNIa31-7SX containing a SmaI-XbaI fragment.

ii) Linking of NIa Protease and KM31-7

In order to link the C terminal sequence of NIa with the N-terminal sequence of the KM31-7 sub-type having a Val N-terminal residue in the same reading frame, four types of polymerase chain reaction (PCR) primers were constructed, using a Perkin-Elmer Japan Applied Biosystems Model 392 DNA Synthesizer. The primers are as follows:

```
5' GGT CAG CAC AAA TTT CCA 3'            (1)

5' AAA CAC AAC TTG GAA TGA ACA ATT 3'    (2)

5' TCA TTC CAA GTT GTG TTT GTG AAA 3'    (3)

5' CAT AGG ATG CTC CAA CAA 3'            (4)
```

The first round of PCR was carried out by using 1 µg of pKSUN9 plasmid DNA as the template. 100 pmol each of primers (1) and (2) and 1/10 volume of 10-fold concentration Taq polymerase reaction buffer solution and finally 5 units of Taq polymerase (Takara Shuzo) were added to the reaction solution, in that order. The PCR reaction was first carried out at 72° C. for 3 minutes, followed by 30 cycles of: 94° C. for 1 minute, 55° C. for 2 minutes and 72° C. for 3 minutes, and finishing with a treatment at 72° C. for 10 minutes. Following the PCR reaction, the enhanced DNA product was subjected to 8% polyacrylamide gel electrophoresis. Strips of gel containing DNA were identified by ethidium bromide staining and broken up. 300 µl of elution buffer (0.5 ammonium acetate, 1 M- EDTA, pH 8.0) were added to each of the crushed strips and incubated at 37° C. overnight. Centrifuging yielded the supernatant containing the purified and amplified DNA.

PCR was once again performed in a similar fashion but using 1 µg of pUCKM31-7 plasmid DNA as the template and using primers (3) and (4), and the resulting DNA was purified as above.

The amplified fragment from the first PCR contained the sequence encoding the residues from the N terminal of KM31-7 protein, starting with Val-Val-Phe, through to 31 bp upstream from the XhoI site of NIa. The amplified fragment from the second PCR contained the sequence coding for Asn-Cys-Ser-Phe-Gln from the C terminal of NIa through to 32 bp downstream from the SmaI site of KM31-7 cDNA.

Accordingly, when PCR is performed using both DNA fragments resulting from the two PCR's along with primers (1) and (4), the result is a hybridized strand consisting of 9 bp of the 3' terminal of NIa and 15 bp of the sequence encoding the desired N-terminal of KM31-7. Thus, it is possible to generate a fused DNA sequence with this portion as the link.

As a result of this logic, the second round of PCR was performed in just this manner, and the enhanced fragment was collected from the gel.

iii) Introduction of NIa/KM31-7 DNA into pNIa31-7SX

5 µg of the pNIa31-7SX plasmid DNA obtained in i) was digested with XhoI and SmaI, and the resulting DNA was dephosphorylated by treatment with bovine alkaline phosphatase. The PCR product prepared in ii) was also digested with XhoI and SmaI and the resulting fragment was then ligated with the digested, dephosphorylated pNIa31-7SX using a ligation kit. The resulting construct was used to transform E. coli strain JM109.

Amp$^R$ transformants. were then selected and screened. Screening was effected by digesting with XhoI followed by electrophoresis. Clones having only an 8.0 kbp band were selected. The plasmids of the selected clones were then digested with HindIII and again electrophoresed. The plasmid which was selected had a 330 bp band corresponding to part of the NIa cDNA insert. This plasmid was designated pNIa31-7V, and contained the XhoI and SmaI PCR product.

The base sequence of clone pNIa31-7V was determined, and it was confirmed that the sequences encoding NIa and KM31-7 were linked in the same ORF, with the necessary Gln-Val cleavage sequence located between NIa and the KM31-7 ptotein.

iv) Production of KM31-7 Protein

Western blotting confirmed that pNIa31-7V was functioning in *E. coli* and that the KM-31-7 protein was being expressed by the constructed recombinant gene.

A seed culture of *E. coli* harboring the plasmid pNIa31-7V was cultured overnight with shaking in 3 ml of LB medium containing 50 µg/ml of ampicillin. One ml of the seed culture was added to 100 ml of fresh LB medium containing 50 µg/ml of ampicillin and cultured at 37° C. with shaking until the $OD_{600nm}$ reached 1.0. At this stage, IPTG was added to the culture broth to a final concentration of 1 mM, and the culture was then incubated at 28° C. for two further nights with shaking.

After this time, 1 ml of the culture was transferred to a microcentrifuge tube and centrifuged for 5 minutes at 15000 rpm. The supernatant was discarded and the pellet was mixed with 300 µl of sterile water and 300 µl of SDS-PAGE sample buffer solution containing 2-mercaptoethanol to break up the settled cell bodies. The resulting suspension was heated at 95° C. for 2 minutes and then 10 µl of this suspension were subjected to SDS-PAGE on an 8% gel under reducing conditions.

After electrophoresis, the protein was transferred from the gel onto a nitrocellulose membrane. This was achieved by contacting the gel with the membrane and incubating in the presence of a transcription buffer solution (25 mM Tris-HCl, 1.4% glycine and 20% methanol) at 4° C. for 2.5 hours and at 19 V using a gel membrane transcription apparatus (Marisol Japan).

The nitrocellulose membrane was then washed with 20 ml of PBS-T medium, and then blocking was performed for 1 hour in 20 ml of PBS-T containing 5% skim milk (Snow Brand Co., Ltd). After this time, the membrane was rinsed with two lots of 20 ml of PBS-T and then allowed to react for 90 minutes in 20 ml of PBS-T containing 1 µl of 100-fold diluted anti-KM31-7 rabbit MAb serum (primary antibody) in sterile water. The nitrocellulose film was then rinsed once for 15 minutes and then twice for 5 minutes each with 20 ml of PBS-T.

The washed membrane was then placed in a bath of 3,000-fold diluted peroxidase-labelled anti-rabbit IgG goat antibody (BIO-RAD) in PBS-T (used as the secondary antibody above), and allowed to stand for 1 hour. The membrane was then washed with 20 ml of PBS-T and transferred into a bath of ECL detection reagent (Amersham), and the bands that reacted with anti-KM31-7 antibody were detected by autoradiography.

Western blotting was performed and a band having a molecular weight of roughly 60,000 was detected. This band demonstrated the same mobility as the protein having the second largest molecular weight of the three KM31-7 proteins detected from the serum-free culture supernatant obtained by transfecting COS-1 cells with pSRα31-7 used as the control.

Media x M Phosphate Buffer

An x M solution of $Na_2HPO_4$ adjusted to the desired pH using an x M solution of $NaH_2PO_4$.

Inoculation Buffer 0.1 M Tris-HCl buffer, pH 7.0, 0.05 M EDTA, 1% 2-mercaptoethanol.

Extraction Buffer 0.1 M Tris-HCl buffer, 0.05 M EDTA, 1% 2-mercaptoethanol, pH 7.0.

Degradation Solution 200 mM ammonium carbonate, 2% SDS, 2 mM EDTA, 400 µg/ml bentonite and 20 µg/ml protease K (pH 9.0).

1×SSC 0.15 M NaCl, 0.015 M trisodium citrate, pH 7.0.

Liquid LB Medium 10 g of Bacto Tryptone (Difco), 5 g of Bacto yeast extract (Difco) and 5 g of sodium chloride, all made up to 1 liter with distilled water.

Tris-Calcium Buffer 10 mM Tris, 50 mM calcium choride, adjusted to pH 7.4 with hydrochloric acid.

Lysis Buffer 0.17 g of sucrose, 250 µl of 1 M Tris-HCl buffer (pH 8.0), 200 µl of 0.5 M EDTA (pH 8.0), made up to 20 ml with redistilled water.

Alkaline-SDS Solution 0.2 M sodium hydroxide, 1% SDS.

TBE Solution 100 mM Tris, 100 mM boric acid, 1 mM EDTA.

Denaturation Solution 1.5 M sodium chloride, 0.5 M sodium hydroxide.

Neutralization Buffer 0.5 M Tris, 3 M sodium chloride (pH 7.4).

50×Denhardt's Solution

1% polyvinyl pyrrolidone, 1% bovine serum albumin, 1% Ficoll 400. This solution is then diluted with redistilled water, as appropriate, to achieve the desired concentration 5×Denaturation Buffer 125 µl of 1 M glycine (pH 9.0), 25 µl of 1 M magnesium chloride, 850 µl of redistilled water.

5×Labelling Buffer

25 µl of 1 M Tris-HCl buffer (pH 7.9), 5 µl of 1 M magnesium chloride, 2.5 µl of 1 M dithiothreitol, 9.2 µl of redistilled water.

10×M9 Salt Solution 0.145 M disodium hydrogenphosphate, 0.172 M potassium dihydrogenphosphate, 0.187 M ammonium chloride, 0.137 M sodium chloride, pH 7.0.

M9 Minimum Agar Medium 10 ml of 10× M9 salt solution, 100 µl of 1 M magnesium sulfate, 1 ml of 20% glucose, 50 µl of 1% thiamine hydrochloride salt, 1 ml of 0.01 M calcium chloride and 13 ml of redistilled water, all mixed, sterilized by filtration, and then poured onto plates immediately after the addition of 50 ml of 3% bactoagar.

Liquid SOB Medium 10 g of bactotryptone, 2.5 g of bactoyeast extract, 100 µl of 5 M sodium chloride and 125 µl of 1 M potassium chloride are mixed and made up to 500 ml with distilled water. After autoclaving, 5 ml of 1 M magnesium chloride and 5 ml of 1 M magnesium sulfate are added.

TFB1 Buffer 5 ml of 1 M 2-(N-morpholino)ethanesulfonic acid (MES-adjusted to pH 6.2 with 1 N HCl), 6.045 g of rubidium chloride, 0.735 g of calcium chloride bihydrate and 4.94 g of manganese chloride tetrahydrate mixed, adjusted to pH 5.8 with glacial acetic acid, made up to 500 ml with redistilled water and sterilized by filtration.

TFB2 Buffer 1 ml of 1 M 2-(N-morpholino)propanesulfonic acid (MOPS), 1.102 g of calcium chloride bihydrate, 0.12 g of rubidium chloride and 15 ml of glycerol mixed, adjusted to pH 6.5 with glacial acetic acid, made up to 100 ml with redistilled water and sterilized by filtration.

Liquid SOC Medium 5 ml of liquid SOB Medium, 90 µl of 20% glucose.

2×YT Medium 16 g of bactotryptone, 5 g of bactoyeast extract and 5 g of sodium chloride mixed and made up to 1 liter with redistilled water.

PBS-Tw Medium 80 mM disodium hydrogen- phosphate, 20 mM sodium dihydrogenphosphate, 100 mM sodium chloride, 0.1% Tween 20.

PBS-T Medium 4 g of sodium chloride, 0.1 g of potassium dihydrogenphosphate, 1.45 g of disodium hydrogenphosphate dodecahydrate, 0.1 g of potassium chloride and 0.1 g of sodium azide, all made up to 1 liter with redistilled water, pH 7.4.

Alkaline Phosphatase Substrate Solution 0.01% p-nitrophenyl phosphate dissolved in 10% aqueous diethanolamine solution which had been adjusted to pH 9.8 with hydrochloric acid.

Medium A

DMEM (Dulbecco's modified Eagle medium, containing 4.5 g/l of glucose), 10% inactivated fetal bovine serum (manufactured by Hyclone) and 10 mM HEPES (pH 7.2).

Medium B

DMEM (containing 4.5 g/l of glucose), 10 mM HEPES (pH 7.2), 3% inactivated fetal bovine serum, 5 µg/ml bovine insulin (manufactured by Sigma), 8 µg/ml d-biotin (manufactured by Sigma), 4 µg/ml pantothenic acid (manufactured by Sigma), 1.0 µM dexamethasone (manufactured by Sigma) and 0.5 mM isobutylmethylxanthine (manufactured by Aldrich).

Medium C

DMEM (containing 4.5 g/l of glucose) containing 5% inactivated fetal bovine serum, 10 mM HEPES (pH 7.2) and 100 ng/ml bovine insulin.

Medium D

DMEM (containing 4.5 g/l of glucose), 5% inactivated fetal bovine serum, 10 mM HEPES (pH 7.2), 100 ng/ml bovine insulin and 10 U/ml sodium heparin (manufactured by Novo Industry Co.).

LPL Substrate Solution 13 mM glycerol tri[9,10(n)-$^3$H]oleate (51.8 KBq/µmol, manufactured by Amersham), 1.3 mg/ml L-α-phosphatidylcholine distearoyl (manufactured by Sigma Co.), 20 mg/ml bovine serum albumin (manufactured by Sigma Co.), 135 mM Tris hydrochloride [Tris-HCl (pH 8.1), manufactured by Sigma Co.], 16.5% (v/v) glycerol and 16.5% (v/v) inactivated fetal bovine serum.

Guanidine Thiocyanate Solution

4 M guanidine thiocyanate, 1% Sarkosyl, 20 mM ethylenediamine tetraacetic acid (EDTA), 25 mM sodium citrate (pH 7.0), 100 mM 2-mercaptoethanol and 0.1% antifoam A (Sigma).

Adsorption Buffer 0.5 M NaCl, 20 mM Tris-HCl (pH 7.5), 1 mM EDTA and 0.1% SDS.

Eluting Solution 10 mM Tris-HCl (pH 7.5), 1 mM EDTA and 0.05% SDS.

Reverse Transcriptase Reaction Solution of Example 2

50 ml Tris-HCl (pH 8.3), 8 mM $MgCl_2$, 30 mM KCl, 0.3 mM dithiothreitol, 2 mM dATP, 2 mM dGTP, 2 mM dTTP, 10 µCi [α-$^{32}$P]dCTP and 1.4 µg of vector primer-DNA (3'-oligo(dT)-tailed pcDV-1, Pharmacia).

Terminal Transferase Reaction Solution 140 mM potassium cacodylate, 30 mM Tris-HCl (pH 6.8), 1 mM $CoCl_2$, 0.5 mM dithiothreitol, 0.2 µg of poly A and 100 mM dCTP.

Restriction Enzyme Buffer 50 mM NaCl, 10 mM Tris-HCl (pH 7.5), 10 mM $MgCl_2$ and 1 mM dithiothreitol.

10-Volume Ligase Buffer 10 mM ATP, 660 mM Tris-HCl (pH 7.5), 66 mM $MgCl_2$ and 100 mM dithiothreitol.

Electrophoresis Pigment

50% glycerol, 0.01 M disodium hydrogen phosphate (pH 7.0) and 0.4% bromophenol blue.

1×TAE 0.04 M Tris-acetate, 0.001 M EDTA.

1×SSCP 120 mM NaCl, 15 mM sodium citrate, 13 mM potassium dihydrogen phosphate and 1 mM EDTA.

Reverse Transcriptase Reaction Solution of Example 6

1×first strand synthesis buffer, 5% sodium pyrophosphate, 100 units of ribonuclease inhibitor, 1 mM dATP, 1 mM dGTP, 1 mM dTTP, 0.5 mM dCTP and 3.75 µg of oligo(dT) primer, all provided with the cDNA Cloning System (Amersham).

SM Buffer 100 mM NaCl, 8 mM $MgSO_4 \cdot 7H_2O$, 50 mM Tris-HCl (pH 7.5) and 0.01% gelatin.

Dialysis Buffer 20 mM phosphate buffer (pH 7.8) and 0.5 M NaCl.

Column Buffer 10 mM Tris-HCl (pH 7.4), 200 mM NaCl and 1 mM EDTA.

Taq Polymerase Reaction Buffer Solution

Taq containing 500 mM Tris-HCl (pH 8.3), 500 mM KCl, 15 m $MgCl_2$, 100 mM dATP, 100 mM dCTP, 100mM dGTP, 100 mM dTTP and 2 mg/ml of gelatin.

What is claimed is:

1. An isolated polynucleotide sequence encoding a fusion protein and comprising, in the 5' to 3' direction and in the same open reading frame:
   (a) a sequence encoding the clover yellow vein virus Nuclear Inclusion a protein;
   (b) a sequence encoding a cleavage peptide recognizable by and cleavable by said clover yellow vein virus Nuclear Inclusion a protein; and (c) at least one sequence encoding an exogenous polypeptide, wherein said sequence does not encode a protein or peptide as set forth in (a) or (b).

2. The polynucleotide sequence of claim 1, which is DNA.

3. The polynucleotide sequence of claim 2, which is in the form of a double strand.

4. An antisense polynucleotide sequence corresponding to the polynucleotide sequence of claim 1.

5. The polynucleotide sequence of claim 1, in which the sequence of (c) encodes more than one polypeptide and there are encoded further cleavage sequences between each encoded polypeptide.

6. The polynucleotide sequence of claim 5, in which said further cleavage sequences are recognizable by clover yellow vein virus Nuclear Inclusion a protein.

7. The polynucleotide sequence of claim 1, wherein the sequence of (c) encodes only one polypeptide.

8. The polynucleotide sequence of claim 1, in which the sequence of (b) is wholly or partly comprised in either or both of the sequences (a) and (c).

9. The polynucleotide sequence of claim 8, in which the sequence of (b) is wholly comprised in the sequences of (a) and (b).

10. The polynucleotide sequence of claim 1, wherein there are encoded one or more amino acid residues between the cleavage peptide encoded by the sequence of (b) and the polypeptide encoded by the sequence of (c).

11. The polynucleotide sequence of claim 1, in which cleavage of the fusion protein by the Nuclear Inclusion a protein encoded by the sequence of (a) yields a polypeptide having an additional N-terminal amino acid sequence of which the terminal residue is a residue of glycine, serine or alanine.

12. The polynucleotide sequence of claim 1, in which cleavage of the fusion protein by the Nuclear Inclusion a protein encoded by the sequence of (a) yields a polypeptide having an additional N-terminal amino acid sequence of which the terminal residue is a residue of glycine, serine or alanine, said residue being removable by the action of an aminopeptidase.

13. The polynucleotide sequence of claim 1, in which a proline residue is encoded between the N-terminal of the polypeptide and the C-terminal of the cleavage peptide.

14. The polynucleotide sequence of claim 1, in which a proline residue is encoded between the N-terminal of the polypeptide and the C-terminal of the cleavage peptide, thereby permitting the cleavage of any amino acid residues that are adjacent to and N-terminal to said proline residue by the action of aminopeptidase P (EC 3.4.11.9).

15. The polynucleotide sequence of claim 14, in which, after cleavage up to the the proline residue, the proline residue can then be removed by the action of proline iminopeptidase (EC 3.4.11.5).

16. The polynucleotide sequence of claim 1, in which an alanine residue is encoded between the N-terminal of the polypeptide and the C-terminal of the cleavage peptide.

17. The polynucleotide sequence of claim 1, in which an alanine residue is encoded between the N-terminal of the polypeptide and the C-terminal of the cleavage peptide, thereby permitting the cleavage of any amino acid residues between the C-terminal of the cleavage peptide and said alanine residue by the action of aminopeptidase P (EC 3.4.11.9), and cleavage of the alanine residue by the catalytic action of alanine aminopeptidase (EC 3.4.11.14).

18. The polynucleotide sequence of claim 1, wherein the sequence of (a) is given by nucleotide numbers 10 to 1311 in SEQ ID NO:1 in the sequence listing.

19. The polynucleotide sequence of claim 1, wherein the sequence of (a) encodes a polypeptide given by amino acid numbers 4 to 437 in SEQ ID NO:2 in the sequence listing.

20. A polynucleotide sequence encoding clover yellow vein virus Nuclear Inclusion a protein as given by nucleotide numbers 10 to 1311 in SEQ ID NO: 1.

21. A vector containing the polynucleotide sequence of claim 1.

22. The vector of claim 21, which is an expression vector.

23. A host transformed with the vector of claim 21.

24. A host transformed with the vector of claim 22.

25. An expression system comprising a host transformed with the vector of claim 22.

26. The polynucleotide sequence of claim 1, wherein the sequence encoding the clover yellow vein virus Nuclear Inclusion a protein has a nucleotide sequence consisting of nucleotides 10 to 1311 of SEQ ID NO:1.

27. The polynucleotide sequence of claim 1, further encoding a leader sequence upstream of sequence (a).

28. The polynucleotide sequence of claim 1, wherein one or more amino acid residues are located between the cleavage peptide and the polypeptide.

29. The expression system of claim 25, wherein autolysis by the protein encoded by sequence (a) yields a polypeptide having an additional N-terminal amino acid sequence of which the terminal residue is a residue of glycine, serine or alanine, and an aminopeptidase in the host serves to remove said N-terminal residue.

30. The expression system of claim 25, wherein autolysis by the protein encoded by sequence (a) yields a polypeptide having an additional N-terminal amino acid sequence comprising a C-terminal proline residue and 0, 1 or a plurality of further amino acid residues that are adjacent to and N-terminal to said C-terminal proline residue, and wherein any of said further amino acid residues is removed by aminopeptidase P (EC 3.4.11.9).

31. The expression system of claim 30, wherein after cleavage up to said C-terminal proline residue, said C-terminal proline residue is then removed by the action of proline iminopeptidase.

32. The expression system of claim 25, wherein autolysis by the protein encoded by sequence (a) yields a polypeptide having an additional N-terminal amino acid sequence comprising a C-terminal alanine residue and 0, 1 or a plurality of further amino acid residues that are adjacent to and N-terminal to said C-terminal alanine residue, and wherein any of said further amino acid residues is removed by aminopeptidase P (EC 3.4.11.9),and said C-terminal alanine residue is removed by the action of alanine aminopeptidase (EC 3.4.11.14).

33. An isolated polynucleotide sequence encoding a polypeptide which comprises the amino acid sequence of amino acid numbers 1 to 526 of SEQ ID NO: 12, provided that the polypeptide encoded by the polynucleotide sequence is capable of catalyzing the reduction of dichloroindophenol and oxidized glutathione.

34. An isolated polynucleotide sequence which has a nucleotide sequence consisting of nucleotides 70 to 1647 of SEQ ID NO: 11, wherein said isolated polynucleotide sequence encodes a polypeptide which catalyzes the reduction of dichloroindophenol and oxidized glutathione.

35. The polynucleotide sequence of claim 33, wherein the coding sequence comprises the nucleotide sequence 70 to 1647 indicated in SEQ ID NO:11.

36. The polynucleotide sequence of claim 33, which encodes a polypeptide having the sequence −23 to 526 of SEQ ID NO: 12.

37. A vector containing the polynucleotide sequence of claim 33.

38. An expression vector containing the polynucleotide sequence of claim 33.

39. A host transformed with the vector of claim 37.

40. A host transformed with the vector of claim 38.

41. An expression system comprising the host of claim 40.

42. An isolated DNA which hybridizes under high stringency conditions to nucleotides 10 to 1311 of SEQ ID NO: 1, wherein the corresponding sense strand of said isolated DNA encodes a protein having protease activity and wherein said conditions for hybridization comprise hybridization in 6×SSC at 60 to 70° C. and washing in 0.1×SSC at 60 to 70° C.

43. The expression system of claim 25, wherein the host is *Escherichia coli*.

44. The expression system of claim 41, wherein the host is *Escherichia coli*.

45. An isolated DNA which hybridizes under high stringency conditions to SEQ ID NO: 11, wherein the corresponding sense strand of said isolated DNA encodes a polypeptide having oxidoreductase activity and wherein the conditions for hybridization comprise hybridization in 6×SSC at 60 to 70° C. and washing in 0.1×SSC at 60 to 70° C.

46. The polynucleotide sequence of claim 1, wherein the polypeptide encoded by the sequence of (c) is a polypeptide which comprises the amino acid sequence of amino acid numbers 1 to 526 of SEQ ID NO: 12, provided that the polypeptide encoded by the polynucleotide sequence is capable of catalyzing the reduction of dichloroindophenol and oxidized glutathione.

* * * * *

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 1320 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: N (iv) ANTI-SENSE: N (vi) ORIGINAL SOURCE:
      (A) ORGANISM: Clover Yellow Vein Virus (ix) FEATURE:
      (A) NAME/KEY: CDS
      (B) LOCATION: 1..1320
(D) OTHER INFORMATION:

(ix) FEATURE:
(A) NAME/KEY: mat_peptide
(B) LOCATION: 10..1311
(D) OTHER INFORMATION:

(xi) SEQUENCE DESCRIPTION: SEQ ID NO: 1:

```
AAG TTC CAA GGG AAA AGT AAG AGA ACA AGA CAA AAG TTG AAG TTC AGA        48
Lys Phe Gln Gly Lys Ser Lys Arg Thr Arg Gln Lys Leu Lys Phe Arg
  1               5                  10                  15

GCG GCA AGA GAC ATG AAG GAT CGT TAT GAA GTG CAT GCC GAT GAG GGG        96
Ala Ala Arg Asp Met Lys Asp Arg Tyr Glu Val His Ala Asp Glu Gly
             20                  25                  30

ACT TTA GTG GAA AAT TTT GGA ACT CGT TAT TCA AAG AAA GGC AAG ACA       144
Thr Leu Val Glu Asn Phe Gly Thr Arg Tyr Ser Lys Lys Gly Lys Thr
         35                  40                  45

AAA GGT ACT GTT GTG GGT TTG GGT GCA AAA ACA AGA CGG TTC ACT AAC       192
Lys Gly Thr Val Val Gly Leu Gly Ala Lys Thr Arg Arg Phe Thr Asn
     50                  55                  60

ATG TAT GGT TTT GAC CCC ACG GAG TAT TCA TTT GCT AGG TAT CTT GAT       240
Met Tyr Gly Phe Asp Pro Thr Glu Tyr Ser Phe Ala Arg Tyr Leu Asp
 65                  70                  75                  80

CCA ATC ACG GGT GCA ACA TTG GAT GAA ACC CCA ATT CAC AAT GTA AAT       288
Pro Ile Thr Gly Ala Thr Leu Asp Glu Thr Pro Ile His Asn Val Asn
                 85                  90                  95

TTG GTT GCT GAG CAT TTT GGC GAC ATA AGG CTT GAT ATG GTT GAC AAG       336
Leu Val Ala Glu His Phe Gly Asp Ile Arg Leu Asp Met Val Asp Lys
            100                 105                 110

GAG TTA CTT GAC AAA CAG CAC TTA TAC CTC AAG AGA CCA ATA GAA TGT       384
Glu Leu Leu Asp Lys Gln His Leu Tyr Leu Lys Arg Pro Ile Glu Cys
        115                 120                 125

TAC TTT GTA AAG GAT GCT GGT CAG AAG GTG ATG AGG ATT GAT CTA ACA       432
Tyr Phe Val Lys Asp Ala Gly Gln Lys Val Met Arg Ile Asp Leu Thr
    130                 135                 140

CCC CAC AAC CCA TTG TTG GCA AGC GAT GTT AGC ACA ACC ATA ATG GGT       480
Pro His Asn Pro Leu Leu Ala Ser Asp Val Ser Thr Thr Ile Met Gly
145                 150                 155                 160

TAT CCT GAG AGA GAA GGT GAA CTC CGT CAA ACT GGA AAG GCA AGG TTA       528
Tyr Pro Glu Arg Glu Gly Glu Leu Arg Gln Thr Gly Lys Ala Arg Leu
```

-continued

```
                165                 170                 175
GTC GAC CCA TCA GAG TTG CCC GCG CGG AAT GAG GAT ATT GAT GCA GAG       576
Val Asp Pro Ser Glu Leu Pro Ala Arg Asn Glu Asp Ile Asp Ala Glu
            180                 185                 190

TTT GAG AGT CTA AAT CGC ATA AGT GGT TTG CGC GAC TAT AAT CCC ATT       624
Phe Glu Ser Leu Asn Arg Ile Ser Gly Leu Arg Asp Tyr Asn Pro Ile
            195                 200                 205

TCA CAA AAT GTT TGC TTG CTA ACA AAT GAG TCA GAA GGC CAT AGA GAG       672
Ser Gln Asn Val Cys Leu Leu Thr Asn Glu Ser Glu Gly His Arg Glu
    210                 215                 220

AAG ATG TTT GGA ATT GGA TAT GGT TCA GTG ATC ATT ACA AAT CAA CAT       720
Lys Met Phe Gly Ile Gly Tyr Gly Ser Val Ile Ile Thr Asn Gln His
225                 230                 235                 240

CTG TTC AGA AGG AAT AAT GGG GAG TTA TCA ATT CAA TCC AAG CAT GGC       768
Leu Phe Arg Arg Asn Asn Gly Glu Leu Ser Ile Gln Ser Lys His Gly
                245                 250                 255

TAC TTC AGA TGC CGC AAC ACC ACA AGC TTG AAG ATG CTG CCT TTG GAG       816
Tyr Phe Arg Cys Arg Asn Thr Thr Ser Leu Lys Met Leu Pro Leu Glu
                260                 265                 270

GGA CAT GAC ATT TTG TTG ATT CAG TTA CCA AGG GAC TTT CCA GTG TTT       864
Gly His Asp Ile Leu Leu Ile Gln Leu Pro Arg Asp Phe Pro Val Phe
            275                 280                 285

CCA CAA AAG ATT CGC TTT AGG GAG CCA AGA GTG GAT GAC AAA ATT GTT       912
Pro Gln Lys Ile Arg Phe Arg Glu Pro Arg Val Asp Asp Lys Ile Val
            290                 295                 300

TTG GTC AGC ACA AAT TTC CAG GAA AAG AGT TCC TCG AGC ACG GTC TCA       960
Leu Val Ser Thr Asn Phe Gln Glu Lys Ser Ser Ser Ser Thr Val Ser
305                 310                 315                 320

GAG TCC AGT AAC ATT TCA AGA GTG CAG TCA GCC AAT TTC TAC AAG CAT      1008
Glu Ser Ser Asn Ile Ser Arg Val Gln Ser Ala Asn Phe Tyr Lys His
                325                 330                 335

TGG ATC TCA ACA GTA GCA GGA CAC TGT GGA AAC CCT ATG GTT TCG ACT      1056
Trp Ile Ser Thr Val Ala Gly His Cys Gly Asn Pro Met Val Ser Thr
                340                 345                 350

AAA GAT GGA TTT ATT GTA GGT ATC CAC AGT CTT GCT TCA TTG ACA GGC      1104
Lys Asp Gly Phe Ile Val Gly Ile His Ser Leu Ala Ser Leu Thr Gly
            355                 360                 365

GAC GTT AAC ATC TTC ACA AGC TTT CCG CCG CAG TTT GAG AAC AAA TAT      1152
Asp Val Asn Ile Phe Thr Ser Phe Pro Pro Gln Phe Glu Asn Lys Tyr
            370                 375                 380

CTA CAG AAG CTC AGT GAA CAC ACA TGG TGT AGT GGA TGG AAA CTA AAT      1200
Leu Gln Lys Leu Ser Glu His Thr Trp Cys Ser Gly Trp Lys Leu Asn
385                 390                 395                 400

CTT GGA AAG ATT AGT TGG GGT GGA ATC AAC ATT GTG GAG GAT GCA CCT      1248
Leu Gly Lys Ile Ser Trp Gly Gly Ile Asn Ile Val Glu Asp Ala Pro
                405                 410                 415

GAA GAG CCC TTT ATA ACA TCC AAG ATG GCA AGC CTT CTT AGT GAT TTG      1296
Glu Glu Pro Phe Ile Thr Ser Lys Met Ala Ser Leu Leu Ser Asp Leu
            420                 425                 430

AAT TGT TCA TTC CAA GCA AGT GCG                                      1320
Asn Cys Ser Phe Gln Ala Ser Ala
            435                 440
```

(2) INFORMATION FOR SEQ ID NO: 2:

(i) SEQUENCE CHARACTERISTICS:
        (A) LENGTH: 440 amino acids
        (B) TYPE: amino acid
        (D) TOPOLOGY: linear (ii) MOLECULE TYPE: protein (vi) ORIGINAL SOURCE:
    (A) ORGANISM: Clover Yellow Vein Virus (ix) FEATURE:
    (A) NAME/KEY: mat_peptide
    (B) LOCATION: 4..437
    (D) OTHER INFORMATION:

(xi) SEQUENCE DESCRIPTION: SEQ ID NO: 2:

```
Lys Phe Gln Gly Lys Ser Lys Arg Thr Arg Gln Lys Leu Lys Phe Arg
  1               5                  10                  15

Ala Ala Arg Asp Met Lys Asp Arg Tyr Glu Val His Ala Asp Glu Gly
             20                  25                  30

Thr Leu Val Glu Asn Phe Gly Thr Arg Tyr Ser Lys Lys Gly Lys Thr
         35                  40                  45

Lys Gly Thr Val Val Gly Leu Gly Ala Lys Thr Arg Arg Phe Thr Asn
 50                  55                  60

Met Tyr Gly Phe Asp Pro Thr Glu Tyr Ser Phe Ala Arg Tyr Leu Asp
 65                  70                  75                  80

Pro Ile Thr Gly Ala Thr Leu Asp Glu Thr Pro Ile His Asn Val Asn
                 85                  90                  95

Leu Val Ala Glu His Phe Gly Asp Ile Arg Leu Asp Met Val Asp Lys
                100                 105                 110

Glu Leu Leu Asp Lys Gln His Leu Tyr Leu Lys Arg Pro Ile Glu Cys
            115                 120                 125

Tyr Phe Val Lys Asp Ala Gly Gln Lys Val Met Arg Ile Asp Leu Thr
        130                 135                 140

Pro His Asn Pro Leu Leu Ala Ser Asp Val Ser Thr Thr Ile Met Gly
145                 150                 155                 160

Tyr Pro Glu Arg Glu Gly Glu Leu Arg Gln Thr Gly Lys Ala Arg Leu
                165                 170                 175

Val Asp Pro Ser Glu Leu Pro Ala Arg Asn Glu Asp Ile Asp Ala Glu
            180                 185                 190

Phe Glu Ser Leu Asn Arg Ile Ser Gly Leu Arg Asp Tyr Asn Pro Ile
        195                 200                 205

Ser Gln Asn Val Cys Leu Leu Thr Asn Glu Ser Glu Gly His Arg Glu
210                 215                 220

Lys Met Phe Gly Ile Gly Tyr Gly Ser Val Ile Ile Thr Asn Gln His
225                 230                 235                 240

Leu Phe Arg Arg Asn Asn Gly Glu Leu Ser Ile Gln Ser Lys His Gly
                245                 250                 255

Tyr Phe Arg Cys Arg Asn Thr Thr Ser Leu Lys Met Leu Pro Leu Glu
            260                 265                 270

Gly His Asp Ile Leu Leu Ile Gln Leu Pro Arg Asp Phe Pro Val Phe
        275                 280                 285

Pro Gln Lys Ile Arg Phe Arg Glu Pro Arg Val Asp Asp Lys Ile Val
290                 295                 300

Leu Val Ser Thr Asn Phe Gln Glu Lys Ser Ser Ser Thr Val Ser
305                 310                 315                 320

Glu Ser Ser Asn Ile Ser Arg Val Gln Ser Ala Asn Phe Tyr Lys His
                325                 330                 335

Trp Ile Ser Thr Val Ala Gly His Cys Gly Asn Pro Met Val Ser Thr
            340                 345                 350

Lys Asp Gly Phe Ile Val Gly Ile His Ser Leu Ala Ser Leu Thr Gly
        355                 360                 365
```

```
Asp Val Asn Ile Phe Thr Ser Phe Pro Pro Gln Phe Glu Asn Lys Tyr
    370                 375                 380

Leu Gln Lys Leu Ser Glu His Thr Trp Cys Ser Gly Trp Lys Leu Asn
385                 390                 395                 400

Leu Gly Lys Ile Ser Trp Gly Gly Ile Asn Ile Val Glu Asp Ala Pro
                405                 410                 415

Glu Glu Pro Phe Ile Thr Ser Lys Met Ala Ser Leu Leu Ser Asp Leu
                420                 425                 430

Asn Cys Ser Phe Gln Ala Ser Ala
        435                 440
```

(2) INFORMATION FOR SEQ ID NO: 3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (iii) HYPOTHETICAL: N (iv) ANTI-SENSE: N (xi) SEQUENCE DESCRIPTION: SEQ ID NO: 3:

GTCCATGGGG AAAAGTAAGA GAACA                                    25

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid, synthetic DNA (iii) HYPOTHETICAL: N (iv) ANTI-SENSE: N (xi) SEQUENCE DESCRIPTION: SEQ ID NO: 4:

ACTCTGAGAC CGTGCTCGAG                                        20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid, synthetic DNA (iii) HYPOTHETICAL: N (iv) ANTI-SENSE: N (xi) SEQUENCE DESCRIPTION: SEQ ID NO: 5:

AGGAAAAGAG TTCCTCGAGC                                        20

(2) INFORMATION FOR SEQ ID NO: 6:

(i) SEQUENCE CHARACTERISTICS:
        (A) LENGTH: 36 base pairs
        (B) TYPE: nucleic acid (C) STRANDEDNESS: single
        (D) TOPOLOGY: linear (ii) MOLECULE TYPE: other nucleic acid, synthetic DNA (iii) HYPOTHETICAL: N (iv) ANTI-SENSE: N (xi) SEQUENCE DESCRIPTION: SEQ ID NO: 6:

AATTGTTCAT TCCAAGCACC TGGGCCACCA CCTGGC                                    36

(2) INFORMATION FOR SEQ ID NO: 7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid, synthetic DNA (iii) HYPOTHETICAL: N (iv) ANTI-SENSE: N (xi) SEQUENCE DESCRIPTION: SEQ ID NO: 7:

GCCAGGTGGT GGCCCAGGTG CTTGGAATGA ACAATT                                    36

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid, synthetic DNA (iii) HYPOTHETICAL: N (iv) ANTI-SENSE: N (xi) SEQUENCE DESCRIPTION: SEQ ID NO: 8:

TTGTCAGCAC ACCTGGGAGC TGTAGAGCTC                                           30

(2) INFORMATION FOR SEQ ID NO: 9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: N (xi) SEQUENCE DESCRIPTION: SEQ ID NO: 9:

Ala Pro Gly Pro Pro Pro Gly
1               5

(2) INFORMATION FOR SEQ ID NO: 10:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein

```
      (iii) HYPOTHETICAL: N (xi) SEQUENCE DESCRIPTION: SEQ ID NO: 10:

Pro Gly Pro Pro Pro Gly Pro
 1               5

(2) INFORMATION FOR SEQ ID NO: 11:

(i) SEQUENCE CHARACTERISTICS:
          (A) LENGTH: 1650 base pairs
          (B) TYPE: nucleic acid
          (C) STRANDEDNESS: double
          (D) TOPOLOGY: linear (ii) MOLECULE TYPE: cDNA to mRNA (iii) HYPOTHETICAL: N (iv) ANTI-SENSE: N (vi) ORIGINAL SOURCE:
          (A) ORGANISM: Homo sapiens
          (H) CELL LINE: KM-102

(vii) IMMEDIATE SOURCE:
          (B) CLONE: KM31-7

(ix) FEATURE:
          (A) NAME/KEY: CDS
          (B) LOCATION: 1..1647
          (D) OTHER INFORMATION:

(ix) FEATURE:
          (A) NAME/KEY: mat_peptide
          (B) LOCATION: 70..1647
          (D) OTHER INFORMATION:

(ix) FEATURE:
          (A) NAME/KEY: sig_peptide
          (B) LOCATION: 1..69
          (D) OTHER INFORMATION:

(xi) SEQUENCE DESCRIPTION: SEQ ID NO: 11:
```

| | | | | | | | | | | | | | | | | |
|---|---|---|---|---|---|---|---|---|---|---|---|---|---|---|---|---|
| ATG | TCA | TGT | GAG | GAC | GGT | CGG | GCC | CTG | GAA | GGA | ACG | CTC | TCG | GAA | TTG | 48 |
| Met | Ser | Cys | Glu | Asp | Gly | Arg | Ala | Leu | Glu | Gly | Thr | Leu | Ser | Glu | Leu | |
| -23 | | -20 | | | | -15 | | | | -10 | | | | | | |
| GCC | GCG | GAA | ACC | GAT | CTG | CCC | GTT | GTG | TTT | GTG | AAA | CAG | AGA | AAG | ATA | 96 |
| Ala | Ala | Glu | Thr | Asp | Leu | Pro | Val | Val | Phe | Val | Lys | Gln | Arg | Lys | Ile | |
| | | -5 | | | | | 1 | | | | 5 | | | | | |
| GGC | GGC | CAT | GGT | CCA | ACC | TTG | AAG | GCT | TAT | CAG | GAG | GGC | AGA | CTT | CAA | 144 |
| Gly | Gly | His | Gly | Pro | Thr | Leu | Lys | Ala | Tyr | Gln | Glu | Gly | Arg | Leu | Gln | |
| 10 | | | | 15 | | | | | 20 | | | | | 25 | | |
| AAG | CTA | CTA | AAA | ATG | AAC | GGC | CCT | GAA | GAT | CTT | CCC | AAG | TCC | TAT | GAC | 192 |
| Lys | Leu | Leu | Lys | Met | Asn | Gly | Pro | Glu | Asp | Leu | Pro | Lys | Ser | Tyr | Asp | |
| | | | 30 | | | | | 35 | | | | | 40 | | | |
| TAT | GAC | CTT | ATC | ATC | ATT | GGA | GGT | GGC | TCA | GGA | GGT | CTG | GCA | GCT | GCT | 240 |
| Tyr | Asp | Leu | Ile | Ile | Ile | Gly | Gly | Gly | Ser | Gly | Gly | Leu | Ala | Ala | Ala | |
| | | | 45 | | | | | 50 | | | | | 55 | | | |
| AAG | GAG | GCA | GCC | CAA | TAT | GGC | AAG | AAG | GTG | ATG | GTC | CTG | GAC | TTT | GTC | 288 |
| Lys | Glu | Ala | Ala | Gln | Tyr | Gly | Lys | Lys | Val | Met | Val | Leu | Asp | Phe | Val | |
| | | 60 | | | | | 65 | | | | | 70 | | | | |
| ACT | CCC | ACC | CCT | CTT | GGA | ACT | AGA | TGG | GGT | CTT | GGA | GGA | ACA | TGT | GTG | 336 |
| Thr | Pro | Thr | Pro | Leu | Gly | Thr | Arg | Trp | Gly | Leu | Gly | Gly | Thr | Cys | Val | |
| | 75 | | | | | 80 | | | | | 85 | | | | | |
| AAT | GTG | GGT | TGC | ATA | CCT | AAA | AAA | CTG | ATG | CAT | CAA | GCA | GCT | TTG | TTA | 384 |
| Asn | Val | Gly | Cys | Ile | Pro | Lys | Lys | Leu | Met | His | Gln | Ala | Ala | Leu | Leu | |
| 90 | | | | 95 | | | | | 100 | | | | | 105 | | |

```
GGA CAA GCC CTG CAA GAC TCT CGA AAT TAT GGA TGG AAA GTC GAG GAG        432
Gly Gln Ala Leu Gln Asp Ser Arg Asn Tyr Gly Trp Lys Val Glu Glu
                110                 115                 120

ACA GTT AAG CAT GAT TGG GAC AGA ATG ATA GAA GCT GTA CAG AAT CAC        480
Thr Val Lys His Asp Trp Asp Arg Met Ile Glu Ala Val Gln Asn His
            125                 130                 135

ATT GGC TCT TTG AAT TGG GGC TAC CGA GTA GCT CTG CGG GAG AAA AAA        528
Ile Gly Ser Leu Asn Trp Gly Tyr Arg Val Ala Leu Arg Glu Lys Lys
        140                 145                 150

GTC GTC TAT GAG AAT GCT TAT GGG CAA TTT ATT GGT CCT CAC AGG ATT        576
Val Val Tyr Glu Asn Ala Tyr Gly Gln Phe Ile Gly Pro His Arg Ile
    155                 160                 165

AAG GCA ACA AAT AAT AAA GGC AAA GAA AAA ATT TAT TCA GCA GAG AGA        624
Lys Ala Thr Asn Asn Lys Gly Lys Glu Lys Ile Tyr Ser Ala Glu Arg
170                 175                 180                 185

TTT CTC ATT GCC ACT GGT GAA AGA CCA CGT TAC TTG GGC ATC CCT GGT        672
Phe Leu Ile Ala Thr Gly Glu Arg Pro Arg Tyr Leu Gly Ile Pro Gly
                190                 195                 200

GAC AAA GAA TAC TGC ATC AGC AGT GAT GAT CTT TTC TCC TTG CCT TAC        720
Asp Lys Glu Tyr Cys Ile Ser Ser Asp Asp Leu Phe Ser Leu Pro Tyr
            205                 210                 215

TGC CCG GGT AAG ACC CTG GTT GTT GGA GCA TCC TAT GTC GCT TTG GAG        768
Cys Pro Gly Lys Thr Leu Val Val Gly Ala Ser Tyr Val Ala Leu Glu
        220                 225                 230

TGC GCT GGA TTT CTT GCT GGT ATT GGT TTA GAC GTC ACT GTT ATG GTT        816
Cys Ala Gly Phe Leu Ala Gly Ile Gly Leu Asp Val Thr Val Met Val
    235                 240                 245

AGG TCC ATT CTT CTT AGA GGA TTT GAC CAG GAC ATG GCC AAC AAA ATT        864
Arg Ser Ile Leu Leu Arg Gly Phe Asp Gln Asp Met Ala Asn Lys Ile
250                 255                 260                 265

GGT GAA CAC ATG GAA GAA CAT GGC ATC AAG TTT ATA AGA CAG TTC GTA        912
Gly Glu His Met Glu Glu His Gly Ile Lys Phe Ile Arg Gln Phe Val
                270                 275                 280

CCA ATT AAA GTT GAA CAA ATT GAA GCA GGG ACA CCA GGC CGA CTC AGA        960
Pro Ile Lys Val Glu Gln Ile Glu Ala Gly Thr Pro Gly Arg Leu Arg
            285                 290                 295

GTA GTA GCT CAG TCC ACC AAT AGT GAG GAA ATC ATT GAA GGA GAA TAT       1008
Val Val Ala Gln Ser Thr Asn Ser Glu Glu Ile Ile Glu Gly Glu Tyr
        300                 305                 310

AAT ACG GTG ATG CTG GCA ATA GGA AGA GAT GCT TGC ACA AGA AAA ATT       1056
Asn Thr Val Met Leu Ala Ile Gly Arg Asp Ala Cys Thr Arg Lys Ile
    315                 320                 325

GGC TTA GAA ACC GTA GGG GTG AAG ATA AAT GAA AAG ACT GGA AAA ATA       1104
Gly Leu Glu Thr Val Gly Val Lys Ile Asn Glu Lys Thr Gly Lys Ile
330                 335                 340                 345

CCT GTC ACA GAT GAA GAA CAG ACC AAT GTG CCT TAC ATC TAT GCC ATT       1152
Pro Val Thr Asp Glu Glu Gln Thr Asn Val Pro Tyr Ile Tyr Ala Ile
                350                 355                 360

GGC GAT ATA TTG GAG GAT AAG GTG GAG CTC ACC CCA GTT GCA ATC CAG       1200
Gly Asp Ile Leu Glu Asp Lys Val Glu Leu Thr Pro Val Ala Ile Gln
            365                 370                 375

GCA GGA AGA TTG CTG GCT CAG AGG CTC TAT GCA GGT TCC ACT GTC AAG       1248
Ala Gly Arg Leu Leu Ala Gln Arg Leu Tyr Ala Gly Ser Thr Val Lys
        380                 385                 390

TGT GAC TAT GAA AAT GTT CCA ACC ACT GTA TTT ACT CCT TTG GAA TAT       1296
Cys Asp Tyr Glu Asn Val Pro Thr Thr Val Phe Thr Pro Leu Glu Tyr
    395                 400                 405

GGT GCT TGT GGC CTT TCT GAG GAG AAA GCT GTG GAG AAG TTT GGG GAA       1344
Gly Ala Cys Gly Leu Ser Glu Glu Lys Ala Val Glu Lys Phe Gly Glu
410                 415                 420                 425
```

-continued

```
GAA AAT ATT GAG GTT TAC CAT AGT TAC TTT TGG CCA TTG GAA TGG ACG    1392
Glu Asn Ile Glu Val Tyr His Ser Tyr Phe Trp Pro Leu Glu Trp Thr
                430                 435                 440

ATT CCG TCA AGA GAT AAC AAC AAA TGT TAT GCA AAA ATA ATC TGT AAT    1440
Ile Pro Ser Arg Asp Asn Asn Lys Cys Tyr Ala Lys Ile Ile Cys Asn
            445                 450                 455

ACT AAA GAC AAT GAA CGT GTT GTG GGC TTT CAC GTA CTG GGT CCA AAT    1488
Thr Lys Asp Asn Glu Arg Val Val Gly Phe His Val Leu Gly Pro Asn
        460                 465                 470

GCT GGA GAA GTT ACA CAA GGC TTT GCA GCT GCG CTC AAA TGT GGA CTG    1536
Ala Gly Glu Val Thr Gln Gly Phe Ala Ala Ala Leu Lys Cys Gly Leu
    475                 480                 485

ACC AAA AAG CAG CTG GAC AGC ACA ATT GGA ATC CAC CCT GTC TGT GCA    1584
Thr Lys Lys Gln Leu Asp Ser Thr Ile Gly Ile His Pro Val Cys Ala
490                 495                 500                 505

GAG GTA TTC ACA ACA TTG TCT GTG ACC AAG CGC TCT GGG GCA AGC ATC    1632
Glu Val Phe Thr Thr Leu Ser Val Thr Lys Arg Ser Gly Ala Ser Ile
                510                 515                 520

CTC CAG GCT GGC TGC TGA                                            1650
Leu Gln Ala Gly Cys
                525
```

(2) INFORMATION FOR SEQ ID NO: 12:

(i) SEQUENCE CHARACTERISTICS:
        (A) LENGTH: 549 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Ser Cys Glu Asp Gly Arg Ala Leu Glu Gly Thr Leu Ser Glu Leu
-23         -20                 -15                 -10

Ala Ala Glu Thr Asp Leu Pro Val Val Phe Val Lys Gln Arg Lys Ile
        -5                   1                   5

Gly Gly His Gly Pro Thr Leu Lys Ala Tyr Gln Glu Gly Arg Leu Gln
 10                 15                  20                  25

Lys Leu Leu Lys Met Asn Gly Pro Glu Asp Leu Pro Lys Ser Tyr Asp
                 30                  35                  40

Tyr Asp Leu Ile Ile Ile Gly Gly Ser Gly Gly Leu Ala Ala Ala
                 45                  50                  55

Lys Glu Ala Ala Gln Tyr Gly Lys Lys Val Met Val Leu Asp Phe Val
             60                  65                  70

Thr Pro Thr Pro Leu Gly Thr Arg Trp Gly Leu Gly Gly Thr Cys Val
         75                  80                  85

Asn Val Gly Cys Ile Pro Lys Lys Leu Met His Gln Ala Ala Leu Leu
 90                  95                 100                 105

Gly Gln Ala Leu Gln Asp Ser Arg Asn Tyr Gly Trp Lys Val Glu Glu
                110                 115                 120

Thr Val Lys His Asp Trp Asp Arg Met Ile Glu Ala Val Gln Asn His
                125                 130                 135

Ile Gly Ser Leu Asn Trp Gly Tyr Arg Val Ala Leu Arg Glu Lys Lys
         140                 145                 150

Val Val Tyr Glu Asn Ala Tyr Gly Gln Phe Ile Gly Pro His Arg Ile
     155                 160                 165

Lys Ala Thr Asn Asn Lys Gly Lys Glu Lys Ile Tyr Ser Ala Glu Arg
170                 175                 180                 185
```

```
Phe Leu Ile Ala Thr Gly Glu Arg Pro Arg Tyr Leu Gly Ile Pro Gly
            190                 195                 200
Asp Lys Glu Tyr Cys Ile Ser Ser Asp Asp Leu Phe Ser Leu Pro Tyr
            205                 210                 215
Cys Pro Gly Lys Thr Leu Val Val Gly Ala Ser Tyr Val Ala Leu Glu
            220                 225                 230
Cys Ala Gly Phe Leu Ala Gly Ile Gly Leu Asp Val Thr Val Met Val
            235                 240                 245
Arg Ser Ile Leu Leu Arg Gly Phe Asp Gln Asp Met Ala Asn Lys Ile
250                 255                 260                 265
Gly Glu His Met Glu Glu His Gly Ile Lys Phe Ile Arg Gln Phe Val
            270                 275                 280
Pro Ile Lys Val Glu Gln Ile Glu Ala Gly Thr Pro Gly Arg Leu Arg
            285                 290                 295
Val Val Ala Gln Ser Thr Asn Ser Glu Glu Ile Ile Glu Gly Glu Tyr
            300                 305                 310
Asn Thr Val Met Leu Ala Ile Gly Arg Asp Ala Cys Thr Arg Lys Ile
315                 320                 325
Gly Leu Glu Thr Val Gly Val Lys Ile Asn Glu Lys Thr Gly Lys Ile
330                 335                 340                 345
Pro Val Thr Asp Glu Glu Gln Thr Asn Val Pro Tyr Ile Tyr Ala Ile
            350                 355                 360
Gly Asp Ile Leu Glu Asp Lys Val Glu Leu Thr Pro Val Ala Ile Gln
            365                 370                 375
Ala Gly Arg Leu Leu Ala Gln Arg Leu Tyr Ala Gly Ser Thr Val Lys
            380                 385                 390
Cys Asp Tyr Glu Asn Val Pro Thr Thr Val Phe Thr Pro Leu Glu Tyr
395                 400                 405
Gly Ala Cys Gly Leu Ser Glu Glu Lys Ala Val Glu Lys Phe Gly Glu
410                 415                 420                 425
Glu Asn Ile Glu Val Tyr His Ser Tyr Phe Trp Pro Leu Glu Trp Thr
            430                 435                 440
Ile Pro Ser Arg Asp Asn Asn Lys Cys Tyr Ala Lys Ile Ile Cys Asn
            445                 450                 455
Thr Lys Asp Asn Glu Arg Val Val Gly Phe His Val Leu Gly Pro Asn
            460                 465                 470
Ala Gly Glu Val Thr Gln Gly Phe Ala Ala Ala Leu Lys Cys Gly Leu
            475                 480                 485
Thr Lys Lys Gln Leu Asp Ser Thr Ile Gly Ile His Pro Val Cys Ala
490                 495                 500                 505
Glu Val Phe Thr Thr Leu Ser Val Thr Lys Arg Ser Gly Ala Ser Ile
            510                 515                 520
Leu Gln Ala Gly Cys
            525

(2) INFORMATION FOR SEQ ID NO: 13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid, synthetic DNA (iii) HYPOTHETICAL: N
```

(iv) ANTI-SENSE: N (xi) SEQUENCE DESCRIPTION: SEQ ID NO: 13:

TAAATAAATA AATAA                                                          15

(2) INFORMATION FOR SEQ ID NO: 14:

(i) SEQUENCE CHARACTERISTICS:
         (A) LENGTH: 66 base pairs
         (B) TYPE: nucleic acid
         (C) STRANDEDNESS: double
         (D) TOPOLOGY: linear (ii) MOLECULE TYPE: other nucleic acid, synthetic DNA (iii) HYPOTHETICAL: N (iv) ANTI-SENSE: N (xi) SEQUENCE DESCRIPTION: SEQ ID NO: 14:

CTAGCGCTCT GGGGCAAGCA TCCTCCAGGC TGGCTGCCAC CACCACCACC ACCACTGATC          60

TAGACT                                                                    66

(2) INFORMATION FOR SEQ ID NO: 15:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid, synthetic DNA (iii) HYPOTHETICAL: N (iv) ANTI-SENSE: N (xi) SEQUENCE DESCRIPTION: SEQ ID NO: 15:

GGTCAGCACA AATTTCCA                                                       18

(2) INFORMATION FOR SEQ ID NO: 16:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid, synthetic DNA (iii) HYPOTHETICAL: N (iv) ANTI-SENSE: N (xi) SEQUENCE DESCRIPTION: SEQ ID NO: 16:

AAACACAACT TGGAATGAAC AATT                                                24

(2) INFORMATION FOR SEQ ID NO: 17:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid, synthetic DNA (iii) HYPOTHETICAL: N -continued

```
    (iv) ANTI-SENSE: N (xi) SEQUENCE DESCRIPTION: SEQ ID NO: 17:

TCATTCCAAG TTGTGTTTGT GAAA                                              24

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid, synthetic DNA (iii) HYPOTHETICAL: N (iv) ANTI-SENSE: N (xi) SEQUENCE DESCRIPTION: SEQ ID NO: 18:

CATAGGATGC TCCAACAA                                                     18

(2) INFORMATION FOR SEQ ID NO: 19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 19:

Asn Cys Ser Phe Gln Xaa
 1               5
```